US012569526B2

(12) United States Patent
Mcfadden et al.

(10) Patent No.: US 12,569,526 B2
(45) Date of Patent: Mar. 10, 2026

(54) ONCOLYTIC VIRUS PLATFORM TO TREAT HEMATOLOGICAL CANCER

(71) Applicant: ARIZONA BOARD OF REGENTS ON BEHALF OF ARIZONA STATE UNIVERSITY, Scottsdale, AZ (US)

(72) Inventors: Douglas Grant Mcfadden, Tempe, AZ (US); Lino Torres-Dominguez, Scottsdale, AZ (US); Nancy Villa, Scottsdale, AZ (US); Mohammed Masmudur Rahman, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 785 days.

(21) Appl. No.: 17/274,051

(22) PCT Filed: Sep. 4, 2019

(86) PCT No.: PCT/US2019/049598
§ 371 (c)(1),
(2) Date: Mar. 5, 2021

(87) PCT Pub. No.: WO2020/051248
PCT Pub. Date: Mar. 12, 2020

(65) Prior Publication Data
US 2021/0252086 A1     Aug. 19, 2021

Related U.S. Application Data

(60) Provisional application No. 62/727,307, filed on Sep. 5, 2018.

(51) Int. Cl.
| | |
|---|---|
| *A61K 35/768* | (2015.01) |
| *A61K 40/10* | (2025.01) |
| *A61K 40/42* | (2025.01) |
| *C07K 16/28* | (2006.01) |
| *C12N 7/00* | (2006.01) |
| *A61K 40/50* | (2025.01) |

(52) U.S. Cl.
CPC ............ *A61K 35/768* (2013.01); *A61K 40/10* (2025.01); *A61K 40/42* (2025.01); *C07K 16/283* (2013.01); *C12N 7/00* (2013.01); *A61K 40/50* (2025.01); *A61K 2239/31* (2023.05); *C07K 2317/622* (2013.01); *C07K 2319/60* (2013.01); *C12N 2710/24032* (2013.01)

(58) Field of Classification Search
None
See application file for complete search history.

(56) References Cited

U.S. PATENT DOCUMENTS

| | | | |
|---|---|---|---|
| 7,582,614 B2 | 9/2009 | McFadden et al. | |
| 9,803,021 B2 | 10/2017 | Morrison | |
| 9,908,938 B2 | 3/2018 | Koenig et al. | |
| 11,117,934 B2 * | 9/2021 | McFadden ......... | C07K 14/5434 |
| 2012/0141427 A1 | 6/2012 | Bertagnoli et al. | |
| 2013/0230517 A1 * | 9/2013 | Grewal ................ | A61K 38/212 424/134.1 |
| 2016/0229892 A1 * | 8/2016 | Hazlehurst ....... | C07K 14/70596 |
| 2017/0275375 A1 | 9/2017 | Rossi et al. | |
| 2018/0021378 A1 | 1/2018 | Kang et al. | |

FOREIGN PATENT DOCUMENTS

| | | | |
|---|---|---|---|
| CN | 106755103 A | 5/2017 | |
| CN | 107164338 A | 9/2017 | |
| JP | 2002539829 A | 11/2002 | |
| JP | 2015501839 A | 1/2015 | |
| WO | WO-2006094385 A1 | 9/2006 | |
| WO | WO-2007143548 A2 | 12/2007 | |
| WO | WO-2007147901 A1 * | 12/2007 | ......... C07K 16/2803 |
| WO | WO-2012018687 A1 | 2/2012 | |
| WO | WO-2014089354 A1 | 6/2014 | |
| WO | WO-2016041616 A1 * | 3/2016 | ............. A61K 38/09 |
| WO | WO-2016109668 A1 | 7/2016 | |
| WO | WO-2017210058 A1 | 12/2017 | |
| WO | WO-2017214092 A1 * | 12/2017 | .............. A61P 31/00 |
| WO | WO-2018006005 A1 | 1/2018 | |
| WO | WO-2018049248 A1 | 3/2018 | |
| WO | WO-2018049261 A1 | 3/2018 | |
| WO | WO-2018156740 A1 * | 8/2018 | ......... A61K 39/3955 |
| WO | WO-2018157165 A1 * | 8/2018 | .......... A61K 38/177 |
| WO | WO-2020051248 A1 | 3/2020 | |
| WO | WO-2020198690 A1 | 10/2020 | |

(Continued)

OTHER PUBLICATIONS

Liu et al. Myxoma Virus Expressing Interleukin-15 Fails to Cause Lethal Myxomatosis in European RabbitsJ Virol. Jun. 2009;83(11):5933-8. (Year: 2009).*
Barrett et al. M135R Is a Novel Cell Surface Virulence Factor of Myxoma Virus. J Virol. Jan. 2007;81(1):106-14. (Year: 2007).*
Niell et al. Decorin as a multivalent therapeutic agent against cancer. Advanced Drug Delivery Reviews 97 (2016) 174-185. (Year: 2016).*
National Cancer Institute. Types of Treatment ( accessed at accessed at http://web.archive.org/web/20150517031351/https://www.cancer.gov/aboutcancer/treatment/types with WayBack Machine; 2015) (Year: 2015).*

(Continued)

*Primary Examiner* — Valarie E Bertoglio
*Assistant Examiner* — Briana N Ebbinghaus
(74) *Attorney, Agent, or Firm* — Riverside Law LLP

(57) ABSTRACT

The disclosure provides Myxoma virus that expresses one or more immunomodulatory transgenes and its use in inhibiting and/or treating a hematological cancer in a subject. The disclosure also provides a leukocyte having a Myxoma virus that expresses one or more immunomodulatory transgenes and the use of the leukocyte for inhibiting and/or treating a hematological cancer in a subject.

12 Claims, 23 Drawing Sheets

Specification includes a Sequence Listing.

(56) References Cited

FOREIGN PATENT DOCUMENTS

| WO | WO-2021046048 A1 | 3/2021 |
| WO | WO-2021072264 A1 | 4/2021 |

OTHER PUBLICATIONS

Muthana et al. Macrophage Delivery of an Oncolytic Virus Abolishes Tumor Regrowth and Metastasis after Chemotherapy or IrradiationCancer Res. Mar. 1, 2011;71(5):1805-15.(Year: 2011).*

Yang et al. Systemic Delivery of an Oncolytic Adenovirus Expressing Decorin for the Treatment of Breast Cancer Bone Metastases. Hum Gene Ther. Dec. 2015;26(12):813-25. (Year: 2015).*

Zou et al. Immunotherapy based on bispecific T-cell engager with hIgG1 Fc sequence as a new therapeutic strategy in multiple myeloma. Cancer Sci. May 2015;106(5):512-21.(Year: 2015).*

Pace et al. Sickle Cell Disease: Genetics, Cellular and Molecular Mechanisms, and Therapies. Anemia. 2012; 2012: 143594. (Year: 2012).*

Bruenke et al. A recombinant bispecific single-chain Fv antibody against HLA class II and FccRIII (CD16) triggers effective lysis of lymphoma cells. Br J Haematol. Apr. 2004;125(2):167-79. (Year: 2004).*

National Library of Medicine. Mus musculus anti-human Fc gamma receptor III 3G8 gamma heavy chain variable region mRNA, partial cds (accessed at: https://www.ncbi.nlm.nih.gov/nuccore/AY173025) (Year: 2004).*

National Library of Medicine.Mus musculus anti-human Fc gamma receptor III 3G8 kappa light chain variable region mRNA, partial cds. (accessed at: https://www.ncbi.nlm.nih.gov/nuccore/AY173024) (Year: 2004).*

Cheung et al. Polymorphic Variants of Light (TNF Superfamily-14) Alter Receptor Avidity and Bioavailability. J Immunol. Jun. 30, 2010;185(3):1949-1958. (Year: 2010).*

Seilder. The galactosaminoglycan-containing decorin and its impact on diseases. Curr Opin Struct Biol. Oct. 2012;22(5):578-82. Epub Aug. 8, 2012. (Year: 2012).*

Felices et al. Generation of BiKEs and TriKEs to improve NK cell-mediated targeting of tumor cells. Methods Mol Biol. 2016;1441:333-346. (Year: 2016).*

Bartee et al., Selective purging of human multiple myeloma cells from autologous stem cell transplantation grafts using oncolytic myxoma virus. Biol Blood Marrow Transplant 18(10):1540-1551 (2012).

Bustoros et al., Established and Novel Prognostic Biomarkers in Multiple Myeloma. Am Soc Clin Oncol Educ Book 37:548-560 (2017).

Cameron et al., The complete DNA sequence of myxoma virus. Virology 264(2):298-318 (1999).

Chan et al., Oncolytic Myxoma Virus: The path to clinic. Vaccine. 31(39): 4252-4258 (2013).

Chan et al., Oncolytic Poxviruses. Annu Rev Virol 1(1): 119-141 (2014).

Davis et al., Natural killer cells unleashed: Checkpoint receptor blockade and BiKE/TriKE utilization in NK-mediated anti-tumor immunity. Semin Immunol 31:64-75 (2017).

Genbank Accession No. EU552531 (2019).

Gleason et al., Bispecific and trispecific killer cell engagers directly activate human NK cells through CD16 signaling and induce cytotoxicity and cytokine production. Mol Cancer Ther 11(12):2674-2684 (2012).

Hari, Recent advances in understanding multiple myeloma. Hematol Oncol Stem Cell There 10(4):267-271 (2017).

Hoyos et al., The immunotherapy era of myeloma: monoclonal antibodies, vaccines, and adoptive T-cell therapies. Blood 128(13):1679-1687 (2016).

Jiang et al., Enhanced antitumor efficacy of a novel oncolytic adenovirus combined with temozolomide in the treatment of melanoma in vivo. J Cancer Res Clin Oncol 141(1):75-85 (2015).

Kaliberova et al., CRAdRGDflt-IL24 virotherapy in combination with chemotherapy of experimental glioma. Cancer Gene Ther 16(10):794-805 (2009).

Kawano et al., Targeting the bone marrow microenvironment in multiple myeloma. Immunol Rev 263(1):160-72 (2015).

Kim et al., Myxoma virus targets primary human leukemic stem and progenitor cells while sparing normal hematopoietic stem and progenitor cells. Leukemia 23(12):2313-2317 (2009).

Landgren et al., MRD Testing in Multiple Myeloma: The Main Future Driver for Modern Tailored Treatment. Semin Hematol 55(1):44-50 (2018).

Lilly et al., Ex vivo oncolytic virotherapy with myxoma virus arms multiple allogeneic bone marrow transplant leukocytes to enhance graft versus tumor. Molecular Therapy Oncolytics 4:31-40 (2016).

Mossman et al. Myxoma virus M-T7, a secreted homolog of the interferon-gamma receptor, is a critical virulence factor for the development of myxomatosis in European rabbits. Virology 215:17-30 (1996).

Nayerossadat et al. Viral and nonviral delivery systems for gene delivery. Adv Biomed Res 1:27 (2012).

NCBI Reference Sequence NM_001190451.2 (2021).

Nemani et al., Role of decorin in multiple myeloma (MM) bone marrow microenvironment. J Bone Miner Res 30(3):465-70 (2015).

PCT/US2019/049598 International Search Report and Written Opinion dated Feb. 5, 2020.

PCT/US2020/055073 International Search Report and Written Opinion dated Jan. 29, 2021.

Stanford et al., Myxoma virus and oncolytic virotherapy: a new biologic weapon in the war against cancer. Expert Opin Biol Ther 7(9):1415-1425 (2007).

Sypula et al., Myxoma virus tropism in human tumor cells. Gene therapy & molecular biology 8:103-114 (2004).

Tang et al., Facilitating T Cell Infiltration in Tumor Microenvironment Overcomes Resistance to PD-L1 Blockade. Cancer Cell 29(3):285-296 (2016).

Twumasi-Boateng et al., Oncolytic viruses as engineering platforms for combination immunotherapy. Nature Reviews Cancer 8(7):419-432 (2018).

Villa et al., Myxoma virus suppresses proliferation of activated T lymphocytes yet permits oncolytic virus transfer to cancer cells. Blood 125(24):3778-3788 (2015).

Wang et al., Infection of human cancer cells with myxoma virus requires Akt activation via interaction with a viral ankyrin-repeat host range factor. PNAS103(12):4640-4645 (2006).

Xu et al., The systemic delivery of an oncolytic adenovirus expressing decorin inhibits bone metastasis in a mouse model of human prostate cancer. Gene Ther 22(3): 247-256 (2015).

Yu et al., Priming of naive T cells inside tumors leads to eradication of established tumors. Nat Immunol 5(2):141-149 (2004).

Yu et al., Targeting tumors with Light to generate metastasis-clearing immunity. Cytokine Growth Factor Rev 19(3-4):285-294 (2008).

Bartee et al.: Tumor-Localized Secretion of Soluble PD1 Enhances Oncolytic Virotherapy. Cancer Res. 77(11):2952-2963 (2017).

De Graaf et al. Armed oncolytic viruses: A kick-start for anti-tumor immunity. Cytokine Growth Factor Rev 41:28-39 (2018).

Hodgins et al. Killers 2.0: NK cell therapies at the forefront of cancer control. J Clin Invest 129(9):3499-3510 (2019).

Liu et al., The immunoregulatory properties of oncolytic myxoma virus and their implications in therapeutics. Microbes Infect 12(14-15):1144-1152 (2010).

Rahman et al.: Oncolytic viral purging of leukemic hematopoietic stem and progenitor cells with Myxoma virus. Cytokine Growth Factor Rev. 21(2-3):169-175 (2010).

Zou et al. Immunotherapy based on bispecific T-cell engager with hIgG1 Fc sequence as a new therapeutic strategy in multiple myeloma. Cancer Sci 106(5):512-521 (2015).

* cited by examiner

FIG. 2A

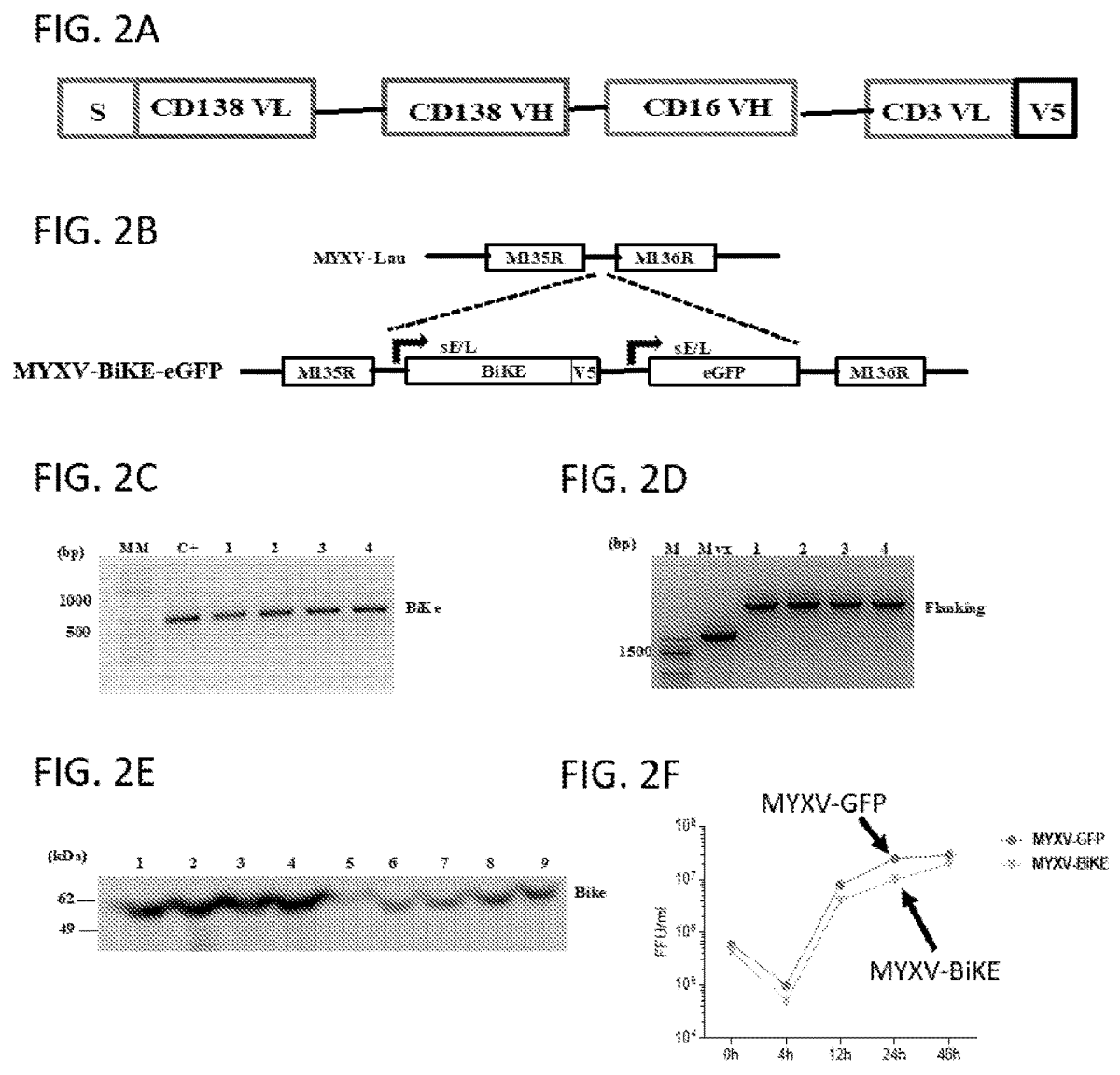

| S | CD138 VL | | CD138 VH | CD16 VH | | CD3 VL | V5 |

FIG. 2B

MYXV-Lau — [ MII35R ]  [ MII36R ] —

MYXV-BiKE-eGFP — [ MII35R ] ⌐ sE/L [ BiKE | V5 ] ⌐ sE/L [ eGFP ] [ MII36R ] —

FIG. 2C (bp)    MM   C+   1    2    3    4
1000
                                        BiKe
500

FIG. 2D (bp)    M   Myx   1    2    3    4
                                        Flanking
1500

FIG. 2E (kDa)   1    2    3    4    5    6    7    8    9
62—                                              Bike
49—

FIG. 2F

MYXV-GFP

MYXV-BiKE

FFU/ml : $10^8$, $10^7$, $10^6$, $10^5$, $10^4$ 0h  4h  12h  24h  48h

- MYXV-GFP
- MYXV-BiKE

Mu LIGHT                    Hu LIGHT

Patient #3_vMyx-hu-LIGHT-TdTomato

Patient #3_vMyx-huLIGHT gating on CD138⁺TdTomato⁻

Patient #3_vMyx-hu-BiKE-GFP

<u>Patient #3_vMyx-huBiKE-GFP gating on CD138⁺GFP⁻</u>

Gating on CD138⁺GFP⁻

Patient #4_vMyx-huBiKE-GFP

Patient #4_vMyx-huBiKE-GFP gating on CD138⁺GFP⁻

Gating on CD138⁺GFP⁻

Patient #4_vMyx-mDecorin-GFP

Patient #4_vMyx-mDecorin-GFP gating on CD138⁺GFP⁻

Gating on CD138⁺GFP⁻

ONCOLYTIC VIRUS PLATFORM TO TREAT HEMATOLOGICAL CANCER

CROSS REFERENCE

This application is a national phase entry of International Application No. PCT/US2019/049598, filed Sep. 4, 2019, which claims the benefit of U.S. Provisional Application No. 62/727,307 filed Sep. 5, 2018, each of which is incorporated herein by reference in its entirety.

SEQUENCE LISTING STATEMENT

The instant application contains a Sequence Listing which has been submitted electronically in ASCII format and is hereby incorporated by reference in its entirety. Said ASCII copy, created on Oct. 7, 2019, is named 55842-705_601_SL.txt and is 36,918 bytes in size.

TECHNICAL FIELD

This disclosure relates to myxoma viruses and their uses for treatment of cancers, for example, treatment of hematological cancers with a myxoma virus that expresses one or more immunomodulatory transgenes, such as BiKE, LIGHT, and/or Decorin.

BACKGROUND

Current treatments used to treat various types of cancer tend to work by poisoning or killing the cancerous cell. Unfortunately, treatments that are toxic to cancer cells typically tend to be toxic to healthy cells as well. Moreover, effective treatments for cancer remain elusive. Current mainstream therapies such as chemotherapy and radiotherapy can have a narrow therapeutic window (e.g., a concentration high enough to achieve efficacy but low enough to avoid toxicity). These types of therapies are considered blunt tools that have limited applicability due to the varying types of tumor cells and the limited window in which these treatments can be administered.

SUMMARY

Disclosed herein, in some aspects, is a myxoma virus (MYXV) comprising one or more immunomodulatory transgenes, wherein the one or more immunomodulatory transgenes encode BiKE (Bi-specific Natural Killer and Neutrophil engager), LIGHT (Lymphotoxins-like, exhibits Inducible expression, and competes with HSV Glycoprotein D for Herpesvirus entry mediator (HVEM), a receptor expressed by T lymphocytes), Decorin, or a combination thereof.

In some embodiments, the myxoma virus comprises MYXV-BiKE. In some embodiments, the BiKE binds to an antigen present on a natural killer cell, a neutrophil, or a combination thereof. In some embodiments, the BiKE binds to an antigen present on a hematologic cancer cell. In some embodiments, the BiKE binds to an antigen present on a myeloma cell. In some embodiments, the BiKE binds to an antigen present on a leukemia cell. In some embodiments, the BiKE binds to an antigen present on a lymphoma cell.

In some embodiments, the BiKE binds to CD16. In some embodiments, the BiKE binds CD138. In some embodiments, the BiKE comprises one or more single chain variable fragments (scFvs). In some embodiments, the BiKE comprises one or more humanized single chain variable fragments (scFvs). In some embodiments, the BiKE comprises a sequence that is at least 70% identical to any one of SEQ ID NOs: 6 or 16-31. In some embodiments, the BiKE is between the M135 and M136 open reading frames of the myxoma virus genome. In some embodiments, the myxoma virus comprises MYXV-huBiKE-GFP. In some embodiments, the myxoma virus comprises MYXV-LIGHT. In some embodiments, the LIGHT comprises a sequence from human LIGHT. In some embodiments, the LIGHT comprises a sequence that is at least 70% identical to any one of SEQ ID NOs: 13-15. In some embodiments, the LIGHT is between the M135 and M136 open reading frames of the myxoma virus genome. In some embodiments, the myxoma virus comprises MYXV-FLuc-huLIGHT-TdTomato. In some embodiments, the myxoma virus comprises MYXV-Decorin. In some embodiments, the Decorin comprises a sequence from human Decorin. In some embodiments, the Decorin comprises a sequence from mouse Decorin. In some embodiments, the Decorin comprises a sequence that is at least 70% identical to any one of SEQ ID NOs: 7-12. In some embodiments, the Decorin is between the M135 and M136 open reading frames of the myxoma virus genome. In some embodiments, the myxoma virus comprises MYXV-mDecorin-GFP. In some embodiments, the myxoma virus further comprises a reporter gene. In some embodiments, the reporter gene is a fluorescent protein. In some embodiments, the reporter gene is a luminescent substrate or enzyme. In some embodiments, the myxoma virus further comprises a deletion in the myxoma virus genome. In some embodiments, the myxoma virus comprises a deletion or disruption of one or more genes selected from the group consisting of M001R, M002R, M003.1R, M003.2R, M004.1R, M004R, M005R, M006R, M007R, M008.1R, M008R, M009L, M013, M036L, M063L, M11L, M128L, M131R, M135R, M136R, M141R, M148R, M151R, M152R, M153R, M154L, M156R, M-T2, M-T4, M-T5, M-T7, and SOD. In some embodiments, the myxoma virus comprises a deletion of M135. In some embodiments the myxoma virus is part of a composition comprising the myxoma virus and a pharmaceutically acceptable carrier.

Disclosed herein, in some aspects, is a method of treating a hematological cancer in a subject in need thereof, comprising administering to the subject a myxoma virus that comprises one or more immunomodulatory transgenes.

In some embodiments, the one or more immunomodulatory transgenes comprise BiKE, LIGHT, Decorin, or a combination thereof. In some embodiments, the myxoma virus comprises MYXV-BiKE. In some embodiments, the BiKE binds to an antigen present on a natural killer cell, a neutrophil, or a combination thereof. In some embodiments, the BiKE binds to an antigen present on a hematologic cancer cell. In some embodiments, the BiKE binds to an antigen present on a myeloma cell. In some embodiments, the BiKE binds to an antigen present on a leukemia cell. In some embodiments, the BiKE binds to an antigen present on a lymphoma cell. In some embodiments, the BiKE binds to CD16. In some embodiments, the BiKE binds CD138. In some embodiments, the BiKE comprises one or more single chain variable fragments (scFvs). In some embodiments, the BiKE comprises a sequence that is at least 70% identical to any one of SEQ ID NOs: 6 or 16-31. In some embodiments, the BiKE is between the M135 and M136 open reading frames of the myxoma virus genome. In some embodiments, the myxoma virus comprises MYXV-huBiKE-GFP. In some embodiments, the myxoma virus comprises MYXV-LIGHT.

In some embodiments, the LIGHT comprises a sequence from human LIGHT. In some embodiments, the LIGHT comprises a sequence that is at least 70% identical to any one of SEQ ID NOs: 13-15. In some embodiments, the LIGHT is between the M135 and M136 open reading frames of the myxoma virus genome. In some embodiments, the myxoma virus comprises MYXV-FLuc-huLIGHT-TdTomato. In some embodiments, the myxoma virus comprises MYXV-Decorin. In some embodiments, the Decorin comprises a sequence from human Decorin.

In some embodiments, the Decorin comprises a sequence from mouse Decorin. In some embodiments, the Decorin comprises a sequence that is at least 70% identical to any one of SEQ ID NOs: 7-12. In some embodiments, the Decorin is between the M135 and M136 open reading frames of the myxoma virus genome. In some embodiments, the myxoma virus comprises MYXV-mDecorin-GFP. In some embodiments, the myxoma virus further comprises a reporter gene. In some embodiments, the reporter gene is a fluorescent protein. In some embodiments, the reporter gene is a luminescent substrate or enzyme. In some embodiments, the myxoma virus further comprises a deletion in the myxoma virus genome. In some embodiments, the myxoma virus comprises a deletion or disruption of one or more genes selected from the group consisting of M001R, M002R, M003.1R, M003.2R, M004.1R, M004R, M005R, M006R, M007R, M008.1R, M008R, M009L, M013, M036L, M063L, M11L, M128L, M131R, M135R, M136R, M141R, M148R, M151R, M152R, M153R, M154L, M156R, M-T2, M-T4, M-T5, M-T7, and SOD. In some embodiments, the myxoma virus comprises a deletion of M135. In some embodiments, the subject is a human. In some embodiments, the myxoma virus is capable of infecting cells that have a deficient innate anti-viral response. In some embodiments, the myxoma virus is capable of infecting cancer cells. In some embodiments, the hematological cancer is a myeloma, leukemia, or lymphoma. In some embodiments, the hematological cancer is multiple myeloma.

Disclosed herein, in some aspects, is a method of treating a hematological cancer in a subject in need thereof, comprising administering to the subject a leukocyte, wherein the leukocyte comprises a myxoma virus that comprises one or more immunomodulatory transgenes.

In some embodiments, the method further comprises adsorbing the myxoma virus ex vivo onto a surface of the leukocyte. In some embodiments, the adsorbing the myxoma virus onto the surface of the leukocyte comprises exposing the leukocyte to the myxoma virus under conditions that permit binding of the myxoma virus to the surface of the leukocyte. In some embodiments, the myxoma virus is exposed to the leukocyte for at least five minutes. In some embodiments, the myxoma virus is exposed to the leukocyte for about one hour. In some embodiments, the myxoma virus is exposed to the leukocyte at a multiplicity of infection (MOI) of between about 0.001 and 1000. In some embodiments, the myxoma virus is exposed to the leukocyte at a multiplicity of infection (MOI) of between about 0.1 and 10. In some embodiments, the leukocyte is obtained from peripheral blood. In some embodiments, the leukocyte is obtained from bone marrow. In some embodiments, the leukocyte is a peripheral blood mononuclear cell. In some embodiments, the leukocyte is obtained from the subject. In some embodiments, the leukocyte is obtained from a donor that is HLA-matched, HLA-mismatched, haploidentical, or a combination thereof relative to the subject. In some embodiments, the one or more immunomodulatory transgenes comprise BiKE, LIGHT, Decorin, or a combination thereof. In some embodiments, the myxoma virus comprises MYXV-BiKE. In some embodiments, the BiKE binds to an antigen present on a natural killer cell, a neutrophil, or a combination thereof. In some embodiments, the BiKE binds to an antigen present on a hematologic cancer cell. In some embodiments, the BiKE binds to an antigen present on a myeloma cell, leukemia cell, or lymphoma cell. In some embodiments, the BiKE binds to CD16. In some embodiments, the BiKE binds CD138. In some embodiments, the BiKE comprises one or more single chain variable fragments (scFvs). In some embodiments, the BiKE comprises one or more humanized single chain variable fragments (scFvs). In some embodiments, the BiKE comprises a sequence that is at least 70% identical to any one of SEQ ID NOs: 6 or 16-31. In some embodiments, the BiKE is between the M135 and M136 open reading frames of the myxoma virus genome. In some embodiments, the myxoma virus comprises MYXV-huBiKE-GFP. In some embodiments, the myxoma virus comprises MYXV-LIGHT. In some embodiments, the LIGHT comprises a sequence from human LIGHT. In some embodiments, the LIGHT comprises a sequence that is at least 70% identical to any one of SEQ ID NOs: 13-15. In some embodiments, the LIGHT is between the M135 and M136 open reading frames of the myxoma virus genome. In some embodiments, the myxoma virus comprises MYXV-FLuc-huLIGHT-TdTomato. In some embodiments, the myxoma virus comprises MYXV-Decorin. In some embodiments, the Decorin comprises a sequence from human Decorin. In some embodiments, the Decorin comprises a sequence from mouse Decorin. In some embodiments, the Decorin comprises a sequence that is at least 70% identical to any one of SEQ ID NOs: 7-12. In some embodiments, the Decorin is between the M135 and M136 open reading frames of the myxoma virus genome. In some embodiments, the myxoma virus comprises MYXV-mDecorin-GFP. In some embodiments, the myxoma virus further comprises a reporter gene. In some embodiments, the reporter gene is a fluorescent protein. In some embodiments, the reporter gene is a luminescent substrate or enzyme. In some embodiments, the myxoma virus further comprises a deletion in the myxoma virus genome. In some embodiments, the myxoma virus comprises a deletion or disruption of one or more genes selected from the group consisting of M001R, M002R, M003.1R, M003.2R, M004.1R, M004R, M005R, M006R, M007R, M008.1R, M008R, M009L, M013, M036L, M063L, M11L, M128L, M131R, M135R, M136R, M141R, M148R, M151R, M152R, M153R, M154L, M156R, M-T2, M-T4, M-T5, M-T7, and SOD. In some embodiments, the myxoma virus comprises a deletion of M135. In some embodiments, the subject is a human subject. In some embodiments, the subject has or is suspected of having a cancer. In some embodiments the myxoma virus is capable of infecting cells that have a deficient innate anti-viral response. In some embodiments, the hematological cancer is a myeloma, leukemia, or lymphoma. In some embodiments, the hematological cancer is multiple myeloma. In some embodiments, the leukocyte is administered in a pharmaceutical composition. In some embodiments, the leukocyte is administered systemically. In some embodiments, the leukocyte is administered parenterally. In some embodiments, the leukocyte is administered by infusion.

BRIEF DESCRIPTION OF THE DRAWINGS

The novel features of certain embodiments of the disclosure are set forth with particularity in the appended claims.

A better understanding of the features and advantages of the present disclosure will be obtained by reference to the following detailed description that sets forth illustrative embodiments, in which the principles of the invention are utilized, and the accompanying drawings of which:

FIG. 1A is a schematic diagram of the MYXV genome and the insertion site of the cassettes expressing Decorin and eGFP. Both transgenes are expressed under a poxvirus synthetic early/late promoter (sE/L). FIG. 1B shows a PCR analysis of genomic viral DNA from MYXV-mDecorin-GFP clones using oligonucleotide primers to confirm presence of Decorin (panels 1-5) and FIG. 1C, proper insertion (Intergenic region M135-M1356). Lane 1 is DNA from MYXV-Lau, Lanes 2-6: MYXV-mDecorin-GFP clones, M represents known size DNA ladder. FIG. 1D shows a Western blot analysis of cell lysates and FIG. 1E, supernatants from MYXV-mDecorin-GFP infected RK13 cells 24 h post-infection. FIG. 1F shows the Luciferase activity in MLE/PAI/LUC cells following incubation with conditioned medium from RK13 cells infected with MYXV encoding decorin or GFP. FIG. 1G shows Single-step growth analysis of recombinant MYXV-Decorin vs MYXV-GFP.

FIGS. 2A-2F show the construction of MYXV-BiKE. FIG. 2A shows a scheme of the structure of the human CD138 targeted BiKE. FIG. 2B is a schematic diagram of the MYXV genome and the insertion site of the cassettes expressing BiKE and eGFP, both transgenes expressed under a poxvirus synthetic early/late promoter (sE/L). FIG. 2C shows a PCR analysis of genomic viral DNA from MYXV-BiKE clones using oligonucleotide primers to confirm presence of the BiKE cassette (panels 1-4) and FIG. 2D proper insertion (Intergenic region M135-M1356). Lane 1 is DNA from MYXV-Lau, Lanes 2-4: MYXV-BiKE clones, M represents known size DNA ladder. FIG. 2E shows a Western blot analysis of cell lysates and supernatants from MYXV-Decorin infected RK13 cells 24 hours post-infection. FIG. 2F shows a single-step growth analysis of recombinant MYXV-BIKE vs MYXV-GFP.

FIG. 6A shows infection (TdTomato+), viability (Near IR−), apoptosis (Annexin V+) and cell killing (Near IR+) of MM cells (CD138+) and of mock-treated (i.e., without adding MYXV) samples. FIG. 6B shows MYXV-FLuc-huLIGHT-TdTomato infection (TdTomato+) of CD138⁺ at three different MOI's. FIG. 6C shows apoptosis and cell death in CD138⁺ cells induced by MYXV-FLuc-huLIGHT-TdTomato.

FIG. 7A shows viability (Near IR−), apoptosis (Annexin V+) and cell killing (Near IR+) of uninfected MM cells (i.e., CD138⁺ TdTomato−) in mock-treated (i.e., without adding MYXV) sample, after 24 hours. The arrow indicates gating on TdTomato− cells. FIG. 7B shows the percentages of apoptosis and cell death in CD138⁺TdTomato− cells at 24-hours after virus treatment.

FIG. 8A shows infection (GFP+), viability (Near IR−), apoptosis (Annexin V+) and cell killing (Near IR+) of MM cells (CD138⁺) of mock-treated (i.e., without adding MYXV) sample. FIG. 8B shows MYXV-huBiKE-GFP infection of CD138⁺ at three different MOI's. FIG. 8C shows apoptosis and cell death in CD138⁺ cells induced by MYXV-huBiKE-GFP.

FIG. 9A shows viability (Near IR−), apoptosis (Annexin V+) and cell killing (Near IR+) of uninfected MM cells (i.e., CD138⁺GFP−) in mock-treated (i.e., without adding MYXV) sample, after 24 hours. The arrow indicates gating on GFP− cells. FIG. 9B shows the percentages of apoptosis and cell death of uninfected MM cells that are CD138⁺GFP− 24-hours post-infection.

FIG. 10A shows viability (Near IR−), infection (GFP+), apoptosis (Annexin V+), and cell killing (Near IR+) of MM cells (CD138*) after 24 hours of mock-treatment (i.e., without adding MYXV). FIG. 10B shows MYXV-huBiKE-GFP infection of CD138⁺ at three different MOI's. FIG. 10C shows apoptosis and cell death in CD138⁺ cells induced by MYXV-huBiKE-GFP. FIG. 10D shows fluorescence micrographs after 24-hours post-infection.

FIG. 11A shows viability (Near IR−), apoptosis (Annexin V+), and cell killing (Near IR+) of uninfected MM cells (i.e., CD138⁺GFP⁻) in mock-treated (i.e., without adding MYXV) sample, after 24 hours. The arrow indicates gating on GFP− (uninfected). FIG. 11B shows the percentages of apoptosis and cell death in uninfected CD138⁺GFP⁻ cells at 24-hours post-treatment with virus.

FIG. 12A shows infection (GFP+), apoptosis (Annexin V+), and cell killing (Near IR+) of MM cells (CD138⁺) after 24 hours of mock-treatment (i.e., without adding MYXV). FIG. 12B shows MYXV-mDecorin-GFP infection of CD138⁺ at three different MOI's. FIG. 12C shows viability, apoptosis and cell death in CD138⁺ cells induced by MYXV-mDecorin-GFP. FIG. 12D shows fluorescence micrographs after 24-hours post-infection.

FIG. 13A shows viability (Near IR−), apoptosis

7

Figure 13A:
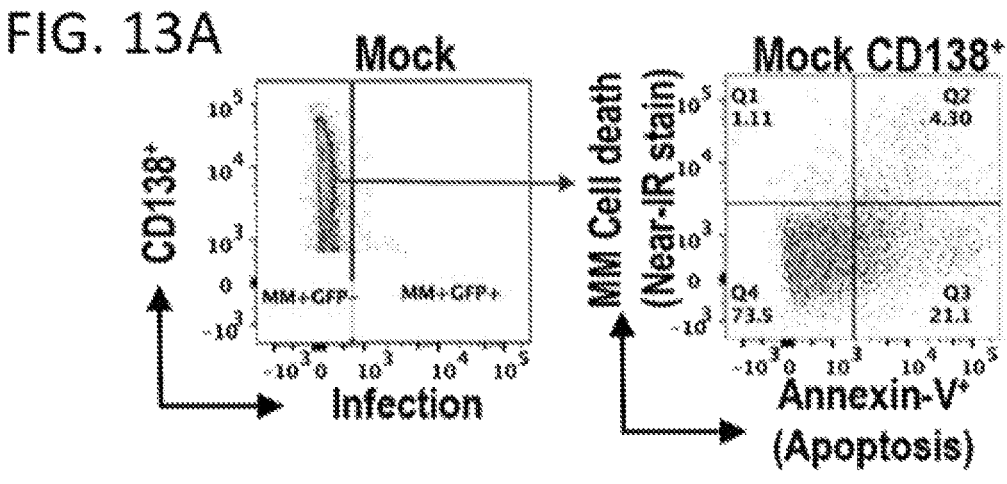
FIGS. 13A and 13B show killing of uninfected multiple myeloma (MM) cells (i.e., GFP⁻) from a primary human sample from patient #4 after treatment with MYXV-mDecorin-GFP.
Figure 13B:
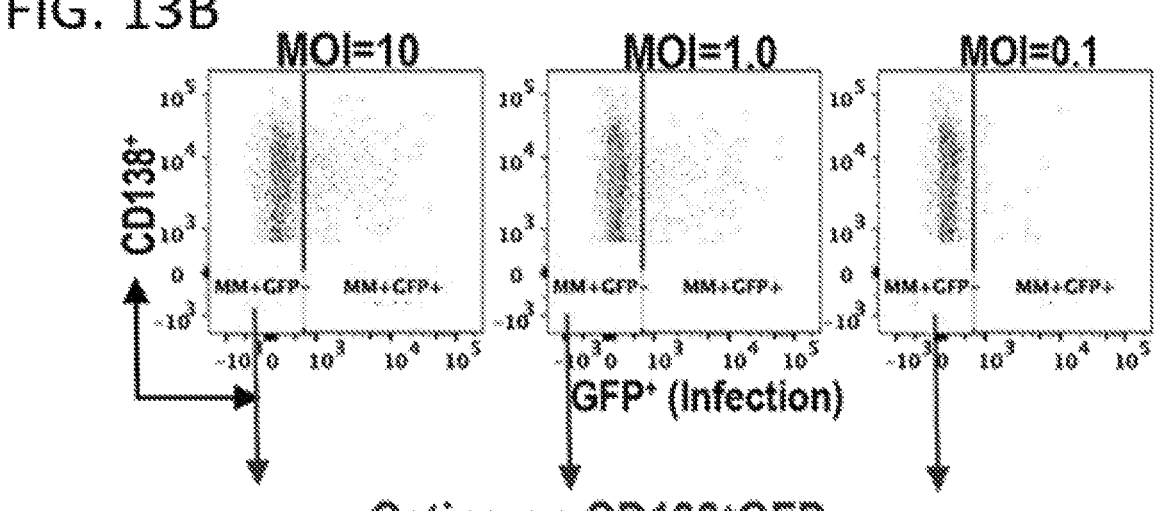
Figure 13B:
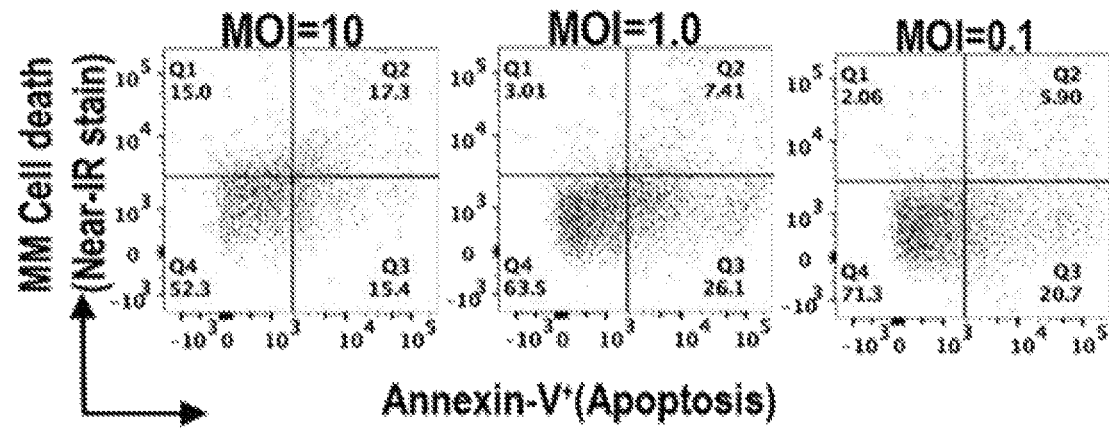

(Annexin V+) and cell killing (Near IR+) of uninfected MM cells (i.e., CD138$^+$GFP$^-$) in mock-treated (i.e., without adding MYXV) sample, 24 hours. The arrow indicates gating on GFP− (uninfected) cells. FIG. 13B shows the percentages of apoptosis and cell death in uninfected CD138$^+$GFP− cells after 24-hours post-infection.

Figure 14A:
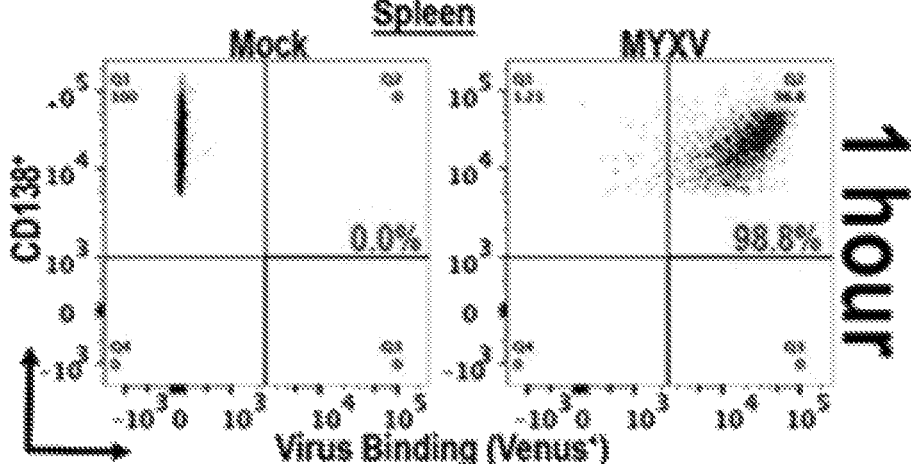
Figure 14B:
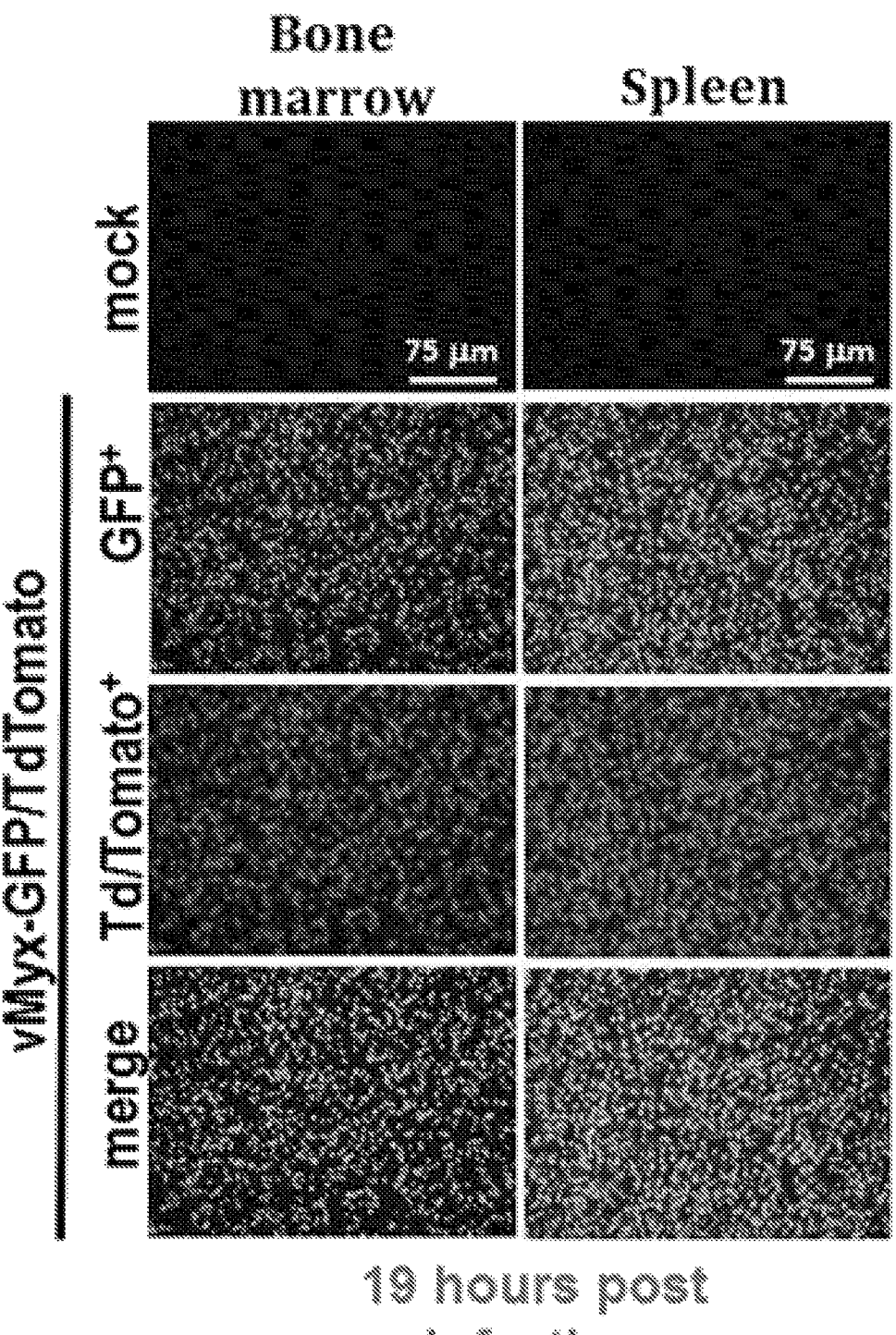
Figure 14C:
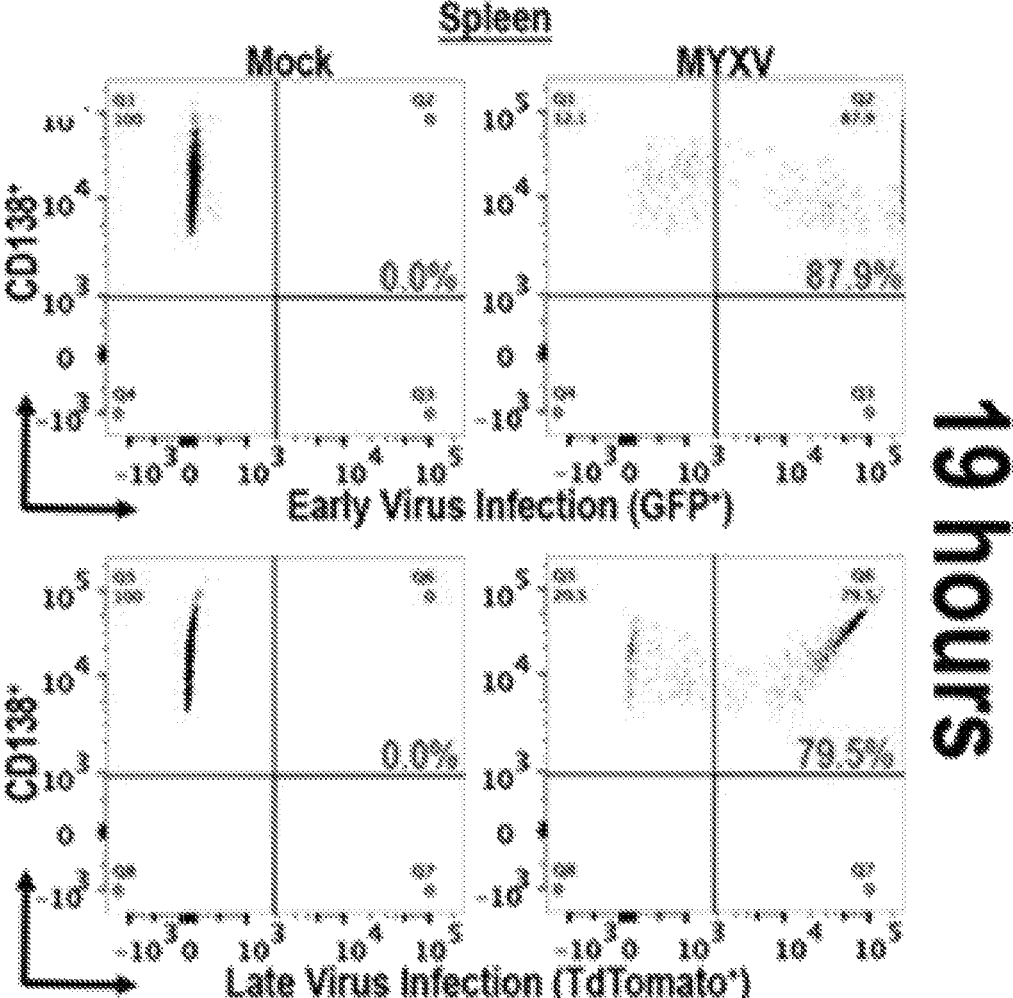

FIGS. 14A-14C show the BOR-resistant VK12598 cell line is susceptible to MYXV. FIG. 14A shows binding (Venus+) of MYXV to the VK12598 cell line. FIG. 14B shows productive infection of the VK12598 cell line via fluorescence microscopy. FIG. 14C shows productive infection of the VK12598 cell line via flow cytometry.

Figure 15A:
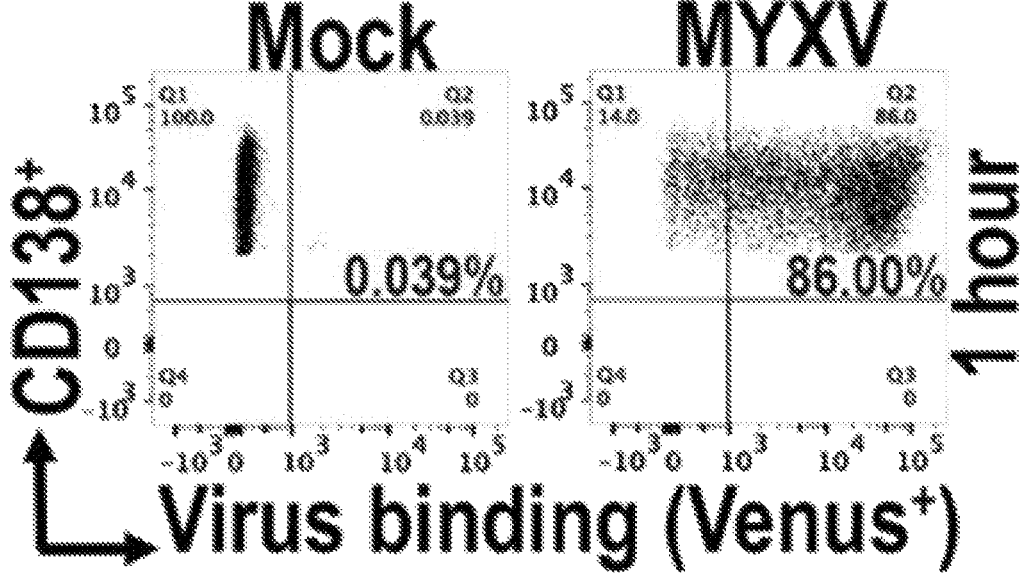
Figure 15A:
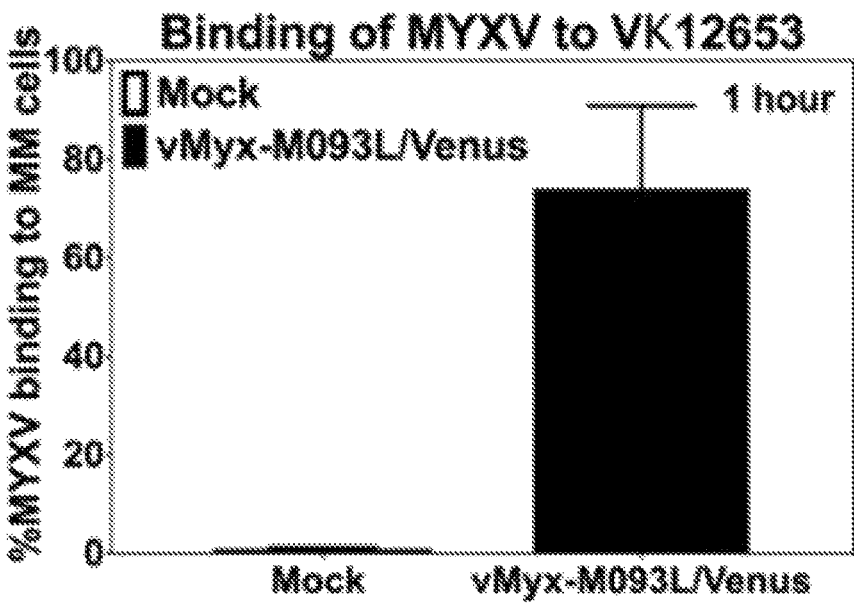
Figure 15B:
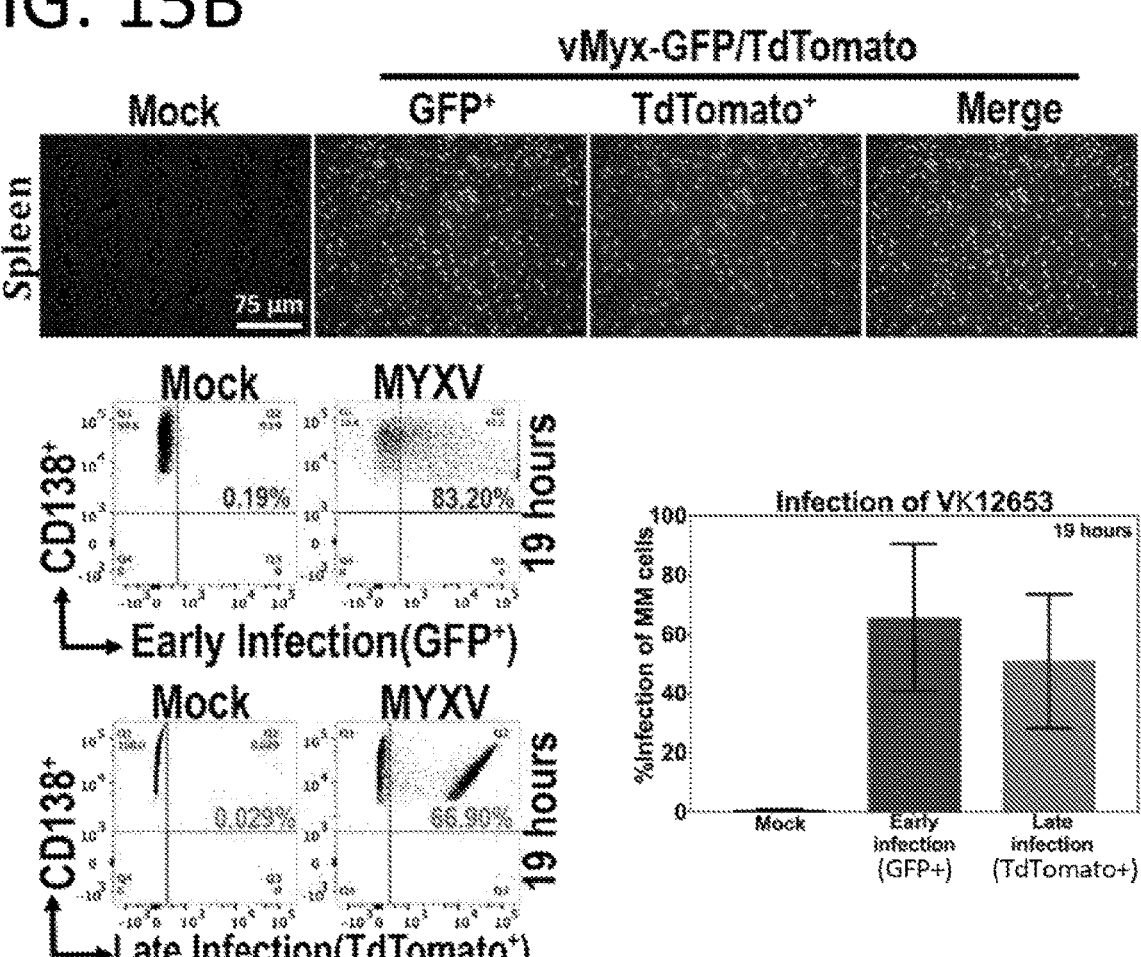

FIGS. 15A and 15B show MYXV binding and infection of the multi-drug resistant VK12653 cell line. FIG. 15A shows binding (Venus+) of MYXV to the VK12653 cell line. FIG. 15B shows productive infection of the VK12598 cell line via fluorescence microscopy and flow cytometry.

Figure 16A:
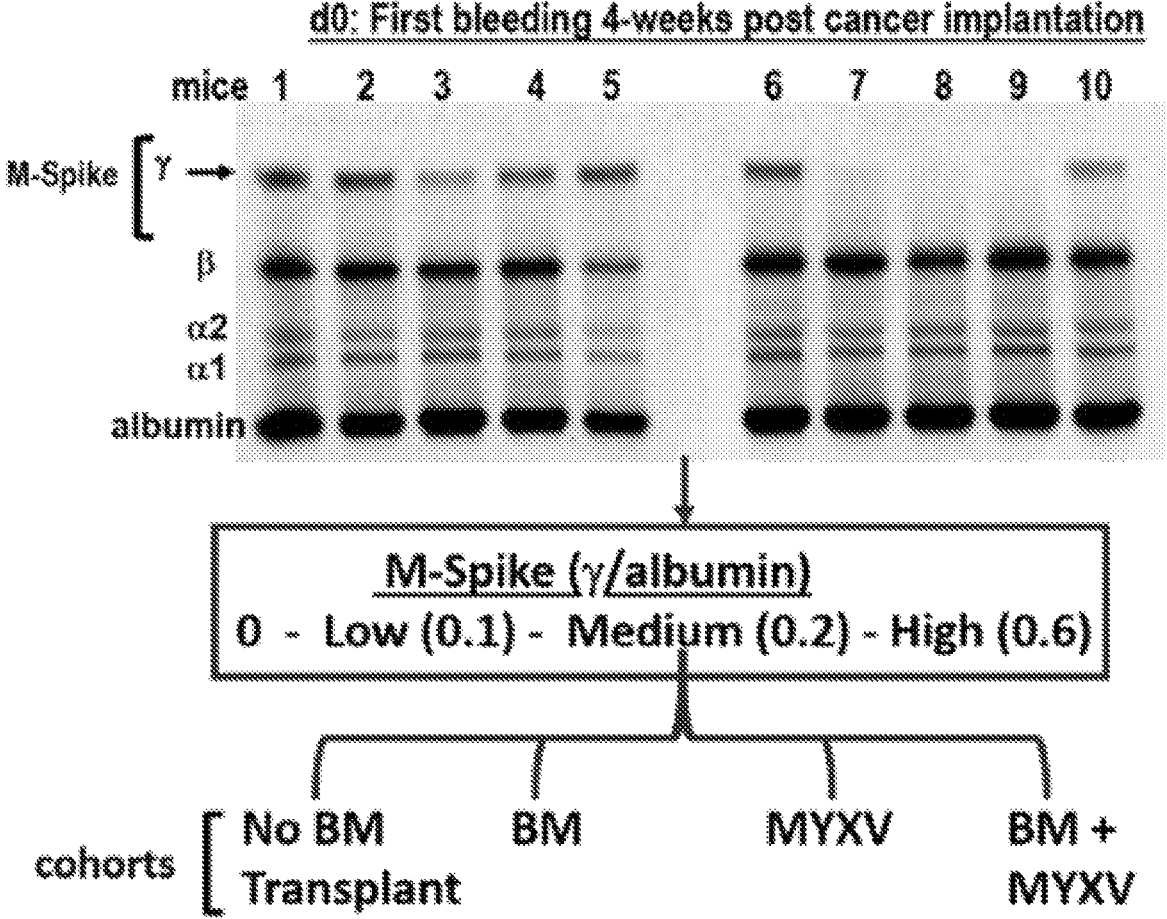
Figure 16B:
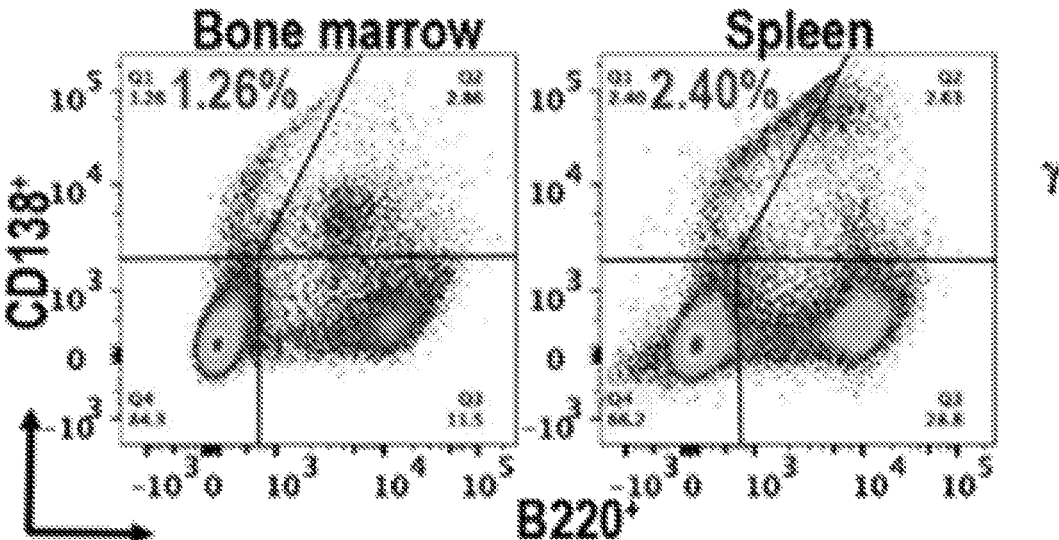
Figure 16B:
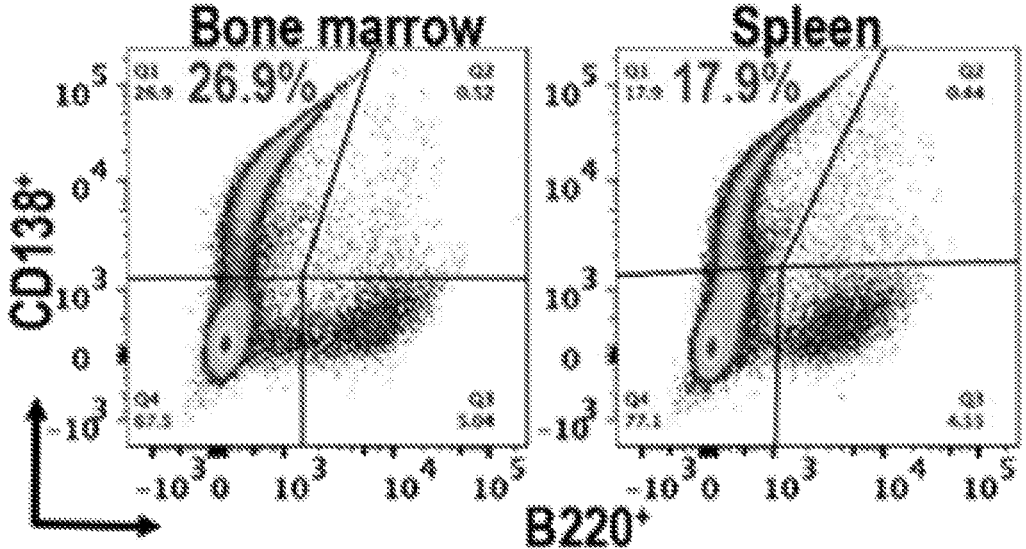
Figure 16C:
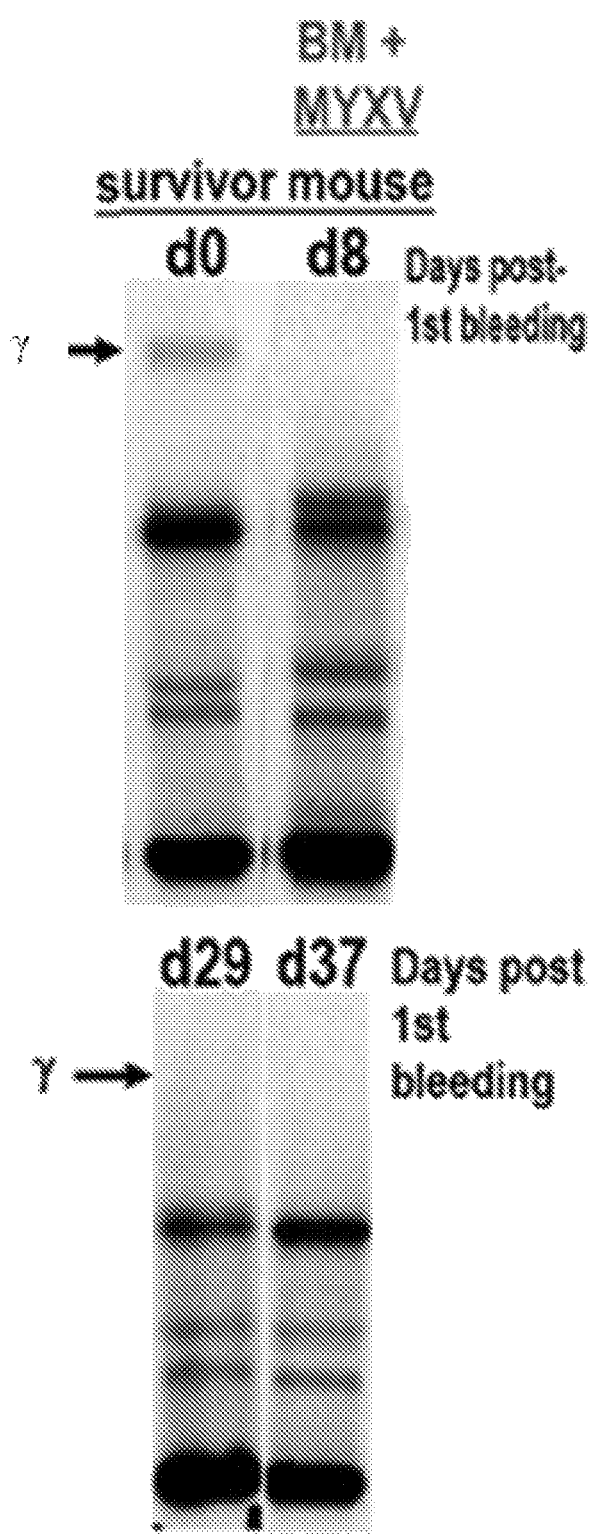

FIGS. 16A-16C show ex vivo therapy with myxoma virus to treat pre-existing multiple myeloma cancer in auto-transplant recipients. FIG. 16A shows a Western Blot providing the M-spike of mice four weeks post implantation with VK12598 cells (top panel) and four experimental cohorts (bottom panel). Levels of M-spike four weeks post-MM cell implantation. FIG. 16B shows the percentage of MM cells (CD138$^+$B220$^-$) in a representative mouse mock-treated mouse with low M-spike (0.1) and the percentage of MM (CD138$^+$B220$^-$) in a representative bone marrow-recipient mouse with high M-spike (0.6). FIG. 16C shows the M-spike of a mouse treated with bone marrow that had been ex vivo treated with MYXV-M135KO-GFP, with no M-spike band detected on day 8, day 29, and day 37 post-transplant.

DETAILED DESCRIPTION

Aspects of this disclosure relate to oncolytic virus recombinant constructs expressing immunomodulatory transgenes and their uses for treating cancer such as hematologic cancer. The oncolytic virus can be a Myxoma virus (MYXV), and the immunomodulatory transgenes used in the construct can include Decorin transgene, a BiKE (Bi-specific Natural Killer and Neutrophil engager) transgene, a LIGHT (corresponding to Lymphotoxins, exhibits Inducible expression, and competes with HSV Glycoprotein D for Herpesvirus entry mediator (HVEM), a receptor expressed by T lymphocytes) transgene, or a combination thereof. The MYXV described herein can be used to treat hematological cancers, including minimal residual disease (MRD) and drug-resistant MRD.

The MYXV described herein can be a more effective therapy to treat hematologic cancer such as relapsed Multiple Myeloma disease, and to fully eliminate the refractory and drug-resistant MRD. Take Multiple Myeloma (MM) for example, MM is a hematologic malignancy characterized by a clonal expansion of malignant plasma cells resulting in end organ damage, including lytic bone lesions, anemia, renal failure, or hypercalcemia (Han P. Recent advances in understanding multiple myeloma. Hematol Oncol Stem Cell Ther. 2017;In press). The bone marrow (BM) tumor microenvironment of MM plays a key role supporting and sustaining the differentiation, migration, proliferation, survival, and drug resistance of malignant MM cells (Kawano Y, Moschetta M, Manier S, Glavey S, Görgün G T, Roccaro A M, et al. Targeting the bone marrow microenvironment in multiple myeloma. *Immunol Rev.* 2015;263(1)). Autologous stem cell transplantation for transplant eligible patients, along with chemotherapy, is a standard treatment for MM (Landgren O, Lu S X, and Hultcrantz M. MRD Testing in Multiple Myeloma: The Main Future Driver for Modern Tailored Treatment. *Semin Hematol.* 2018; 55(1):44-50; Hoyos V, and I. B. The immunotherapy era of myeloma: monoclonal antibodies, vaccines, and adoptive T-cell therapies. *Blood.* 2016; 128(13):1679-87). However, a major hurdle of these therapies is the relapse of the disease due to neoplastic clones that can serve as a reservoir of therapy-resistant MM cells, resulting in minimal residual disease (MRD).

Despite improvement in outcomes, MM is still considered incurable for most patients, and poor survival rates are observed in those patients with high-risk features (Bustoros M, Mouhieddine T H, Detappe A, and IM. G. Established and Novel Prognostic Biomarkers in Multiple Myeloma. *Am Soc Clin Oncol Educ Book.* 2017; 37:548-60). Oncolytic viruses such as MYXV are mammalian viruses that can be designed and/or selected for their ability to selectively infect and kill transformed cancer cells, and for their ability to activate the host immune system. The MYXV described herein utilizes immunomodulatory transgenes and can work in combination with the host immune systems to target cancer cells. Therefore, the Myxoma virus described herein can help reduce or eliminate the refractory and drug-resistant minimal residual disease and can be more effective to treat relapsed MM disease.

Definitions

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. Although methods and materials similar or equivalent to those described herein can be used in the practice or testing of this disclosure, suitable methods and materials are described below. In addition, the materials, methods, and examples are illustrative only and not intended to be limiting.

The following explanations of terms and methods are provided to better describe the present compounds, compositions, and methods, and to guide those of ordinary skill in the art in the practice of the present disclosure. It is also to be understood that the terminology used in the disclosure is for the purpose of describing particular embodiments and examples only and is not intended to be limited.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" or "comprising" mean "includes." Hence "comprising A or B" means including A, B, or A and B. "Comprise" and variations of the term, such as "comprising", "comprises" and "comprised", as used herein, mean that various additional components or steps can be conjointly employed.

An "effective amount" or "therapeutically effective amount" refers to an amount of a compound or composition of this invention that is sufficient to produce a desired effect, which can be a therapeutic and/or beneficial effect. In this example, the effective amount can vary with the age, general condition of the subject, the severity of the condition being treated, the particular agent administered, the duration of the treatment, the nature of any concurrent treatment, the pharmaceutically acceptable carrier used, and like factors within the knowledge and expertise of skilled workers. As appropriate, an effective amount or therapeutically effective amount in any individual case can be determined by reference to the pertinent texts and literature and/or by experimentation. (See, for example, Remington, The Science and Practice of Pharmacy (latest edition)).

As used herein, the term "subject" and "patient" are used interchangeably and refer to both human and nonhuman animals. The term "nonhuman animals" of the disclosure includes all vertebrates, e.g., mammals and non-mammals, such as nonhuman primates, sheep, dog, cat, horse, cow, rodents (e.g., mice, rats, etc.) and the like. A subject can be a human. A subject can be a human patient. In some embodiments, the subject of this disclosure is a human subject.

The term "a cell" as used herein includes a single cell as well as a plurality or population of cells. Administering or exposing an agent to a cell can include in vitro, ev vivo, and in vivo administering or exposing.

A "subject in need thereof" or "a subject in need of" is a subject known to have, or is suspected of having a cancer, such as a hematological cancer.

As used herein, the term "cancer" refers to a malignant neoplasm, for example, a neoplasm that has undergone characteristic anaplasia with loss of differentiation, increased rate of growth, invasion of surrounding tissue, and is capable of metastasis.

Residual cancer is cancer that remains in a subject after any form of treatment given to the subject to reduce or eradicate cancer. Metastatic cancer is a cancer at one or more sites in the body, e.g., a second site, other than the site of origin of the original (primary) cancer from which the metastatic cancer is derived. Local recurrence is reoccurrence of the cancer at or near the same site (such as in the same tissue) as the original cancer. Hematologic cancer is a cancer that affects the blood, bone marrow, and/or lymphatic system.

Non-limiting examples of hematologic cancers include leukemia, lymphoma, and myeloma, such as: multiple myeloma (MM); active multiple myeloma; smoldering multiple myeloma; plasmacytoma; solitary plasmacytoma of the bone; extramedullary plasmacytoma; light chain myeloma; non-secretory myeloma; immunoglobulin G (IgG) myeloma; immunoglobulin A (IgA) myeloma; immunoglobulin M (IgM) myeloma; immunoglobulin D (IgD) myeloma; immunoglobulin E (IgE) myeloma; hyperdiploid multiple myeloma; non-hyperdiploid multiple myeloma; Hodgkin lymphoma; non-Hodgkin lymphoma; acute lymphoblastic leukemia; acute myeloid leukemia; essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts type 1; refractory anemia with excess blasts type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromes-unclassifiable; B lymphoblastic leukemial/lymphoma; T lymphoblastic leukemial/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/small lymphocytic lymphoma; B-cell prolymphocytic leukemia; lymphoplasmacytic lymphoma/Waldenstrom macroglobulinemia; Mantle cell lymphoma; marginal zone lymphomas; post-transplant lymphoproliferative disorders; HIV-associated lymphomas; primary effusion lymphoma; intravascular large B-cell lymphoma; primary cutaneous primary cutaneous B-cell lymphoma; hairy cell leukemia; monoclonal gammopathy of unknown significance; Anaplastic large cell lymphoma, Angioimmunoblastic T-cell lymphoma, Hepatosplenic T-cell lymphoma, B-cell lymphoma, reticuloendotheliosis, reticulosis, Mucosa-associated lymphatic tissue lymphoma, B-cell chronic lymphocytic leukemia, Waldenstrom's macroglobulinemia, Lymphomatoid granulomatosis, Nodular lymphocyte predominant Hodgkin's lymphoma, plasma cell leukemia, Acute erythraemia and erythroleukaemia, Acute erythremic myelosis, Acute erythroid leukemia, Heilmeyer-Schoner disease, Acute megakaryoblastic leukemia, Mast cell leukemia, Panmyelosis, Acute panmyelosis with myelofibrosis, Lymphosarcoma cell leukemia, Stem cell leukemia, Chronic leukaemia of unspecified cell type, Subacute leukaemia of unspecified cell type, Accelerated phase chronic myelogenous leukemia, Acute promyelocytic leukemia, Acute basophilic leukemia, Acute eosinophilic leukemia, Acute monocytic leukemia, Acute myeloblastic leukemia with maturation, Acute myeloid dendritic cell leukemia, Adult T-cell leukemia/lymphoma, Aggressive NK-cell leukemia, B-cell chronic lymphocytic leukemia, B-cell leukemia, Chronic myelogenous leukemia, Chronic idiopathic myelofibrosis, Kahler's disease, Myelomatosis, Solitary myeloma, Plasma cell leukemia, Angiocentric immunoproliferative lesion, Lymphoid granulomatosis, Angioimmunoblastic lymphadenopathy, T-gamma lymphoproliferative disease, Waldenstrom's macroglobulinaemia, Alpha heavy chain disease, Gamma heavy chain disease, and Franklin's disease. In some embodiments, the hematological cancer is multiple myeloma.

As used herein, the term "chemotherapeutic agent" refers to any chemical agent with therapeutic usefulness in the treatment of diseases characterized by abnormal cell growth. Such diseases can include tumors, neoplasms, and cancer, as well as diseases characterized by hyperplastic growth such as psoriasis. In some embodiments, a chemotherapeutic agent is an agent of use in treating cancer, such as an anti-neoplastic agent. In some embodiments, a chemotherapeutic agent is a radioactive compound. One of skill in the art can readily identify a chemotherapeutic agent of use (see for example, Slapak and Kufe, *Principles of Cancer Therapy*, Chapter 86 in *Harrison's Principles of Internal Medicine*, 14th edition; Perry et al., *Chemotherapy*, Ch. 17 in *Abeloff Clinical Oncology* 2nd ed., 2000 Churchill Livingstone, Inc; Baltzer and Berkery. (eds): *Oncology Pocket Guide to Chemotherapy*, 2nd ed. St. Louis, Mosby-Year Book, 1995; Fischer Knobf, and Durivage (eds): *The Cancer Chemotherapy Handbook*, 4th ed. St. Louis, Mosby-Year Book, 1993). Combination chemotherapy is the administration of more than one agent to treat cancer For example, a myxoma virus expressing an immunomodulatory transgene can be administered, and one or more chemotherapeutic agents can be administered, simultaneously or separated in time in any order.

"Treat," "treatment," or "treating," as used herein refers to administering a pharmaceutical composition to a patient suffering from a disease or condition. As used herein, the term "inhibiting or treating a disease," such as cancer, refers to delaying or inhibiting the development or progression of a disease or condition. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, such a metastasis, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology, for example metastatic cancer.

As used herein the "pharmaceutically acceptable carriers" useful in conjunction with therapeutic compounds disclosed herein can be conventional. *Remington's Pharmaceutical Sciences*, by E. W. Martin, Mack Publishing Co., Easton, Pa., 19th Edition (1995), describes compositions and formulations suitable for pharmaceutical delivery of therapeutic agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the terms "pharmaceutical" and "therapeutic agent" refer to a chemical compound or a composition capable of inducing a desired therapeutic or prophylactic effect when properly administered to a subject or a cell.

The term "replication-competent" as used herein refers to a virus, such as a myxoma virus, that is capable of infecting and replicating within a particular host cell, such as a human blood cell (e.g., peripheral blood mononuclear cell).

The term "immunomodulatory transgene" refers to a genetic sequence that can be introduced into a virus genome and encodes a product that can affect the function of the immune system, for example, that affects inflammation, innate or adaptive immune signaling, innate or adaptive immune cell activation (e.g., target cell killing, production of cytokines, chemokines, or other inflammatory mediators), innate or adaptive immune cell homing (e.g., chemotaxis, extravasation, and/or accumulation at a site), or innate or adaptive immune cell proliferation, innate or adaptive immune cell differentiation, antibody production, or a combination thereof. Examples of immunomodulatory transgenes include, but are not limited to, Decorin, BiKE, and LIGHT.

Myxoma Virus

Myxoma virus (MYXV) is potentially well suited as a therapeutic virus against blood cancers, like multiple myeloma (MM), because of its unique biology. MYXV is a member of the poxviridae family and the leporipoxvirus genus (Chan W M, Rahman M M, and McFadden G. Oncolytic myxoma virus: the path to clinic. *Vaccine*. 2013; 31(39):4252-8, Chan W M, and McFadden G. Oncolytic Poxviruses. *Annu Rev Virol*. 2014; 1(1):119-41).

MYXV is a novel oncolytic virus that can target a variety of human and murine cancers, both primary and established cell lines (Stanford M M, and McFadden G. Myxoma virus and oncolytic virotherapy: a new biologic weapon in the war against cancer. *Expert Opin Biol Ther*. 2007; 7(9):1415-11425; Wang G, Barrett J W, Stanford M, Werden S J, Johnston J B, Gao X, et al. Infection of human cancer cells with myxoma virus requires Akt activation via interaction with a viral ankyrin-repeat host range factor. *Proc Natl Acad Sci USA*. 2006; 103(12):4640-5; Bartee E, Chan W M, Moreb J S, Cogle C R, and McFadden G. Selective purging of human multiple myeloma cells from autologous stem cell transplantation grafts using oncolytic myxoma virus. *Biol Blood Marrow Transplant*. 2012; 18(10):1540-51; Chan W M, Rahman M M, and McFadden G. Oncolytic myxoma virus: the path to clinic. *Vaccine*. 2013; 31(39):4252-8; Kim M, Madlambayan G J, Rahman M M, Smallwood S E, Meacham A M, Hosaka K, et al. Myxoma virus targets primary human leukemic stem and progenitor cells while sparing normal hematopoitic stem and progenitor cells. *Leukemia*. 2009; 32:2313-7; Villa NY, Wasserfall C H, Meacham A M, Wise E, Chan W, Wingard J R, et al. Myxoma virus suppresses proliferation of activated T lymphocytes yet permits oncolytic virus transfer to cancer cells. *Blood*. 2015; 125(24):3778-88).

In nature, MYXV is exclusively rabbit-specific and does not cause infection or disease in humans, mice, or any other domestic animals. However, because of the nature of cancer pathway mutations associated with carcinogenesis, cancer cells from both mice and humans can exhibit a compromised ability to resist infection by some viruses, including MYXV (for example, compromised innate immune pathways) (Chan W M, and McFadden G. Oncolytic Poxviruses. *Annu Rev Virol*. 2014; 1(1):119-41, Sypula J, 'Wang F, Ma Y, Bell J, and McFadden G. Myxoma virus tropism in human tumors. *Gene Ther and Mol Biol*. 2004; 8:103-14).

Provided herein, in some embodiments, are modified myxoma viruses (MYXV). The MYXV may be any virus that belongs to the Leporipoxvirus species of poxviruses that is replication-competent. The MYXV may be a wild-type strain of MYXV or it may be a genetically modified strain of MYXV. In some instances, the MYXV is Lausanne strain. In some instances, the MYXV is a South American MYXV strain that circulates in *Sylvilagus brasiliensis*. In some instances, the MYXV is a Californian MYXV strain that circulates in *Sylvilagus bachmani*. In some instances, the MYXV is 6918, an attenuated Spanish field strain that comprises modifications in genes M009L, M036L, M135R, and M148R (GenBank Accession number EU552530 which is hereby incorporated by reference as provided by GenBank on Aug. 27, 2019). In some instances, the MYXV is 6918VP60-T2 (GenBank Accession Number EU552531 which is hereby incorporated by reference as provided by GenBank on Aug. 27, 2019). In some instances, the MYXV is SG33, a strain comprising a genomic deletion that affects genes M151R, M152R, M153R, M154L, M156R, M008.1R, M008R, M007R, M006R, M005R, M004.1R, M004R, M003.2R, M003.1R, M002R, and M001R, (Collection Nationale de Cultures de Microorganismes (CNCM) Accession No. 1-1594). In some instances, the MYXV is a strain termed the Standard laboratory Strain (SLS).

In some instances, the MYXV comprises at least 70%, 75%, 80%, 85%, 90%, 95%, 96%, 97%, 98%, or 99%, such as between 95% and 98%, 95% and 99%, including 90%, 91%, 92%, 93%, 94%, 95%, 96%, 97%, 98%, 99% sequence identity to a sequence disclosed in Cameron, et al., "The complete DNA sequence of Myxoma Virus," Virology 264: 298-318 (1999). In some cases, the MYXV comprises the sequence disclosed in Cameron, et al., "The complete DNA sequence of Myxoma Virus," Virology 264: 298-318 (1999).

The large and genetically stable poxvirus genome allows for genetic manipulation, for example, generation of viruses with one or more deletions and/or introduction of one or more therapeutic (e.g., immunomodulatory) transgenes (Nayerossadat N, Maedeh T, and Ali P A. Viral and nonviral delivery systems for gene delivery. *Adv Biomed Res.* 2012; 1:27).

Provided herein, in some embodiments, are myxoma viruses (MYXV) and modified MYXV. The MYXV may be any virus that belongs to the Leporipoxvirus species of pox viruses that is replication-competent. The MYXV may be a wild-type strain of MYXV or it may be a genetically modified strain of MYXV.

The Myxoma virus genome can be modified to express one or more therapeutic transgenes (e.g., immunomodulatory transgenes, such as BiKE, LIGHT, and/or Decorin) using molecular biology techniques known to a skilled person, and described for example in Sambrook et al. ((2001) Molecular Cloning: a Laboratory Manual, 3rd ed., Cold Spring Harbour Laboratory Press). A skilled person will be able to determine which portions of the Myxoma viral genome can be deleted such that the virus is still capable of productive infection, for example, to provide a replication competent virus. For example, non-essential regions of the viral genome that can be deleted can be deduced from comparing the published viral genome sequence with the genomes of other well-characterized viruses (see for example C. Cameron, S. Hota-Mitchell, L. Chen, J. Barrett, J.-X. Cao, C. Macaulay, D. Willer, D. Evans, and G. McFadden, Virology (1999) 264: 298-318)).

In some embodiments, the disclosed MYXV recombinant construct is an oncolytic viral candidate to treat relapsed/refractory primary human hematologic malignancies such as multiple myeloma (MM) and to target and reduce or eliminate minimal residual disease (MRD). In some embodiments, the MYXV comprises one or more transgenes.

In some embodiments, a MYXV of the disclosure comprises one or more gene modifications, deletions, and/or disruptions in the MYXV genome. For example, a MYXV of the disclosure can comprise one or more insertions, deletions, or substitutions within or adjacent to one or more genes in the genome. An insertion, deletion or modification can comprise a gene knockout (for example, deletion of one or more nucleotides that prevent functionality of the product encoded by the gene, or insertion of one or more nucleotides that disrupt expression and/or function of the product encoded by the gene). In some embodiments, an insertion, deletion, or modification does not comprise a gene knockout (for example, a sequence can be inserted at an intergenic locus between two genes, without disrupting expression of the two genes).

In some embodiments, a MYXV of the disclosure comprises one or more insertions, deletions, or substitutions within or adjacent to one or more genes associated with the ability of the virus to cause disease in a host animal. In some embodiments, a MYXV of the disclosure comprises one or more insertions, deletions, or substitutions within or adjacent to one or more genes associated with host cell tropism. In some embodiments, a MYXV of the disclosure comprises one or more insertions, deletions, or substitutions within or adjacent to one or more genes associated with the ability of the virus to evade an innate immune response.

In some embodiments, a MYXV of the disclosure comprises one or more insertions, deletions, or substitutions within or adjacent to one or more genes that modulate immune signaling in an infected cell (e.g., cytokine receptor signaling). In some embodiments, a MYXV of the disclosure comprises one or more insertions, deletions, or substitutions within or adjacent to one or more genes that modulate a cell death pathway in an infected cell (e.g., a gene that codes for a product that promotes or inhibits apoptosis, such as MOI IL). In some embodiments, a MYXV of the disclosure comprises one or more insertions, deletions, or substitutions within or adjacent to one or more genes that modulates viral replication in a cancer cell (e.g., increases or decreases the rate of viral replication in a cancer cell).

In some embodiments, the one or more genes associated with the ability of the virus to cause disease in a host animal, associated with host cell tropism, associated with the ability of the virus to evade an innate immune response, that can modulate immune signaling in an infected cell, that can modulate a cell death pathway in an infected cell, that can modulate viral replication in a cancer cell, or a combination thereof, comprise any one or more of M001R, M002R, M003.1R, M003.2R, M004.1R, M004R, M005R, M006R, M007R, M008.1R, M008R, M009L, M013, M036L, M063L, M11L, M128L, M131R, M135R, M136R, M141R, M148R, M151R, M152R, M153R, M154L, M156R, M-T2, M-T4, M-T5, M-T7, and SOD.

In some embodiments, a MYXV of the disclosure comprises a modification of a MYXV gene. In some instances, the modification is a deletion that impairs the function of a protein encoded by the MYXV gene. In some cases, the modification is a partial deletion (e.g., a 10%, 20%, 30%, 40%, 50%, 60%, 70%, 80%, 90%, or 95% deletion) of the MYXV gene. In other cases, the modification is a full deletion of the MYXV gene. In some embodiments, the modification is a replacement of the MYXV gene with one or more transgenes of the disclosure (e.g., BiKE, Decorin, and/or LIGHT).

In some embodiments, a MYXV of the disclosure comprises one or more insertions, deletions, or substitutions within or adjacent to one or more genes associated with host cell tropism (for example, rabbit cell tropism). In some embodiments, one or more genes associated with rabbit cell tropism comprises M11L, M063, M135R, M136R, M-T2, M-T4, M-T5, M-T7, or a combination thereof. In some instances, the one or more genes associated with rabbit cell tropism comprise M135R, M136R, or a combination thereof.

In some embodiments, a MYXV of the disclosure comprises a modification of the M135R gene. In some embodiments, the MYXV comprises a partial deletion or full deletion of M135R gene. A deletion or disruption of the M135R gene can, for example, attenuate the ability of a MYXV of the disclosure to cause disease in a host animal, without impairing the ability of the MYXV to exhibit an anti-cancer effect (e.g., infect and kill cancer cells). In some instances, the modification is a deletion that impairs the function of a protein encoded by the M135R gene. In some cases, the modification is a partial deletion (e.g., a 10%, 20%, 30%, 40%, 50%, 60%, 70%, 80%, 90%, or 95% deletion) of the M135R gene. In other cases, the modification is a full deletion of the M135R gene. In some embodiments, the MYXV comprises a modification of M135R gene that impairs the function of M135R gene (e.g., insertion of a sequence that disrupts the expression and/or function of the M135R gene). In some embodiments, a transgene of the disclosure replaces the M135R gene within the MYXV genome (for example, disrupts or replaces the M135R gene with one or more transgenes of the disclosure (e.g., BiKE, Decorin, and/or LIGHT)). In some embodiments, a transgene of the disclosure is inserted between M135R gene and M136R gene within the MYXV genome.

Transgenes

Provided herein, in some embodiments, are myxoma virus (MYXV) recombinant constructs comprising transgenes.

In the context of cancer and the tumor microenvironment, a range of immunomodulatory factors can affect the interplay between cancer cells and the immune system. For example, immunomodulatory factors can directly interact with malignant cells, positively or negatively affect infiltration of cytotoxic lymphocytes into the tumor microenvironment, positively or negatively affect the production of cytokines and chemokines that mediate immune responses against cancer cells, or a combination thereof. One or more immunomodulatory transgenes can be introduced into the MYXV genome, for example, to promote an immune response that more effectively treats or reduces a cancer.

For example, in some embodiments, one or more MYXV endogenous genes that regulate different forms of immune modulation and/or cell death are ablated. In some embodiments, one or more therapeutic immunomodulatory transgenes are introduced to the viral genome (e.g., to increase immunogenicity and/or induce preferred forms of cancer cell death). In some embodiments, one or more MYXV endogenous genes are ablated, and one or more immunomodulatory transgenes are introduced to the viral genome.

In some embodiments, the transgene is an immunomodulatory transgene. In some embodiments, a MYXV of the disclosure comprises a Decorin transgene, a BiKE (Bi-specific Natural Killer and Neutrophil engager) transgene, a LIGHT (corresponding to Lymphotoxins, exhibits Inducible expression, and competes with HSV Glycoprotein D for Herpesvirus entry mediator (HVEM), a receptor expressed by T lymphocytes) transgene, or a combination thereof.

A MYXV of the disclosure can comprise a Decorin transgene (MYXV-Decorin). Decorin is one example of an immunomodulatory transgene that can be introduced into the MYXV genome. Decorin is a small, leucine-rich proteoglycan that can exhibit tumor-suppressive properties. For example, decorin can bind and inhibit TGF-β, thereby alleviating immune suppression in the tumor microenvironment. Patients with MM produce low levels of decorin compared to healthy volunteers (Nemani N, Santo L, Eda H, Cirstea D, Mishima Y, Patel C, et al. Role of decorin in multiple myeloma (MM) bone marrow microenvironment. *J Bone Miner Res.* 2015; 30(3):465-70).

In some embodiments, a Decorin transgene comprises a sequence from a mammalian Decorin gene. In some embodiments, a Decorin transgene comprises a sequence from a mouse Decorin gene (mDecorin). In some embodiments, a Decorin transgene comprises a sequence from a human Decorin gene (huDecorin). In some embodiments, a Decorin transgene encodes a product that is secreted. In some embodiments, a Decorin transgene encodes a product that localizes to the cell surface (e.g., comprises a transmembrane domain). In some embodiments, a Decorin gene comprises a sequence from any one of SEQ ID NOs: 7-12, as provided in Table 1.

TABLE 1

| SEQ ID NO: | Description | Sequence |
|---|---|---|
| 7 | Human Decorin, isoform A | MKATIILLLLAQVSWAGPFQQRGLFDFMLEDEASGIGPEVPDDRDFEP SLGPVCPFRCQCHLRVVQCSDLGLDKVPKDLPPDTTLLDLQNNKITEI KDGDFKNLKNLHALILVNNKISKVSPGAFTPLVKLERLYLSKNQLKEL PEKMPKTLQELRAHENEITKVRKVTFNGLNQMIVIELGTNPLKSSGIE NGAFQGMKKLSYIRIADTNITSIPQGLPPSLTELHLDGNKISRVDAASL KGLNNLAKLGLSFNSISAVDNGSLANTPHLRELHLDNNKLTRVPGGL AEHKYIQVVYLHNNNISVVGSSDFCPPGHNTKKASYSGVSLFSNPVQ YWEIQPSTFRCVYVRSAIQLGNYK |
| 8 | Human Decorin, isoform B | MKATIILLLLAQVSWAGPFQQRGLFDFMLEDEASGIGPEVPDDRDFEP SLGPVCPFRCQCHLRVVQCSDLELGTNPLKSSGIENGAFQGMKKLSYI RIADTNITSIPQGLPPSLTELHLDGNKISRVDAASLKGLNNLAKLGLSF NSISAVDNGSLANTPHLRELHLDNNKLTRVPGGLAEHKYIQVVYLHN NNISVVGSSDFCPPGHNTKKASYSGVSLFSNPVQYWEIQPSTFRCVYV RSAIQLGNYK |
| 9 | Human Decorin, isoform C | MKATIILLLLAQVSWAGPFQQRGLFDFMLEDEASGIGPEVPDDRDFEP SLGPVCPFRCQCHLRVVQCSDLGLPPSLTELHLDGNKISRVDAASLKG LNNLAKLGLSFNSISAVDNGSLANTPHLRELHLDNNKLTRVPGGLAE HKYIQVVYLHNNNISVVGSSDFCPPGHNTKKASYSGVSLFSNPVQYW EIQPSTFRCVYVRSAIQLGNYK |
| 10 | Huma Decorin, isoform D | MKATIILLLLAQVSWAGPFQQRGLFDFMLEDEASGIGPEVPDDRDFEP SLGPVCPFRCQCHLRVVQCSDLGLDKVPKDLPPDTTLLDLQNNKITEI KDGDFKNLKNLHVVYLHNNNISVVGSSDFCPPGHNTKKASYSGVSLF SNPVQYWEIQPSTFRCVYVRSAIQLGNYK |

TABLE 1-continued

| SEQ ID NO: | Description | Sequence |
|---|---|---|
| 11 | Human Decorin, isoform E | MKATIILLLLAQVSWAGPFQQRGLFDFMLEDEASGIGPEVPDDRDFEP SLGPVCPFRCQCHLRVVQCSDLGCLPS |
| 12 | Mouse Decorin | MKATLIFFLLAQVSWAGPFEQRGLFDFMLEDEASGIIPYDPDNPLISM CPYRCQCHLRVVQCSDLGLDKVPWDFPPDTTLLDLQNNKITEIKEGA FKNLKDLHTLILVNNKISKISPEAFKPLVKLERLYLSKNQLKELPEKMP RTLQELRVHENEITKLRKSDFNGLNNVLVIELGGNPLKNSGIENGAFQ GLKSLSYIRISDTNITAIPQGLPTSLTEVHLDGNKITKVDAPSLKGLINL SKLGLSFNSITVMENGSLANVPHLRELHLDNNKLLRVPAGLAQHKYI QVVYLHNNNISAVGQNDFCRAGHPSRKASYSAVSLYGNPVRYWEIFP NTFRCVYVRSAIQLGNYK |

A MYXV of the disclosure can comprise a LIGHT transgene (MYXV-LIGHT). LIGHT (corresponding to Lymphotoxins, exhibits Inducible expression, and competes with HSV Glycoprotein D for Herpesvirus entry mediator (HVEM), a receptor expressed by T lymphocytes) is another example of an immunomodulatory transgene that can be introduced into the MYXV genome. LIGHT is a TNF superfamily member that can exhibit immune stimulatory activity, for example, LIGHT can promote T cell proliferation, chemotaxis, and secretion of Th1 cytokines. Expression of LIGHT in the tumor microenvironment can promote increased expression of chemokines, increased expression of adhesion molecules, and infiltration of T cells. Due to its immune stimulatory activity and widespread expression of its cognate receptor, HveA, LIGHT is a promising candidate molecule to stimulate anti-tumor immune responses.

In some embodiments, a LIGHT transgene comprises a sequence from a mammalian LIGHT gene. In some embodiments, a LIGHT transgene comprises a sequence from a mouse LIGHT gene (mLIGHT). In some embodiments, a LIGHT transgene comprises a sequence from a human LIGHT gene (huLIGHT). In some embodiments, a LIGHT transgene encodes a product that is secreted. In some embodiments, a LIGHT transgene encodes a product that localizes to the cell surface (e.g., comprises a transmembrane domain). In some embodiments, a LIGHT gene comprises a sequence from any one of SEQ ID NOs: 13-15, as provided in Table 2.

TABLE 2

| SEQ ID NO: | Description | Sequence |
|---|---|---|
| 13 | Human LIGHT/ TNFSF14, isoform 1 | MEESVVRPSVFVVDGQTDIPFTRLGRSHRRQSCSVARVGLGLLLLLM GAGLAVQGWFLLQLHWRLGEMVTRLPDGPAGSWEQLIQERRSHEVN PAAHLTGANSSLTGSGGPLLWETQLGLAFLRGLSYHDGALVVTKAG YYYIYSKVQLGGVGCPLGLASTITHGLYKRTPRYPEELELLVSQQSPC GRATSSSRVWWDSSFLGGVVHLEAGEKVVVRVLDERLVRLRDGTRS YFGAFMV |
| 14 | Human LIGHT/ TNFSF14, isoform 2 | MEESVVRPSVFVVDGQTDIPFTRLGRSHRRQSCSVARDGPAGSWEQLI QERRSHEVNPAAHLTGANSSLTGSGGPLLWETQLGLAFLRGLSYHDG ALVVTKAGYYYIYSKVQLGGVGCPLGLASTITHGLYKRTPRYPEELE LLVSQQSPCGRATSSSRVWWDSSFLGGVVHLEAGEKVVVRVLDERL VRLRDGTRSYFGAFMV |
| 15 | Mouse LIGHT/ TNFSF14 | MESVVQPSVFVVDGQTDIPFRRLEQNHRRRRCGTVQVSLALVLLLGA GLATQGWFLLRLHQRLGDIVAHLPDGGKGSWEKLIQDQRSHQANPA AHLTGANASLIGIGGPLLWETRLGLAFLRGLTYHDGALVTMEPGYYY VYSKVQLSGVGCPQGLANGLPITHGLYKRTSRYPKELELLVSRRSPCG RANSSRVWWDSSFLGGVVHLEAGEEVVVRVPGNRLVRPRDGTRSYF GAFMV |

A MYXV of the disclosure can comprise a BiKE transgene (MYXV-BiKE). In some embodiments, a BiKE transgene comprises a sequence derived from one or more antibodies (e.g., one or more heavy chain variable domains, one or more light chain variable domains, one or more complementarity determining regions (CDRs), or a combination thereof). In some embodiments, a BiKE transgene comprises a sequence derived from one or more mammalian antibodies. In some embodiments, a BiKE transgene comprises a sequence derived from one or more mouse antibodies. In some embodiments, a BiKE transgene comprises a sequence derived from one or more humanized antibodies (huBiKE). In some embodiments, a BiKE transgene encodes a product that is secreted. In some embodiments, a BiKE transgene encodes a product that localizes to the cell surface (e.g., comprises a transmembrane domain). In some embodiments, a BiKE gene comprises a sequence from any one or more of SEQ ID NOs: 16-31, as provided in Table 3. SEQ ID NOs: 16-17 provide the sequences of variable regions from an antibody specific for CD138. SEQ ID NOs: 18-19 provide the sequences of variable regions from an antibody specific for CD16. SEQ ID NOs: 20-25 provide the sequences of CDRs from antibodies specific for CD138, as identified by the method of Kabat. SEQ ID NOs: 26-31 provide the sequences of CDRs from antibodies specific for CD16, as identified by the method of Kabat.

TABLE 3

| SEQ ID NO: | Description | Sequence |
|---|---|---|
| 16 | Anti-CD138 VH | SQVQLQQSGSELMMPGASVKISCKATGYTFSNYWIEWVKQRP GHGLEWIGEILPGTGRTIYNEKFKGKATFTADISSNTVQMQLSS LTSEDSAVYYCARRDYYGNFYYAMDYWGQGTSVTVSS |
| 17 | Anti-CD138 VL | DIQMTQSTSSLSASLGDRVTISCSASQGINNYLNWYQQKPDGTV ELLIYYTSTLQSGVPSRFSGSGSGTDYSLTISNLEPEDIGTYYCQQ YSKLPRTFGGGTKLEIK |
| 18 | Anti-CD16 VH | QVTLKESGPGILQPSQTLSLTCSFSGFSLRTSGMGVGWIRQPSGK GLEWLAHIWWDDDKRYNPALKSRLTISKDTSSNQVFLKIASVD TADTATYYCAQINPAWFAYWGQGTLVTVSA |
| 19 | Anti-CD16 VL | DTVLTQSPASLAVSLGQRATISCKASQSVDFDGDSFMNWYQQK PGQPPKLLIYTTSNLESGIPARFSASGSGTDFTLNIHPVEEEDTAT YYCQQSNEDPYTFGGGTKLEIK |
| 20 | Anti-CD138 HCDR1 | NYWIE |
| 21 | Anti-CD138 HCDR2 | EILPGTGRTIYNEKFKG |
| 22 | Anti-CD138 HCDR3 | RDYYGNFYYAMDY |
| 23 | Anti-CD138 LCDR1 | SASQGINNYLN |
| 24 | Anti-CD138 LCDR2 | YTSTLQS |
| 25 | Anti-CD138 LCDR3 | QQYSKLPRT |
| 26 | Anti-CD16 HCDR1 | TSGMGVG |
| 27 | Anti-CD16 HCDR2 | HIWWDDDKRYNPALKS |
| 28 | Anti-CD16 HCDR3 | INPAWFAY |
| 29 | Anti-CD16 LCDR1 | KASQSVDFDGDSFMN |
| 30 | Anti-CD16 LCDR2 | TTSNLES |
| 31 | Anti-CD16 LCDR3 | QQSNEDPYT |

Bi-specific Natural Killer and Neutrophil engager (BiKE) (CD138-CD16) is another example of an immunomodulatory transgene that can be introduced into the MYXV genome. BiKE (CD138-CD16) can direct Natural Killer (NK) cells and neutrophils to attack tumor targets, for example, by binding CD16 on the surface of NK cells and neutrophils, and binding CD138 on the surface of MM cells. This can lead to NK/neutrophil activation, induction of target cancer cell apoptosis, and production of cytokines and chemokines in response to malignant targets (Gleason M K, Verneris M R, Todhunter D A, Zhang B, McCullar V, Zhou S X, et al. Bispecific and trispecific killer cell engagers directly activate human NK cells through CD16 signaling and induce cytotoxicity and cytokine production. *Mol Cancer Ther* 2012; 11(12):2674-84).

Disclosed herein, in some embodiments, are recombinant MYXV constructs that are armed with one or more of these immunomodulatory transgenes to target blood cancers, including MM. In this disclosure, MYXV expressing the transgenes BiKE, Decorin, or LIGHT are shown to selectively infect and kill primary human MM cells from patients with refractory disease that are resistant to standard therapies. In addition, it is demonstrated that these virus constructs can compromise MM cell viability by inducing apoptosis and death of MM cells. Notably, two kinds of MM cell killing can be observed: direct cytotoxic killing of virus-infected MM cells, plus "off-target" killing of un-infected MM cells. Without wishing to be bound by theory, killing of uninfected MM cells may be mediated by MYXV-activated immune cells resident in the patient samples.

A sequence of the disclosure can have at least 70% homology, at least 71% homology, at least 72% homology, at least 73% homology, at least 74% homology, at least 75% homology, at least 76% homology, at least 77% homology, at least 78% homology, at least 79% homology, at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, at least 99% homology, at least 99.1% homology, at least 99.2% homology, at least 99.3% homology, at least 99.4% homology, at least 99.5% homology, at least 99.6% homology, at least 99.7% homology, at least 99.8% homology, at least 99.9% homology, at least 99.91% homology, at least 99.92% homology, at least 99.93% homology, at least 99.94% homology, at least 99.95% homology, at least 99.96% homology, at least 99.97% homology, at least 99.98% homology, or at least 99.99% homology to an amino acid or nucleic acid sequence disclosed herein.

A transgene (e.g., a BiKE transgene) of the disclosure can encode an antigen-binding protein, for example, one or more variable regions or complementarity determining regions (CDRs) from an antibody. In some embodiments, a transgene (e.g., a BiKE transgene) of the disclosure comprises one or more single chain variable fragments (scFvs) derived from one or more antibodies. A scFv (single-chain variable fragment) is a fusion protein that can comprise the VH and VL domains of an antibody connected by a peptide linker. For example, a BiKE transgene can comprise two scFvs to allow binding of two targets.

Antigen binding proteins can be engineered based on antibody variable regions or CDRs. The variable (V) regions of an antibody mediate antigen binding and define the specificity of a particular antibody for an antigen. The variable region comprises relatively invariant sequences called framework regions, and hypervariable regions, which differ considerably in sequence among antibodies of different binding specificities. Within hypervariable regions are amino acid residues that primarily determine the binding specificity of the antibody. Sequences comprising these residues are known as complementarity determining regions (CDRs). One antigen binding site of an antibody comprises six CDRs, three in the hypervariable regions of the light chain, and three in the hypervariable regions of the heavy chain. The CDRs in the light chain are designated L1, L2, and L3, while the CDRs in the heavy chain are designated H1, H2, and H3. CDRs can also be designated LCDR1, LCDR2, LCDR3, HCDR1, HCDR2, and HCDR3, respectively. The contribution of each CDR to antigen binding varies among antibodies. CDRs can vary in length. For example, CDRs are often 5 to 14 residues in length, but CDRs as short as 0 residues or as long as 25 residues or longer exist. Several methods can be used to predict or designate CDR sequences, for example, the Kabat, Chothia, IMGT, paratome, Martin, and AHo methods. These CDR prediction methods can use different numbering systems, for example, because sequence insertions and deletions are numbered differently.

An antigen-binding protein can comprise a portion of an antibody, for example, the antigen-binding or variable region of the intact antibody. Non-limiting examples of antibody fragments include Fab, Fab', F(ab')2, dimers and trimers of Fab conjugates, Fv, scFv, minibodies, dia-, tria-, and tetrabodies, and linear antibodies. Fab and Fab' are antigen-binding fragments that can comprise the VH and CH1 domains of the heavy chain linked to the VL and CL domains of the light chain via a disulfide bond. A F(ab')2 can comprise two Fab or Fab' that are joined by disulfide bonds. A Fv can comprise the VH and VL domains held together by non-covalent interactions. A scFv (single-chain variable fragment) is a fusion protein that can comprise the VH and VL domains connected by a peptide linker. Manipulation of the orientation of the VH and VL domains and the linker length can be used to create different forms of molecules that can be monomeric, dimeric (diabody), trimeric (triabody), or tetrameric (tetrabody).

In some embodiments, a transgene of the disclosure can encode a linker sequence (e.g., a linker sequence between different domains of a protein encoded by the transgene). In some embodiments, a linker is used to join antibody variable regions to form an scFv. In some embodiments, a linker is used to join two scFvs to form a BiKE. A linker sequence can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues in length.

A flexible linker can have a sequence containing stretches of glycine and serine residues. The small size of the glycine and serine residues provides flexibility, and allows for mobility of the connected functional domains. The incorporation of serine or threonine can maintain the stability of the linker in aqueous solutions by forming hydrogen bonds with the water molecules, thereby reducing unfavorable interactions between the linker and protein moieties. Flexible linkers can also contain additional amino acids such as threonine and alanine to maintain flexibility, as well as polar amino acids such as lysine and glutamine to improve solubility. A rigid linker can have, for example, an alpha helix-structure. An alpha-helical rigid linker can act as a spacer between protein domains. A linker can comprise any of the sequences in Table 4, or repeats thereof. SEQ ID NOs: 32-37 provide flexible linkers. SEQ ID NOs: 38-41 provide rigid linkers.

TABLE 4

| SEQ ID NO: | Sequence |
| --- | --- |
| 32 | GGGGS |
| 33 | GGGS |
| 34 | GG |
| 35 | KESGSVSSEQLAQFRSLD |
| 36 | EGKSSGSGSESKST |
| 37 | GSAGSAAGSGEF |
| 38 | EAAAK |
| 39 | EAAAR |
| 40 | PAPAP |
| 41 | AEAAAKEAAAKA |

In some embodiments, a MYXV of the disclosure can comprise one or more additional transgenes (e.g., one or more transgenes in addition to one or more of Decorin, BiKE, and LIGHT).

In some embodiments, a MYXV of the disclosure can comprise one or more non-immunomodulatory transgenes (e.g., one or more non-immunomodulatory transgenes in addition to one or more of Decorin, BiKE, and LIGHT).

In some embodiments, a MYXV of the disclosure can comprise one or more reporter transgenes (e.g., one or more reporter transgenes in addition to one or more of Decorin, BiKE, and LIGHT). A reporter transgene (or reporter gene) can be used to monitor or quantify a MYXV in vitro, ex vivo, or in vivo. In some embodiments, a reporter transgene can be used to identify cells infected by an MYXV of the disclosure. For example, a MYXV of the disclosure can express a fluorescent transgene, and infected cells can be identified via fluorescence (e.g., fluorescence microscopy or flow cytometry). In some embodiments, a reporter transgene can be used to quantify cells infected by an MYXV of the disclosure. For example, a MYXV of the disclosure can express a fluorescent transgene, and infected cells can be quantified via fluorescence (e.g., quantification of the number or proportion of infected cells via fluorescence microscopy or flow cytometry). In some embodiments, a reporter transgene can be used to quantify viral replication or viral load in cells infected by an MYXV of the disclosure. For example, a MYXV of the disclosure can express a fluorescent transgene, and infected cells can be quantified via fluorescence (e.g., quantification of the average fluorescence intensity of cells via flow cytometry of fluorescence microscopy). In some embodiments, a MYXV of the disclosure can express a reporter gene that can be used for quantifying viral load or viral replication in vivo (e.g., imaging using an in vivo imaging system (IVIS)).

A reporter transgene of the disclosure can be expressed constitutively (e.g., under control of a constitutive promoter). A reporter transgene of the disclosure can be expressed conditionally (e.g., expressed under the control of a conditional promoter, e.g., a promoter that is only active or is more active in certain phases of a replication cycle).

Non-limiting examples of reporter transgenes include fluorescent proteins (e.g., green fluorescent protein (GFP), TdTomato, cyan fluorescent protein (CFP), yellow fluorescent protein (YFP), red fluorescent protein (RFP), Verde fluorescent protein (VFP), kindling fluorescent protein (KFP), mCherry, mTangerine, mRaspberry, mPlum, DsRed, etc.) and enzymes and substrates involved in luminescence (e.g., luciferin and/or luciferase).

In some embodiments, a MYXV of the disclosure does not comprise a reporter transgene (e.g., does not encode any fluorescent or luminescent proteins).

In addition to expression of one or more immunomodulatory transgenes, a MYXV of the disclosure can be modified to carry one or more other genes that can enhance the anticancer effect of the MYXV treatment. Such a gene may be a gene that is involved in triggering apoptosis, or is involved in targeting the infected cell for immune destruction, such as a gene that restores responsiveness of the cell to interferon, or that results in the expression of a cell surface marker that stimulates an antibody response, such as a bacterial cell surface antigen. A MYXV of the disclosure can be modified to express one or more genes involved in shutting off the neoplastic or cancer cell's proliferation and growth, thereby preventing or reducing division of the cancer cell. In some embodiments, a MYXV of the disclosure can be modified to include therapeutic genes, such as genes involved in the synthesis of chemotherapeutic agents. In some embodiments, a MYXV of the disclosure can comprise a transgene that increases viral replication in cells of a particular species (for example, increased replication in human cancer cells for increased killing and inhibition of human cancer cells).

Methods of Treatment

Provided herein, in some embodiments, are methods of treating a hematological cancer in a subject utilizing a myxoma virus (MYXV) of the disclosure. The hematological cancer can be a hematological cancer that comprises minimal residual disease (MRD) and/or drug-resistant MRD.

As disclosed in the Examples below, in vitro studies have demonstrated the ability of MYXV constructs of the disclosure to significantly eliminate refractory primary human multiple myeloma (MM) cells from patients who have failed standard therapies. Studies performed with MYXV have shown it can be a highly specific anti-cancer agent with a tropism for a number of human and murine cancer types.

Treatments of the disclosure (e.g., treatments utilizing MYXV-BiKE-, MYXV-LIGHT-, or MYXV-Decorin) can comprise a number of novel and advantageous aspects. For example, these virus constructs are so far the only described oncolytic viruses that selectively target and directly eliminate drug-resistant primary human MM cells that have been directly infected by each virus (e.g., CD138$^+$ cells that express a viral reporter gene, such as GFP$^+$ or TdTomato$^+$). In some embodiments, MYXV of the disclosure comprising transgenes can not only eliminate contaminating hematologic cancer cells by direct killing of virus-infected cells, but also can eliminate disease by enhanced "off-target" killing of uninfected cancer cells (e.g., via virus-activated immune cells). In some embodiments, MYXV of the disclosure comprising transgenes can elicit increased killing of uninfected cancer cells compared to other viruses (e.g., unarmed viruses or viruses lacking transgenes). In some embodiments, MYXV of the disclosure can exhibit enhanced "off-target" killing of uninfected MM cells (e.g., CD138$^+$ cells that are negative for a viral reporter gene, such as GFP$^-$ or TdTomato$^-$). Without wishing to be bound by any specific theory, virus-enhanced killing of uninfected cells may be mediated by MYXV-activated immune cells (e.g., immune cells activated by a transgene of the disclosure, other viral components, or a combination thereof).

The use of MYXV-BiKE, MYXV-LIGHT, or MYXV-Decorin to treat hematologic malignancies (e.g., refractory and/or minimal residual disease (MRD) of hematologic malignancies) can comprise multiple advantages over current therapies including chemotherapy and stem cell transplantation, and over other candidate oncolytic viruses. MYXV comprises a limited tropism that can, for example, allow the virus to infect human cancer cells, but not allow the virus to infect non-cancerous human cells. Unlike most viruses adapted from human pathogens, MYXV does not cause disease in humans, making it safe even for those patients with compromised immune systems. The lack of pre-existing anti-MYXV adaptive immunity in the human population can be advantageous, for example, allowing the virus to infect and kill cancer cells without being cleared as rapidly as a virus adapted from a human pathogen.

In ex vivo treatment approaches disclosed herein, incubation of MYXV with cells (e.g., bone marrow (BM) cells and/or peripheral blood mononuclear cells (PBMCs)) can be fast, for example, requiring only 1 hour of virus incubation ex vivo before re-infusion of the cells back into the cancer patient.

Thus, aspects of the present disclosure provide a method for inhibiting and/or treating a hematological cancer in a subject in need thereof. In certain embodiments, the method includes administering to a subject, such as a human subject, a MYXV of the disclosure that expresses one or more immunomodulatory transgenes, such as BiKE, LIGHT and/or Decorin, thereby treating and/or inhibiting the hematological cancer in the subject in need thereof. The subject can be a mammal. The subject can be a human.

In some embodiments, the MYXV comprises MYXV-LIGHT. In some embodiments, the MYXV comprises MYXV-Decorin. In some embodiments, the MYXV comprises MYXV-BiKE. In some embodiments, the MYXV comprises LIGHT and Decorin. In some embodiments, the MYXV comprises LIGHT and BiKE. In some embodiments, the MYXV comprises Decorin and BiKE. In some embodiments, the MYXV comprises LIGHT, Decorin, and BiKE. The LIGHT, Decorin, or BiKE can comprise sequences from a human, a mouse, a mammal, or a combination thereof, and can comprise any of the sequences disclosed herein.

In some embodiments, an MYXV of the disclosure comprises a reporter transgene (e.g., a fluorescent protein or a luminescent substrate or enzyme). In some embodiments, an MYXV of the disclosure comprises one or more of LIGHT, Decorin, and BiKE, and further comprises a reporter transgene.

In some embodiments, an MYXV of the disclosure comprises a modification, insertion, deletion, or disruption in one or more genes in the viral genome. For example, a MYXV of the disclosure can comprise a modification, insertion, deletion, or disruption in any one or more of the M001R, M002R, M003.1R, M003.2R, M004.1R, M004R, M005R, M006R, M007R, M008.1R, M008R, M009L, M013, M036L, M063L, M11L, M128L, M131R, M135R, M136R, M141R, M148R, M151R, M152R, M153R, M154L, M156R, M-T2, M-T4, M-T5, M-T7, and SOD genes. In some embodiments, a deletion or disruption of a viral gene in a MYXV of the disclosure can reduce the ability of the virus to cause disease in a host animal, modulate host cell tropism, reduce innate immune evasion in non-cancer cells, modulate immune signaling in infected cells, modulate a cell death pathway in infected cells, increase viral replication in a cancer cells, or a combination thereof.

In some embodiments, a MYXV of the disclosure comprises one or more insertions, deletions, or substitutions within or adjacent to one or more genes associated with host cell tropism (for example, rabbit cell tropism). In some embodiments, one or more genes associated with rabbit cell tropism comprises M11L, M063, M135R, M136R, M-T2, M-T4, M-T5, M-T7, or a combination thereof. In some instances, the one or more genes associated with rabbit cell tropism comprise M135R, M136R, or a combination thereof.

In some embodiments, a MYXV of the disclosure comprises a modification, insertion, deletion, or disruption in the M135R gene. In some embodiments, a MYXV of the disclosure comprises a deletion or disruption in the M135R gene. A deletion or disruption of the M135R gene can, for example, attenuate the ability of a MYXV of the disclosure to cause disease in a host animal, without impairing the ability of the MYXV to exhibit an anti-cancer effect (e.g., infect and kill cancer cells, elicit an anti-tumor immune response, or a combination thereof).

In some embodiments, the MYXV comprises MYXV-LIGHT, MYXV-BiKE, or MYXV-Decorin. In some embodiments, the MYXV comprises MYXV-FLuc-LIGHT-TdTomato, MYXV-BiKE-GFP, or MYXV-Decorin-GFP. In some embodiments, the MYXV comprises MYXV-FLuc-huLIGHT-TdTomato, MYXV-huBiKE-GFP, or MYXV-mDecorin-GFP. In some embodiments, the MYXV comprises MYXV-FLuc-huLIGHT, MYXV-huBiKE, or MYXV-mDecorin, i.e. the florescent reporter gene is omitted.

MYXV can infect cells (e.g., human cells) that have a deficient innate anti-viral response. Having "a deficient innate anti-viral response" as used herein can refer to a cell that, when exposed to a virus or when invaded by a virus, fails to induce one or more anti-viral defense mechanisms. For example, a deficient innate anti-viral response can comprise failure to inhibit viral replication, failure to produce an anti-viral cytokine (e.g., an interferon), failure to respond to an anti-viral cytokine (e.g., induce an interferon response pathway), failure to induce apoptosis, failure to trigger recognition via an innate immune receptor (e.g., pattern recognition receptor), or a combination thereof.

A deficient innate anti-viral response may be caused by various factors, for example, malignant transformation, mutation, infection, genetic defect, or environmental stress.

In some embodiments, a MYXV of the disclosure is not administered to a subject comprising a deficient innate anti-viral response caused by a genetic defect, environmental stress, or an infection (e.g., a pre-existing infection with a different pathogen).

In some embodiments, a MYXV of the disclosure is administered to a subject comprising a deficient innate anti-viral response caused by malignant transformation (e.g., a cancer). A cell comprising a deficient innate anti-viral response can be a cancer cell, e.g., a cancer cell that has a reduced or defective innate anti-viral response upon exposure to or infection by a virus as compared to a normal cell, for example, a non-cancer cell. This can include, for example, a cancer cell that is non-responsive to interferon (e.g., type I interferon), and/or a cancer cell that has a reduced or defective apoptotic response or induction of the apoptotic pathway. In some embodiments of the method, an MYXV of the disclosure is capable of infecting a cell that has a deficient innate anti-viral response. In some embodiments, the cell is a mammalian cancer cell. In some embodiments, the cell is a human cancer cell, e.g., a human hematological cancer cell.

In some embodiments, a MYXY of the disclosure is used to treat a cancer. The examples provided herein for multiple myeloma are, by extension, applicable to other hematological cancers. Types of cancer that may be treated according to the disclosed method include, but are not limited to, hematological cancers such as leukemia, lymphoma, and myeloma, for example: multiple myeloma (MM); active multiple myeloma; smoldering multiple myeloma; plasmacytoma; solitary plasmacytoma of the bone; extramedullary plasmacytoma; light chain myeloma; non-secretory myeloma; immunoglobulin G (IgG) myeloma; immunoglobulin A (IgA) myeloma; immunoglobulin M (IgM) myeloma; immunoglobulin D (IgD) myeloma; immunoglobulin E (IgE) myeloma; hyperdiploid multiple myeloma; non-hyperdiploid multiple myeloma; Hodgkin lymphoma; non-Hodgkin lymphoma; acute lymphoblastic leukemia; acute myeloid leukemia; essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts; type 1; refractory anemia with excess blasts; type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromes-unclassifiable; B lymphoblastic leukemia/lymphoma; T lymphoblastic leukemia/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/ small lymphocytic lymphoma; B-cell prolymphocytic leukemia; lymphoplasmacytic lymphoma/Waldenstrom macroglobulinemia; Mantle cell lymphoma; marginal zone lymphomas; post-transplant lymphoproliferative disorders; HIV-associated lymphomas; primary effusion lymphoma; intravascular large B-cell lymphoma; primary cutaneous primary cutaneous B-cell lymphoma; hairy cell leukemia; and monoclonal gammopathy of unknown significance; Anaplastic large cell lymphoma, Angioimmunoblastic T-cell lymphoma, Hepatosplenic T-cell lymphoma, B-cell lymphoma, reticuloendotheliosis, reticulosis, Mucosa-associated lymphatic tissue lymphoma, B-cell chronic lymphocytic leukemia, Waldenstrom's macroglobulinemia, Lymphomatoid granulomatosis, Nodular lymphocyte predominant Hodgkin's lymphoma, plasma cell leukemia, Acute erythraemia and erythroleukaemia, Acute erythremic myelosis, Acute erythroid leukemia, Heilmeyer-Schoner disease, Acute megakaryoblastic leukemia, Mast cell leukemia, Panmyelosis, Acute panmyelosis with myelofibrosis, Lymphosarcoma cell leukemia, Stem cell leukemia, Chronic leukaemia of unspecified cell type, Subacute leukaemia of unspecified cell type, Accelerated phase chronic myelogenous leukemia, Acute promyelocytic leukemia, Acute basophilic leukemia, Acute eosinophilic leukemia, Acute monocytic leukemia, Acute myeloblastic leukemia with maturation, Acute myeloid dendritic cell leukemia, Adult T-cell leukemia/lymphoma, Aggressive NK-cell leukemia, B-cell chronic lymphocytic leukemia, B-cell leukemia, Chronic myelogenous leukemia, Chronic idiopathic myelofibrosis, Kahler's disease, Myelomatosis, Solitary myeloma, Plasma cell leukemia, Angiocentric immunoproliferative lesion, Lymphoid granulomatosis, Angioimmunoblastic lymphadenopathy, T-gamma lymphoproliferative disease, Waldenstrom's macroglobulinaemia, Alpha heavy chain disease, Gamma heavy chain disease, and Franklin's disease. In some embodiments, the hematological cancer is multiple myeloma. In some embodiments, the cancer is a hematological cancer. In certain embodiments, the cancer comprises multiple myeloma.

Provided herein, in some embodiments, are methods of treating a hematological cancer (e.g., inhibiting, alleviating, stabilizing, reducing, or delaying progression of a hematological cancer). In some embodiments, the methods comprise administering a MYXV of the disclosure to a subject in need thereof to treat the hematological cancer. In some embodiments, the method further includes selecting a subject, such as a human subject, that has or is suspected of having a hematological cancer.

A MYXV of the disclosure can be administered in an amount effective to treat the hematological cancer. The amount may be sufficient to reduce the number of cancer cells in the subject (e.g., the concentration of the cancer cells in the subject's blood).

The effective amount to be administered to a subject can vary depending on many factors such as the pharmacodynamic properties of the MYXV, the modes of administration, the age, health and weight of the subject, the nature and extent of the disease state, the frequency of the treatment and the type of concurrent treatment, if any, and the virulence and titer of the virus.

The MYXV may be administered initially in a suitable amount that may be adjusted as required, depending on the clinical response of the subject. The effective amount of virus can be determined empirically and depends on the maximal amount of the MYXV that can be administered safely, and the minimal amount of the virus that produces the desired result.

To produce the same clinical effect when administering the virus systemically as that achieved through injection of the virus at the disease site, administration of significantly higher amounts of virus may be required. However, the appropriate dose level should be the minimum amount that would achieve the desired result.

The concentration of virus to be administered will vary depending on the virulence of the particular strain of MYXV that is to be administered and on the nature of the cells that are being targeted. In one embodiment, a dose of less than about $3 \times 10^{10}$ focus forming units ("ffu"), also called "infectious units", is administered to a human subject, in various embodiments, between about $10^2$ to about $10^9$ pfu, between about $10^2$ to about $10^7$ pfu, between about $10^3$ to about $10^6$ pfu, or between about $10^4$ to about $10^5$ pfu may be administered in a single dose.

In some embodiments, a subject is administered a certain dose of focus forming units (FFU) or plaque forming units (PFU) of a MYXV of the disclosure.

In some embodiments, the dose of MYXV administered to a subject is at least $1 \times 10^{\wedge}2$, $2 \times 10^{\wedge}2$, $3 \times 10^{\wedge}2$, $4 \times 10^{\wedge}2$, $5 \times 10^{\wedge}2$, $6 \times 10^{\wedge}2$, $7 \times 10^{\wedge}2$, $8 \times 10^{\wedge}2$, $9 \times 10^{\wedge}2$, $1 \times 10^{\wedge\wedge}3$, $2 \times 10^{\wedge\wedge}3$, $3 \times 10^{\wedge\wedge}3$, $4 \times 10^{\wedge\wedge}3$, $5 \times 10^{\wedge\wedge}3$, $6 \times 10^{\wedge\wedge}3$, $7 \times 10^{\wedge\wedge}3$, $8 \times 10^{\wedge\wedge}3$, $9 \times 10^{\wedge\wedge}3$, $1 \times 10^{\wedge\wedge}4$, $2 \times 10^{\wedge\wedge}4$, $3 \times 10^{\wedge\wedge}4$, $4 \times 10^{\wedge\wedge}4$, $5 \times 10^{\wedge\wedge}4$, $6 \times 10^{\wedge\wedge}4$, $7 \times 10^{\wedge\wedge}4$, $8 \times 10^{\wedge\wedge}4$, $9 \times 10^{\wedge\wedge}4$, $1 \times 10^{\wedge\wedge}5$, $2 \times 10^{\wedge\wedge}5$, $3 \times 10^{\wedge\wedge}5$, $4 \times 10^{\wedge\wedge}5$, $5 \times 10^{\wedge\wedge}5$, $6 \times 10^{\wedge\wedge}5$, $7 \times 10^{\wedge\wedge}5$, $8 \times 10^{\wedge\wedge}5$, $9 \times 10^{\wedge\wedge}5$, $1 \times 10^{\wedge\wedge}6$, $2 \times 10^{\wedge\wedge}6$, $3 \times 10^{\wedge\wedge}6$, $4 \times 10^{\wedge\wedge}6$, $5 \times 10^{\wedge\wedge}6$, $6 \times 10^{\wedge\wedge}6$, $7 \times 10^{\wedge\wedge}6$, $8 \times 10^{\wedge\wedge}6$, $9 \times 10^{\wedge\wedge}6$, $1 \times 10^{\wedge\wedge}7$, $2 \times 10^{\wedge\wedge}7$, $3 \times 10^{\wedge\wedge}7$, $4 \times 10^{\wedge\wedge}7$, $5 \times 10^{\wedge\wedge}7$, $6 \times 10^{\wedge\wedge}7$, $7 \times 10^{\wedge\wedge}7$, $8 \times 10^{\wedge\wedge}7$, $9 \times 10^{\wedge\wedge}7$, $1 \times 10^{\wedge\wedge}8$, $2 \times 10^{\wedge\wedge}8$, $3 \times 10^{\wedge\wedge}8$, $4 \times 10^{\wedge\wedge}8$, $5 \times 10^{\wedge\wedge}8$, $6 \times 10^{\wedge\wedge}8$, $7 \times 10^{\wedge\wedge}8$, $8 \times 10^{\wedge\wedge}8$, $9 \times 10^{\wedge\wedge}8$, $1 \times 10^{\wedge\wedge}9$, $2 \times 10^{\wedge\wedge}9$, $3 \times 10^{\wedge\wedge}9$, $4 \times 10^{\wedge\wedge}9$, $5 \times 10^{\wedge\wedge}9$, $6 \times 10^{\wedge\wedge}9$, $7 \times 10^{\wedge\wedge}9$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, $1\times10^{16}$, $2\times10^{16}$, $3\times10^{16}$, $4\times10^{16}$, $5\times10^{16}$, $6\times10^{16}$, $7\times10^{16}$, $8\times10^{16}$, $9\times10^{16}$, $1\times10^{17}$, $2\times10^{17}$, $3\times10^{17}$, $4\times10^{17}$, $5\times10^{17}$, $6\times10^{17}$, $7\times10^{17}$, $8\times10^{17}$, $9\times10^{17}$, $1\times10^{18}$, $2\times10^{18}$, $3\times10^{18}$, $4\times10^{18}$, $5\times10^{18}$, $6\times10^{18}$, $7\times10^{18}$, $8\times10^{18}$, $9\times10^{18}$, $1\times10^{19}$, $2\times10^{19}$, $3\times10^{19}$, $4\times10^{19}$, $5\times10^{19}$, $6\times10^{19}$, $7\times10^{19}$, $8\times10^{19}$, $9\times10^{19}$, $1\times10^{20}$, $2\times10^{20}$, $3\times10^{20}$, $4\times10^{20}$, $5\times10^{20}$, $6\times10^{20}$, $7\times10^{20}$, $8\times10^{20}$, or $9\times10^{20}$ FFU or PFU of a MYXV of the disclosure.

In some embodiments, the dose of MYXV administered to a subject is at most $1\times10^{2}$, $2\times10^{2}$, $3\times10^{2}$, $4\times10^{2}$, $5\times10^{2}$, $6\times10^{2}$, $7\times10^{2}$, $8\times10^{2}$, $9\times10^{2}$, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, $1\times10^{16}$, $2\times10^{16}$, $3\times10^{16}$, $4\times10^{16}$, $5\times10^{16}$, $6\times10^{16}$, $7\times10^{16}$, $8\times10^{16}$, $9\times10^{16}$, $1\times10^{17}$, $2\times10^{17}$, $3\times10^{17}$, $4\times10^{17}$, $5\times10^{17}$, $6\times10^{17}$, $7\times10^{17}$, $8\times10^{17}$, $9\times10^{17}$, $1\times10^{18}$, $2\times10^{18}$, $3\times10^{18}$, $4\times10^{18}$, $5\times10^{18}$, $6\times10^{18}$, $7\times10^{18}$, $8\times10^{18}$, $9\times10^{18}$, $1\times10^{19}$, $2\times10^{19}$, $3\times10^{19}$, $4\times10^{19}$, $5\times10^{19}$, $6\times10^{19}$, $7\times10^{19}$, $8\times10^{19}$, $9\times10^{19}$, $1\times10^{20}$, $2\times10^{20}$, $3\times10^{20}$, $4\times10^{20}$, $5\times10^{20}$, $6\times10^{20}$, $7\times10^{20}$, $8\times10^{20}$, or $9\times10^{20}$ FFU or PFU of a MYXV of the disclosure.

In some embodiments, a subject is administered a certain dose of focus forming units (FFU) or plaque forming units (PFU) of a MYXV of the disclosure per kilogram of body weight.

In some embodiments, the dose of MYXV administered to a subject is at least $1\times10^{2}$, $2\times10^{2}$, $3\times10^{2}$, $4\times10^{2}$, $5\times10^{2}$, $6\times10^{2}$, $7\times10^{2}$, $8\times10^{2}$, $9\times10^{2}$, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, $1\times10^{16}$, $2\times10^{16}$, $3\times10^{16}$, $4\times10^{16}$, $5\times10^{16}$, $6\times10^{16}$, $7\times10^{16}$, $8\times10^{16}$, $9\times10^{16}$, $1\times10^{17}$, $2\times10^{17}$, $3\times10^{17}$, $4\times10^{17}$, $5\times10^{17}$, $6\times10^{17}$, $7\times10^{17}$, $8\times10^{17}$, $9\times10^{17}$, $1\times10^{18}$, $2\times10^{18}$, $3\times10^{18}$, $4\times10^{18}$, $5\times10^{18}$, $6\times10^{18}$, $7\times10^{18}$, $8\times10^{18}$, $9\times10^{18}$, $1\times10^{19}$, $2\times10^{19}$, $3\times10^{19}$, $4\times10^{19}$, $5\times10^{19}$, $6\times10^{19}$, $7\times10^{19}$, $8\times10^{19}$, $9\times10^{19}$, $1\times10^{20}$, $2\times10^{20}$, $3\times10^{20}$, $4\times10^{20}$, $5\times10^{20}$, $6\times10^{20}$, $7\times10^{20}$, $8\times10^{20}$, or $9\times10^{20}$ FFU or PFU of a MYXV of the disclosure per kilogram of body weight of the subject.

In some embodiments, the dose of MYXV administered to a subject is at most $1\times10^{2}$, $2\times10^{2}$, $3\times10^{2}$, $4\times10^{2}$, $5\times10^{2}$, $6\times10^{2}$, $7\times10^{2}$, $8\times10^{2}$, $9\times10^{2}$, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, $1\times10^{16}$, $2\times10^{16}$, $3\times10^{16}$, $4\times10^{16}$, $5\times10^{16}$, $6\times10^{16}$, $7\times10^{16}$, $8\times10^{16}$, $9\times10^{16}$, $1\times10^{17}$, $2\times10^{17}$, $3\times10^{17}$, $4\times10^{17}$, $5\times10^{17}$, $6\times10^{17}$, $7\times10^{17}$, $8\times10^{17}$, $9\times10^{17}$, $1\times10^{18}$, $2\times10^{18}$, $3\times10^{18}$, $4\times10^{18}$, $5\times10^{18}$, $6\times10^{18}$, $7\times10^{18}$, $8\times10^{18}$, $9\times10^{18}$, $1\times10^{19}$, $2\times10^{19}$, $3\times10^{19}$, $4\times10^{19}$, $5\times10^{19}$, $6\times10^{19}$, $7\times10^{19}$, $8\times10^{19}$, $9\times10^{19}$, $1\times10^{20}$, $2\times10^{20}$, $3\times10^{20}$, $4\times10^{20}$, $5\times10^{20}$, $6\times10^{20}$, $7\times10^{20}$, $8\times10^{20}$, or $9\times10^{20}$ FFU or PFU of a MYXV of the disclosure per kilogram of body weight of the subject.

A MYXV of the disclosure can be administered at any interval desired. In some embodiments, the MYXV can be administered hourly. In some embodiments, the MYXV can be administered about every 1, 2, 3, 4, 5, 6, 7, 8, 9, 10, 11, 12, 13, 14, 15, 16, 18, 20, 22, 24, 26, 28, 30, 32, 36, 40, 44, or 48 hours. In some embodiments, the MYXV can be administered twice a day, once a day, five times a week, four times a week, three times a week, two times a week, once a week, once every two weeks, once every three weeks, once every four weeks, once a month, once every five weeks, once every six weeks, once every eight weeks, once every two months, once every twelve weeks, once every three months, once every four months, once every six months, once a year, or less frequently.

A MYXV of the disclosure can be administered to a subject in a therapeutically-effective amount by various forms and routes including, for example, systemic, oral, topical, parenteral, intravenous injection, intravenous infusion, intratumoral injection, subcutaneous injection, intramuscular injection, intradermal injection, intraperitoneal injection, intracerebral injection, subarachnoid injection, intraspinal injection, intrasternal injection, intraarticular injection, endothelial administration, local administration, intranasal administration, intrapulmonary administration, intraarterial administration, intrathecal administration, inhalation, intralesional administration, intradermal administration, epidural administration, absorption through epithelial or mucocutaneous linings (e.g., oral mucosa, rectal and intestinal mucosa), intracapsular administration, subcapsular administration, intracardiac administration, transtracheal administration, subcuticular administration, subarachnoid administration, subcapsular administration, intraspinal administration, or intrasternal administration.

In some embodiments, the virus is administered systemically. In some embodiments, the virus is administered by injection at a disease site. In some embodiments, the virus is administered orally. In some embodiments, the virus is administered parenterally.

A MYXV of the disclosure (e.g., expressing one or more immunomodulatory transgenes, such as BiKE, LIGHT and/or Decorin), can be administered as a sole therapy or can be administered in combination with one or more other therapies. In some embodiments, a MYXV of the disclosure is administered in combination with a chemotherapy, an immunotherapy, a cell therapy, a radiation therapy, a stem cell transplant (such as an autologous stem cell transplant), or a combination thereof. For example, the MYXV expressing one or more immunomodulatory transgenes, such as BiKE, LIGHT and/or Decorin may be administered either prior to or following another treatment, such as administration of radiotherapy or conventional chemotherapeutic drugs and/or a stem cell transplant, such as an autologous stem cell transplant or an allogenic stem cell transplant (e.g., a HLA-matched, HLA-mismatched, or haploidentical transplant).

In some embodiments, a MYXV of the disclosure can be in combination with an immune checkpoint modulator. Examples of immune checkpoint modulators include, but are not limited to, PD-L1 inhibitors such as durvalumab (Imfinzi) from AstraZeneca, atezolizumab (MPDL3280A) from Genentech, avelumab from EMD Serono/Pfizer, CX-072 from CytomX Therapeutics, FAZ053 from Novartis Pharmaceuticals, KN035 from 3D Medicine/Alphamab, LY3300054 from Eli Lilly, or M7824 (anti-PD-L1/TGFbeta trap) from EMD Serono; PD-L2 inhibitors such as GlaxoSmithKline's AMP-224 (Amplimmune), and rHIgM12B7; PD-1 inhibitors such as nivolumab (Opdivo) from Bristol-Myers Squibb, pembrolizumab (Keytruda) from Merck, AGEN 2034 from Agenus, BGB-A317 from BeiGene, B1-754091 from Boehringer-Ingelheim Pharmaceuticals, CBT-501 (genolimzumab) from CBT Pharmaceuticals, INCSHR1210 from Incyte, JNJ-63723283 from Janssen Research & Development, MEDI0680 from MedImmune, MGA 012 from MacroGenics, PDR001 from Novartis Pharmaceuticals, PF-06801591 from Pfizer, REGN2810 (SAR439684) from Regeneron Pharmaceuticals/Sanofi, or TSR-042 from TESARO; CTLA-4 inhibitors such as ipilimumab (also known as Yervoy®, MDX-010, BMS-734016 and MDX-101) from Bristol Meyers Squibb, tremelimumab (CP-675,206, ticilimumab) from Pfizer, or AGEN 1884 from Agenus; LAG3 inhibitors such as BMS-986016 from Bristol-Myers Squibb, IMP701 from Novartis Pharmaceuticals, LAG525 from Novartis Pharmaceuticals, or REGN3767 from Regeneron Pharmaceuticals; B7-H3 inhibitors such as enoblituzumab (MGA271) from MacroGenics; KIR inhibitors such as Lirilumab (IPH2101; BMS-986015) from Innate Pharma; CD137 inhibitors such as urelumab (BMS-663513, Bristol-Myers Squibb), PF-05082566 (anti-4-1BB, PF-2566, Pfizer), or XmAb-5592 (Xencor); and PS inhibitors such as Bavituximab. In some embodiments, the MYXV is combined with an antibody or antigen-binding fragment thereof, an RNAi molecule, or a small molecule, that acts on or is specific for, for example, TIM3, CD52, CD30, CD20, CD33, CD27, OX40, GITR, ICOS, BTLA (CD272), CD160, 2B4, LAIRI, TIGHT, LIGHT, DR3, CD226, CD2, or SLAM.

An MYXV of the disclosure can be prepared using standard techniques. For example, the virus may be prepared by infecting cultured rabbit cells, or immortalized permissive human or primate cells, with the MYXV strain that is to be used, allowing the infection to progress such that the virus replicates in the cultured cells and can be released by standard methods for disrupting the cell surface and thereby releasing the virus particles for harvesting. Once harvested, the virus titer may be determined, for example, by infecting a confluent lawn of rabbit cells and performing a plaque assay (see Mossman et al. (1996) Virology 215:17-30 which is hereby incorporated by reference in its entirety).

Cellular Delivery of MYXV

Further disclosed herein, in some embodiments, is a novel delivery strategy where a MYXV of the disclosure is first adsorbed to cells, and the cells are administered to a subject. This method can deliver a MYXV of the disclosure to sites of disease via virus-bearing "carrier" cells. In some embodiments, this cell-assisted delivery of virus has the ability to reduce or eliminate tumor burden and increase survival of the subject.

The delivery of MYXV via carrier cells represents a new potential therapeutic regimen for hematological cancers. In some embodiments, a MYXV of the disclosure is adsorbed to leukocytes (for example, leukocytes from bone marrow and/or peripheral blood), and the leukocytes are infused into a subject. Pre-loading leukocytes with MYXV ex vivo prior to leukocyte infusion into a cancer-bearing recipient can be exploited for multiple myeloma (MM) and for any other hematologic cancers disclosed herein. In some embodiments, pre-loading leukocytes with MYXV ex vivo prior to leukocyte infusion into a cancer-bearing recipient can be effective for treating any cancer amenable to the localization and infiltration of the leukocytes into distant tumor sites.

In some embodiments, the combined "leukocyte/MYXV" therapy causes increased cancer cell death in the tumor beds to enhance anti-tumor immunogenicity. For example, in some embodiments a MYXV of the disclosure (e.g., a MYXV expressing one or more immunomodulatory transgene such as BiKE, LIGHT, and/or Decorin) is delivered to cancer sites such as the bone marrow beds that harbor minimal residual disease (MRD), via migration of leukocytes pre-adsorbed or pre-infected with virus ex vivo. This systemic delivery method is sometimes called "ex vivo virotherapy", or EVV (aka EV2), because the virus is first delivered to leukocytes prior to infusion into the patient.

In some embodiments, the cell-mediated delivery of MYXV increases the level of direct killing of infected hematological cancer cells, and (while not being bound by theory) acts as an activator of the host immune system, which can lead to long term regression of cancer. This can provide a new method of treatment of hematological cancers in the bone and/or lymph nodes, which has proved to be difficult with current treatments.

Thus, in certain embodiments, methods of the disclosure comprise administering to a subject with cancer leukocytes that comprise an adsorbed MYXV of the disclosure (e.g., a MYXV that comprises one or more immunomodulatory transgenes, such as BiKE, LIGHT and/or Decorin), thereby treating and/or inhibiting the cancer in the subject.

In some embodiments, a MYXV of the disclosure is adsorbed to leukocytes (for example, leukocytes from bone marrow and/or peripheral blood), and the leukocytes are infused into a subject. The leukocytes can be from bone marrow (for example, from bone marrow aspirate or bone marrow biopsy). The leukocytes can be from blood (e.g., peripheral blood mononuclear cells). In some embodiments, the leukocytes are obtained from a subject, for example a subject that has cancer, adsorbed with MYXV, and re-infused into the subject (e.g., as an autologous cell transplant). In some embodiments, the leukocytes are obtained from one or more allogenic donors (for example, HLA-matched, HLA-mismatched, or haploidentical donors). In some embodiments, the leukocytes are obtained from an HLA-matched sibling.

The leukocytes can be sorted or purified by, for example, red blood cell lysis, density gradient centrifugation (e.g., Ficoll-Paque), leukapheresis, techniques comprising antibodies or derivatives thereof (e.g., positive or negative selection via fluorescent activated cell sorting or magnetic activated cell sorting), or any combination thereof, before or after a MYXV of the disclosure is adsorbed. In some embodiments, the leukocytes are sorted or purified to enrich for cancer cells before or after a MYXV of the disclosure is adsorbed (e.g., cells expressing a marker associated with a cancer, e.g., CD138 for multiple myeloma cells). In some embodiments, the leukocytes are sorted or purified to enrich for non-cancer cells before or after a MYXV of the disclosure is adsorbed. In some embodiments, the cells are sorted or purified to enrich for one or more a cell subsets cells before or after a MYXV of the disclosure is adsorbed (e.g., monocytes, lymphocytes, B cells, plasma cells, T cells, neutrophils, basophils, eosinophils, megakaryocytes, NK cells, NKT cells, mast cells, innate lymphoid cells, common myeloid precursors, common lymphoid precursors, myeloblasts, monoblasts, promonocytes, lymphoblasts, prolymphocytes, hemocytoblasts, megakaryoblasts, promegakaryocytes, stem cells, pro B cells, pre B cells, precursors thereof, or any combination thereof). In some embodiments, a MYXV of the disclosure is adsorbed to the leukocytes, and the leukocytes are enriched for cells comprising the MYXV (e.g., with MYXV bound and/or internalized).

The leukocytes can be stored (for example, cryopreserved) prior to or after adsorbing an MYXV of the disclosure. In some embodiments, the leukocytes can be cryopreserved, and later thawed prior to infusion into a subject.

In some embodiments, the method comprises adsorbing a MYXV of the disclosure onto the surface of leukocytes (e.g., peripheral blood mononuclear cells, bone marrow cells, or a purified/enriched subset thereof). In some embodiments, adsorbing the myxoma virus onto the surface of the leukocytes comprises exposing the leukocytes to the MYXV under conditions that permit binding of the MYXV to the surface of the mononuclear peripheral blood cells and/or bone marrow cells. In some embodiments, the method includes infecting the leukocytes with a MYXV of the disclosure. In some embodiments, infecting the leukocytes with a MYXV of the disclosure comprises exposing the leukocytes to the MYXV under conditions that permit internalization of the MYXV into the leukocytes. Exposing leukocytes to MYXV can comprise any suitable reagents or conditions (e.g., sterile cell culture media, media supplements, and appropriate incubation conditions to allow adsorption and/or infection of the leukocytes, and maintain viability of the leukocytes).

The MYXV and leukocytes can be exposed to each other at any ratio that permits the virus to adsorb to the leukocytes. In some embodiments, adsorbing the myxoma virus onto the surface of the leukocytes comprises exposing the leukocytes to the MYXV at a multiplicity of infection (MOI) of about 0.000001, 0.00001, 0.0001, 0.0001, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 600, 700, 800, 900, 1000, 2000, 3000, 4000, 5000, 6000, 7000, 8000, 9000, $1\times10^4$, $1\times10^5$, $1\times10^6$, $1\times10^9$, $1\times10^{10}$, $1\times10^{11}$, $1\times10^{12}$, $1\times10^{13}$, $1\times10^{14}$, or $1\times10^{15}$ viruses per leukocyte.

In some embodiments, adsorbing the myxoma virus onto the surface of the leukocytes comprises exposing the leukocytes to the MYXV at a multiplicity of infection (MOI) of at least 0.000001, 0.00001, 0.0001, 0.0001, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 600, 700, 800, 900, 1000, 2000, 3000, 4000, 5000, 6000, 7000, 8000, 9000, $1\times10^4$, $1\times10^5$, $1\times10^6$, $1\times10^9$, $1\times10^{10}$, $1\times10^{11}$, $1\times10^{12}$, $1\times10^{13}$, $1\times10^{14}$, or $1\times10^{15}$ viruses per leukocyte.

In some embodiments, adsorbing the myxoma virus onto the surface of the leukocytes comprises exposing the leukocytes to the MYXV at a multiplicity of infection (MOI) of at most 0.000001, 0.00001, 0.0001, 0.0001, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 600, 700, 800, 900, 1000, 2000, 3000, 4000, 5000, 6000, 7000, 8000, 9000, $1\times10^4$, $1\times10^5$, $1\times10^6$, $1\times10^9$, $1\times10^{10}$, $1\times10^{11}$, $1\times10^{12}$, $1\times10^{13}$, $1\times10^{14}$, or $1\times10^{15}$ viruses per leukocyte.

In some embodiments, adsorbing the myxoma virus onto the surface of the leukocytes comprises exposing the leukocytes to the MYXV at a multiplicity of infection (MOI) of between about, for example, 0.000001 to $1\times10^{15}$, 0.0001 to $1\times10^6$, 0.001 to $1\times10^4$, 0.001 to 1000, 0.001 to 100, 0.001 to 10, 0.001 to 1, 0.001 to 0.1, 0.001 to 0.01, 0.01 to $1\times10^4$, 0.01 to 1000, 0.01 to 100, 0.01 to 10, 0.01 to 1, 0.01 to 0.1, 0.1 to $1\times10^4$, 0.1 to 1000, 0.1 to 100, 0.1 to 10, 0.1 to 1, 1 to $1\times10^4$, 1 to 1000, 1 to 100, or 1 to 10 viruses per leukocyte.

In some embodiments, adsorbing the myxoma virus onto the surface of the leukocytes comprises exposing the leukocytes to the MYXV at a multiplicity of infection (MOI) of between about 0.1 to 10. In some embodiments, adsorbing the myxoma virus onto the surface of the leukocytes comprises exposing the leukocytes to the MYXV at a multiplicity of infection (MOI) of between about 0.01 to 100. In some embodiments, adsorbing the myxoma virus onto the surface of the leukocytes comprises exposing the leukocytes to the MYXV at a multiplicity of infection (MOI) of between about 0.001 to 1000.

In some embodiments, the leukocytes are contacted or adsorbed with a MYXV of the disclosure for a period of about 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 2.5 hours, 3 hours, 3.5 hours, 4 hours, 4.5 hours, 5 hours, 5.5 hours, 6 hours, 7 hours, 8 hours, 9 hours, 10 hours, 11 hours, 12 hours, 13 hours, 14 hours, 15 hours, 16 hours, 18 hours, 20 hours, 22 hours, or 24 hours.

In some embodiments, the leukocytes are contacted or adsorbed with a MYXV of the disclosure for a period of at least 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 2.5 hours, 3 hours, 3.5 hours, 4 hours, 4.5 hours, 5 hours, 5.5 hours, 6 hours, 7 hours, 8 hours, 9 hours, 10 hours, 11 hours, 12 hours, 13 hours, 14 hours, 15 hours, 16 hours, 18 hours, 20 hours, 22 hours, 24 hours, or more.

In some embodiments, the leukocytes are contacted or adsorbed with a MYXV of the disclosure for a period of at most 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 2.5 hours, 3 hours, 3.5 hours, 4 hours, 4.5 hours, 5 hours, 5.5 hours, 6 hours, 7 hours, 8 hours, 9 hours, 10 hours, 11 hours, 12 hours, 13 hours, 14 hours, 15 hours, 16 hours, 18 hours, 20 hours, 22 hours, 24 hours, or less.

In some embodiments, the BM or PBMC cells are contacted or adsorbed with MYXV constructs ex vivo for about one hour.

Additional Ex Vivo Methods

As disclosed herein, MYXV is capable of selectively infecting cells that have a deficient innate anti-viral response, and can be used as an indicator of such a deficiency in cells. Thus, cells removed from a subject may be assayed for deficiency in an innate anti-viral response using the methods of the present disclosure. Such determination may indicate, when combined with other indicators, that the subject may be suffering from a particular disease state, for example, cancer. The cells may be removed from a subject, including a human subject, using known biopsy methods. The biopsy method will depend on the location and type of cell that is to be tested. Cells can be cultured and exposed to MYXV, for example by adding live MYXV to the culture medium. The multiplicity of infection (MOI), may be varied to determine an optimum MOI for a given cell type, density and culture technique, using a positive control cell culture that is known to be infected upon exposure to MYXV.

The amount of MYXV added to the cultured cells may be varied depending on cell type, method of culturing and strain of virus.

Infectivity of the cultured cells by MYXV may be determined by various methods known to a skilled person, including the ability of the MYXV to cause cell death. It may also involve the addition of reagents to the cell culture to complete an enzymatic or chemical reaction with a viral expression product. The viral expression product may be expressed from a reporter gene that has been inserted into the MYXV genome.

In one embodiment, the MYXV may be modified to enhance the ease of detection of infection state. For example, the MYXV may be genetically modified to express a marker that can be readily detected by phase contrast microscopy, fluorescence microscopy, or by radioimaging. The marker may be an expressed fluorescent protein or an expressed enzyme that may be involved in a colorimetric or radiolabeling reaction. In some embodiments, the marker may be a gene product that interrupts or inhibits a particular function of the cells being tested.

Pharmaceutical Compositions

An MYXV of the disclosure or a cell comprising an MYXV of the disclosure can be formulated as an ingredient in a pharmaceutical composition. Therefore, in some embodiments, the disclosure provides a pharmaceutical composition comprising a Myxoma virus expressing one or more immunomodulatory transgenes, (such as BiKE, LIGHT, and/or Decorin), and a pharmaceutically acceptable diluent or excipient. The compositions may contain pharmaceutically acceptable concentrations of salt, buffering agents, preservatives and various compatible carriers.

The pharmaceutical compositions may contain additional therapeutic agents, such as additional anti-cancer agents. In one embodiment, the compositions include a chemotherapeutic agent. The chemotherapeutic agent, for example, may be substantially any agent, which exhibits an effect against cancer cells or neoplastic cells of the subject and that does not inhibit or diminish the tumor killing effect of the MYXV expressing one or more immunomodulatory transgenes. For example, the chemotherapeutic agent may be, without limitation, an anthracycline, an alkylating agent, an alkyl sulfonate, an aziridine, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. The chemotherapeutic agent can be one that is known to be effective against the particular cell type that is cancerous or neoplastic.

The proportion and identity of the pharmaceutically acceptable diluent can be determined, for example, by chosen route of administration, compatibility with a live virus, and standard pharmaceutical practice. In some embodiments, the pharmaceutical composition will be formulated with components that will not significantly impair the biological properties of the MYXV expressing one or more immunomodulatory transgenes, such as BiKE, LIGHT and/or Decorin. The pharmaceutical composition can be prepared by known methods for the preparation of pharmaceutically acceptable compositions suitable for administration to subjects, such that an effective quantity of the active substance or substances is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1995). On this basis, the compositions can comprise solutions of the MYXV or cells comprising the MYXV in association with one or more pharmaceutically acceptable vehicles or diluents, and contained in buffer solutions with a suitable pH and iso-osmotic with physiological fluids.

The pharmaceutical composition may be administered to a subject in a variety of forms depending on the selected route of administration. The composition of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time (e.g., intravenous infusion).

The pharmaceutical composition may be administered orally, for example, with an inert diluent or with a carrier, or it may be enclosed in hard or soft shell gelatin capsules, or it may be compressed into tablets. For oral therapeutic administration, the MYXV expressing one or more immunomodulatory transgenes (such as BiKE, LIGHT and/or Decorin) may be incorporated with an excipient and be used in the form of ingestible tablets, buccal tablets, troches, capsules, elixirs, suspensions, syrups, wafers and the like.

Solutions of an MYXV of the disclosure or cells comprising an MYXV of the disclosure can be prepared in a physiologically suitable buffer. Under ordinary conditions of storage and use, these preparations can contain a preservative to prevent the growth of microorganisms, but that will not inactivate the live virus. Conventional procedures and ingredients for the selection and preparation of suitable formulations are described, for example, in Remington's Pharmaceutical Sciences and in The United States Pharmacopeia: The National Formulary (USP 24 NF19) published in 1999. The dose of the pharmaceutical composition that is to be used depends on the particular condition being treated, the severity of the condition, the individual subject parameters including age, physical condition, size and weight, the duration of the treatment, the nature of concurrent therapy (if any), the specific route of administration and other similar factors that are within the knowledge and expertise of the health practitioner. In certain embodiments, the therapeutic virus may be freeze dried for storage at room temperature.

Kits

Aspects of the present disclosure concern a MYXV that expresses one or more immunomodulatory transgenes, such as BiKE, LIGHT and Decorin, and kits including the same. The MYXV expressing one or more immunomodulatory transgenes, such as BiKE, LIGHT and/or Decorin, or pharmaceutical compositions comprising the MYXV, can be packaged as a kit, for example, containing instructions for use of the MYXV. A kit can comprise any MYXV disclosed herein, for example, a MYXV comprising one or more immunomodulatory transgenes, one or more reporter transgenes, one or more non-immunomodulatory transgenes, or a combination thereof. In some embodiments, a kit comprises a MYXV-LIGHT, a MYXV-BiKE, a MYXV-Decorin, or a combination thereof. In some embodiments, a kit comprises MYXV-FLuc-huLIGHT-TdTomato, MYXV-huBiKE-GFP, and/or MYXV-mDecorin-GFP.

EXAMPLES

Example 1: Design of Recombinant MYXV Constructs Expressing Decorin, LIGHT or BiKE Construction of MYXV-mDecorin-GFP MYXV virus expressing mouse Decorin: Decorin is a member of the extracellular matrix proteoglycans family that exists and functions in stromal and epithelial cells (Nemani N, Santo L, Eda H, Cirstea D, Mishima Y, Patel C, et al. Role of decorin in multiple myeloma (MM) bone marrow microenvironment. *J Bone Miner Res.* 2015; 30(3): 465-70). Accumulating evidence indicates that decorin affects the biology of different types of cancers by directly or indirectly targeting signaling molecules involved in cell growth, survival, metastasis, and angiogenesis, for example, targeting for sequestration. Decorin can bind and block the activity of TGF-β, which can be one of the main inhibitory cytokines responsible of immune suppression in the tumor microenvironment. Therefore, a MYXV oncolytic vector expressing Decorin will block TGF-β in the tumor microenvironment and potentially promote a stronger anti-tumor immune response in a wide variety of solid and hematologic cancers. In addition to this, decorin could directly inhibit tumor cell growth and proliferation. For example, adenoviral delivery of decorin into various hematological cancers can counteract tumorigenesis (Jiang G, Sun C, Li R H, Wei Z P, Zheng J N, and Liu Y Q. Enhanced antitumor efficacy of a novel oncolytic adenovirus combined with temozolomide in the treatment of melanoma in vivo. *J Cancer Res Clin Oncol.* 2015; 141(1):75-85; Kaliberova L N, Krendelchtchikova V, Harmon D K, Stockard C R, Petersen A S, Markert J M, et al. CRAdRGDflt-IL24 virotherapy in combination with chemotherapy of experimental glioma. *Cancer Gene Ther.* 2009; 16(10):794-805; and Xu W, Neill T, Yang Y, Zebin Hu, Cleveland E, Wu Y, et al. The systemic delivery of an oncolytic adenovirus expressing decorin inhibits bone metastasis in a mouse model of human prostate cancer. *Gene Ther.* 2015; 22(3):247-56). These preclinical discoveries highlight decorin as a potential anti-cancer target for many types of cancer.

Figure 1A:
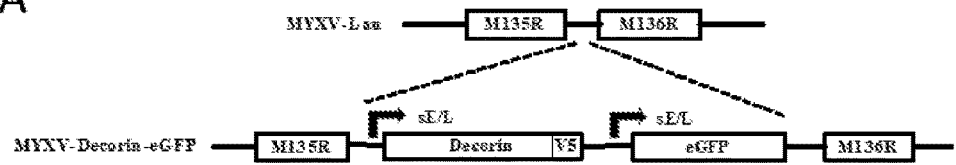
FIGS. 1A-1G show the construction of MYXV-mDecorin-GFP.

MYXV-mDecorin-GFP was constructed by inserting a Decorin-expressing cassette containing the murine decorin coding sequence (NM_001190451.2; GenScript) with a C-terminal V5-tag and under the control of the poxvirus synthetic early/late promoter (sE/L) at an intergenic location between the M135 and M136 genes in the wild-type (wt) MYXV strain Lausanne (MYXV-Lau) genome (FIG. 1A). An expression cassette for an enhanced green fluorescent protein (eGFP) was inserted immediately downstream of the decorin expression cassette, and its expression was also driven by a poxvirus synthetic early/late promoter. The eGFP serves as a fluorescent marker for MYXV replication in vitro and in vivo, as MYXV infection can be monitored by live imaging of eGFP expression.

To create the MYXV-mDecorin-GFP construct, a recombinant plasmid was first constructed using the Gateway System (ThermoFisher Scientific). Upstream and downstream hybridizing sequences were amplified by PCR to generate entry clones by Gateway BP recombination with appropriate pDONR vectors. The final recombinant plasmid was constructed by recombining three entry clones with a destination vector in a sequential manner. The Decorin and eGFP expression cassettes were inserted into the MYXV genome by infecting the rabbit kidney13 (RK13) cell line with MYXV-Lau and then transfecting the appropriate recombination plasmid. Multiple rounds of foci purification were conducted to obtain pure stocks of the recombinant viruses. The presence of the transgene was confirmed using the specific primers for Decorin:

AttB4r_mDCN F:

(SEQ ID NO: 1)
GGGGACAACTTTTCTATACAAAGTTGCCAAAATTGAAATTTTATTTTTTT

TTTTTGGAATATAAATAATGAAGGCAACTCTCATCTT.

Figure 1B:
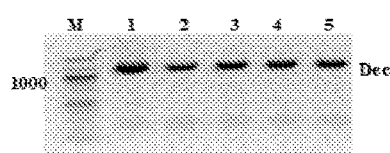
Figure 1C:
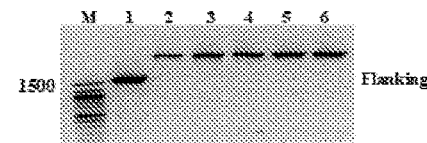

AttB3r_mDCN_R: GGGGACAACTTTATTATA-CAAAGTTGTTTAAGAATCGAGACCGAG-GAGAGGGTTAGGGATAGG CTTACC CTTGTAGTTTCCAAGTTGAA (SEQ ID NO: 2). The purity was confirmed by PCR using the appropriate primers set (FIGS. 1B-C).

Figure 1D:
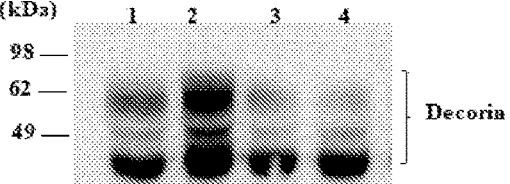
Figure 1E:
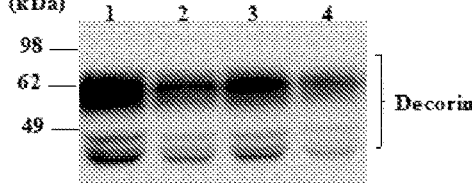

Several Decorin protein species (40-60 kDa) were detected by Western Blot in lysates from MYXV-Decorin-infected RK13 cells by using a mouse monoclonal antibody specific to the V5 tag (Invitrogen) (FIGS. 1D-E).

Figure 1F:
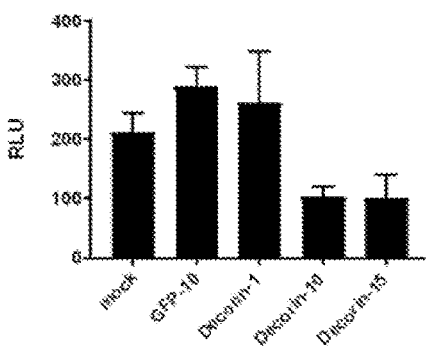
Figure 1G:
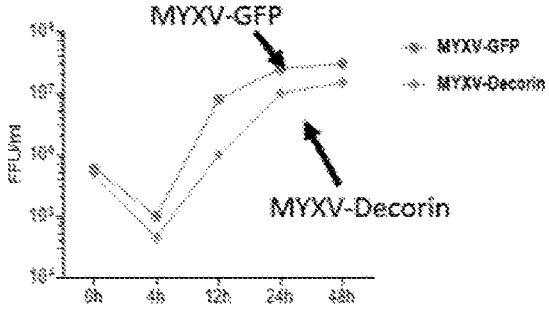

The ability of MYXV-Decorin infected RK13 cells to express biologically active protein and to suppress TGF-β bioactivity was evaluated using a mink lung epithelial cell line that is stably transfected with a plasminogen activator inhibitor-1 promoter-Luciferase construct (MLE/PAI/L cells). Exposure of MLE/PAI/L cells to TGF-β induces a dose-dependent increase in Luciferase activity. MLE/PAI/L cells were incubated with conditioned medium containing 0.1 ng/mL recombinant TGF-β mixed with supernatants from RK13 cells that were mock-infected or infected with MYXV strains under various conditions, and luciferase activity was measured to quantify TGF-β bioactivity. Supernatants were from RK13 cells that were: (i) mock-infected, (ii) infected with MYXV-GFP (a control lacking Decorin) at an MOI of 10, or (iii) infected with MYXV-mDecorin-GFP at an MOI of either 1, 10, or 15. Supernatants from RK13 cells infected with MYXV-mDecorin-GFP at multiplicities of infection of 10 or 15 were able to suppress the biological activity of TGF-β (FIG. 1F). The replication capacity in RK13 cells of the new construct MYXV-mDecorin-GFP was similar to the parental virus MYXV-GFP (FIG. 1G).

Construction of MYXV-BiKE-GFP

MYXV-Bi-specific Natural Killer and Neutrophil engager (BiKE) (CD138-CD16): BiKE is a molecule comprising two single chain variable fragments (scFvs) derived from antibodies, joined by a short peptide linker. One scFv arm binds CD16 on the surface of NK cells and neutrophils, while the other binds a chosen target antigen (in this case CD138, a hallmark of multiple myeloma (MM) cells). These molecules are designed to form an antigen-specific immunological synapse between NK cells or neutrophils and tumor cells in order to trigger enhanced NK/neutrophil cell-mediated killing of tumor targets. Several BiKEs have shown promising results in different murine tumor models (Davis Z B, Vallera D A, Miller J S, and Felices M. Natural killer cells unleashed: Checkpoint receptor blockade and BiKE/TriKE utilization in NK-mediated anti-tumor immunotherapy. *Semin Immunol.* 2017; 31:64-75). Expressing a secreted BiKE construct from MYXV could potentiate the capacity of NK and neutrophils to kill MM cells in the TME, and the virus-expressed BiKE technology could also be applied to any other cancers for which a cancer-specific cell surface marker exists.

The anti-CD16 scFv (heavy and light chain variable domains) human Ab sequences were obtained from publicly available sources (AY345160.1 and AY345161.2; Genbank). The anti-CD138 scFv sequence was obtained from publicly available sources (Genbank). To form scFvs, the anti-CD16 variable regions were connected by a (G4S1)3 linker, and the anti-CD138 variable regions were connected by a (G4S1)3 linker. The anti-CD16 and anti-CD138 scFvs were connected to each other by a (G4S1)2 flexible linker. The BiKE was arranged VL(CD138)-VH(CD138)-VH(CD16)-VL(CD16), and included the signal peptide from the mouse Ig heavy chain at the N-terminus, and a V5 tag at the C-terminus (FIG. 2A and SEQ ID NO: 6). The BiKE construct was optimized for human codon usage and synthesized by Genscript.

MYXV-BiKE-GFP was constructed by inserting a BiKE-expressing cassette containing the BiKE coding sequence (GenScript) with a C-terminal V5-tag and under the control of the poxvirus synthetic early/late promoter (sE/L) at an intergenic location between the M135 and M136 genes in the wild-type (wt) MYXV strain Laussane (MYXV-Lau) genome. An expression cassette for an enhanced green fluorescent protein (eGFP) was inserted immediately downstream of the BiKE expression cassette, and its expression was also driven by a poxvirus synthetic early/late promoter (FIG. 2B). The eGFP can serve as a fluorescent marker for MYXV replication in vitro and in vivo, as MYXV infection can be monitored by live imaging of GFP expression. To create the MYXV-BiKE construct, a recombinant plasmid was first constructed using Gateway System (ThermoFisher Scientific). Upstream and downstream hybridizing sequences were amplified by PCR to generate entry clones by Gateway BP recombination with appropriate pDONR vectors. The final recombinant plasmid was constructed by recombining three entry clones with a destination vector in a sequential manner. The BiKE and eGFP expression cassettes were inserted into the MYXV genome by infecting RK13 cells with MYXV-Lau and then transfecting the appropriate recombination plasmid. Multiple rounds of foci purification were conducted to obtain pure stocks of the recombinant viruses, the specificity confirmed by PCR using the appropriate primers set:

BiKE_CD16_F TCAGCAAGGACACATCCTCTAA (SEQ ID NO: 3)

BiKE_CD16_R TAAGGATCCTCATTGGACTGC (SEQ ID NO: 4)

The purity was also confirmed by PCR using the appropriate primers set (FIGS. 2C-D).

BiKE expression was confirmed by Western Blot, by detecting the presence of a band of 56 kDa in lysates from MYXV-BiKE infected RK13 cells by using a mouse monoclonal Ab specific to the V5 tag (Invitrogen), both in cell lysates and supernatants (FIG. 2E). The replication capacity of the new construct MYXV-BiKE in RK13 cells was similar to the parental virus MYXV-GFP (FIG. 2F).

SEQ ID NO: 5 provides the nucleotide sequence of a transgene encoding the BiKE. SEQ ID NO: 6 provides the amino acid sequence of a transgene encoding the BiKE. In SEQ ID NO: 6, the N-terminal signal sequence is underlined, linkers are in bold, and the C-terminal V5 tag is in italics.

DNA Bike Sequence:

```
                                      (SEQ ID NO: 5)
ATGAAGAGCCAGACCCAGGTGTTCATCTTCCTGCTGCTGTGCGTGAGCGG

CGCCCACGGCGACATCCAGATGACCCAGAGCACCAGCAGCCTGAGCGCCA

GCCTGGGCGACAGGGTGACCATCAGCTGCAGCGCCAGCCAGGGCATCAAC

AACTACCTGAACTGGTACCAGCAGAAGCCCGACGGCACCGTGGAGCTGCT

GATCTACTACACCAGCACCCTGCAGAGCGGCGTGCCCAGCAGGTTCAGCG

GCAGCGGCAGCGGCACCGACTACAGCCTGACCATCAGCAACCTGGAGCCC

GAGGACATCGGCACCTACTACTGCCAGCAGTACAGCAAGCTGCCCCAGGAC

CTTCGGCGGCGGCACCAAGCTGGAGATCAAGGGTGGCGGTGGCTCCGGCG

GTGGTGGGTCGGGTGGCGGCGGATCTAGCCAGGTGCAGCTGCAGCAGAGC

GGCAGCGAGCTGATGATGCCCGGCGCCAGCGTGAAGATCAGCTGCAAGGC

CACCGGCTACACCTTCAGCAACTACTGGATCGAGTGGGTGAAGCAGAGGC

CCGGCCACGGCCTGGAGTGGATCGGCGAGATCCTGCCCGGCACCGGCAGG

ACCATCTACAACGAGAAGTTCAAGGGCAAGGCCACCTTCACCGCCGACAT

CAGCAGCAACACCGTGCAGATGCAGCTGAGCAGCCTGACCAGCGAGGACA

GCGCCGTGTACTACTGCGCCAGGAGGGACTACTACGGCAACTTCTACTAC

GCCATGGACTACTGGGGCCAGGGCACCAGCGTGACCGTGAGCAGCGGTGG

CGGTGGCTCCGGCGGTGGTGGGTCGCAGGTTACTCTGAAAGAGTCTGGCC

CTGGGATATTGCAGCCCTCCCAGACCCTCAGTCTGACTTGTTCTTTCTCT

GGGTTTTCACTGAGGACTTCTGGTATGGGTGTAGGCTGGATTCGTCAGCC

TTCAGGGAAGGGTCTAGAGTGGCTGGCACACATTTGGTGGGATGATGACA

AGCGCTATAATCCAGCCCTGAAGAGCCGACTGACAATCTCCAAGGATACC
```

-continued

```
TCCAGCAACCAGGTATTCCTCAAAATCGCCAGTGTGGACACTGCAGATAC

TGCCACATACTACTGTGCTCAAATAAACCCCGCCTGGTTTGCTTACTGGG

GCCAAGGGACTCTGGTCACTGTCTCTGCCGGTGGCGGTGGCTCCGGCGGT

GGTGGGTCGGGTGGCGGCGGATCTGACACTGTGCTGACCCAATCTCCAGC

TTCTTTGGCTGTGTCTCTAGGGCAGAGGGCCACCATCTCCTGCAAGGCCA

GCCAAAGTGTTGATTTTGATGGTGATAGTTTTATGAACTGGTACCAACAG

AAACCAGGACAGCCACCCAAACTCCTCATCTATACTACATCCAATCTAGA

ATCTGGGATCCCAGCCAGGTTTAGTGCCAGTGGGTCTGGGACAGACTTCA

CCCTCAACATCCATCCTGTGGAGGAGGAGGATACTGCAACCTATTACTGT

CAGCAAAGTAATGAGGATCCGTACACGTTCGGAGGGGGGACCAAGCTGGA

AATAAAAGGTAAGCCTATCCCTAACCCTCTCCTCGGTCTCGATTCTACGT

AA.
```

Protein BiKE Sequence:

```
                                        (SEQ ID NO: 6)
MKSQTQVFIFLLLCVSGAHGDIQMTQSTSSLSASLGDRVTISCSASQGIN

NYLNWYQQKPDGTVELLIYYTSTLQSGVPSRFSGSGSGTDYSLTISNLEP

EDIGTYYCQQYSKLPRTFGGGTKLEIKGGGGSGGGGSGGGGSSQVQLQQS

GSELMMPGASVKISCKATGYTFSNYWIEWVKQRPGHGLEWIGEILPGTGR

TIYNEKFKGKATFTADISSNTVQMQLSSLTSEDSAVYYCARRDYYGNFYY

AMDYWGQGTSVTVSSGGGGSGGGGSQVTLKESGPGILQPSQTLSLTCSFS

GFSLRTSGMGVGWIRQPSGKGLEWLAHIWWDDDKRYNPALKSRLTISKDT

SSNQVFLKIASVDTADTATYYCAQINPAWFAYWGQGTLVTVSAGGGGGG

GSGGGGSDTVLTQSPASLAVSLGQRATISCKASQSVDFDGDSFMNWYQQK

PGQPPKLLIYTTSNLESGIPARFSASGSGTDFTLNIHPVEEEDTATYYCQ

QSNEDPYTFGGGTKLEIKGKPIPNPLLGLDST.
```

Construction of MYXV-FLuc-LIGHT-TdTomato Viruses

LIGHT (corresponding to Lymphotoxins, exhibits Inducible expression, and competes with HSV Glycoprotein D for Herpesvirus entry mediator (HVEM), a receptor expressed by T lymphocytes) is a member of the TNF superfamily (gene: TNFSF14). LIGHT is a type II transmembrane protein that assembles into a homotrimeric form that binds to three known receptors, the herpes simplex virus cell receptor HveA (formerly HVEM), lymphotoxin-β receptor (LT-DR), and decoy receptor 3 (DcR3/TR6). LIGHT is expressed on activated T cells (CD4$^+$ and CD8$^+$ types) and immature dendritic cells (DCs). Previous studies identified LIGHT as an immune-stimulatory cytokine for its ability to trigger T-cell proliferation and secretion of T helper cell 1 (Th1) cytokines. Due to its potent immune stimulatory activity in T cells and DCs and widespread expression of its cognate receptor, HveA, LIGHT is a promising candidate molecule to stimulate anti-tumor immune responses (Yu P, and Fu Y X. Targeting tumors with LIGHT to generate metastasis-clearing immunity. *Cytokine Growth Factor Rev.* 2008;19 (3-4):285-94).

Expression of LIGHT within the tumor microenvironment has been shown to create a massive infiltration of naïve T cells, which upregulate both chemokine production and expression of adhesion molecules. Activation of the infiltrating T cells can be critical for positive cancer-regression responses to immune checkpoint inhibitor (ICI)-resistant cancers, and for clearance of metastatic cancer sites (Yu P, Lee Y, Liu W, Chin R K, Wang J, Wang Y, et al. Priming of naive T cells inside tumors leads to eradication of established tumors. *Nat Immunol.* 2004; 5(2):141-9; Tang H, Wang Y, Chlewicki L K, Zhang Y, Guo J, Liang W, et al. Facilitating T Cell Infiltration in Tumor Microenvironment Overcomes Resistance to PD-L1 Blockade. *Cancer Cell.* 2016; 29(3):285-96). The LIGHT-mediated activation of LTOR signaling in tumor tissues results in the induction of multiple chemokines and adhesion molecules, promoting effective T cell recruitment to the tumor tissue, and T cell activation. For example, adenovirus vectors constructed to deliver LIGHT into the tumor tissue promote reduction of tumor growth and metastases and robust immune responses in mouse tumor models (Yu P, and Fu Y X. Targeting tumors with LIGHT to generate metastasis-clearing immunity. *Cytokine Growth Factor Rev.* 2008;19(3-4):285-94).

Based on these immune-stimulatory properties, LIGHT is considered a promising candidate for cancer immunotherapy. Therefore, a LIGHT-expressing oncolytic MYXV platform could enhance anti-cancer immune responses, and could, for example, enhance the efficacy of Immune Checkpoint Inhibitors (ICIs) in addition to virotherapy.

The construction of recombinant MYXVs that expresses human or mouse LIGHT/TNFSF14 started with collecting the cDNA of the respective genes. Human and mouse LIGHT/TNFSF14 cDNAs were purchased from GenScript. The transgenes can be expressed under a poxvirus synthetic early/late promoter (sE/L), that allow expression only in virus-infected cells. In addition to transgene, a reporter gene, for example green fluorescent protein (GFP) or TdTomato, can also be expressed under a poxvirus promoter for quick selection and purification of transgene-expressing recombinant virus. Additional reporter genes, for example Firefly luciferase (F-Luc) can allow real time monitoring of viral replication in live animals. The transgene and reporter genes can be inserted between the ORFs M135 and M136 to maintain a parental wild type MYXV backbone. Transgenes can also be inserted in a gene knockout virus background. In this case, the M135 gene locus was selected for the construction of transgene expressing cassette. MYXV The final recombination plasmid cassette contains: transgene, reporter gene(s) and gene sequences from MYXV where the recombination will take place.

Figure 3:
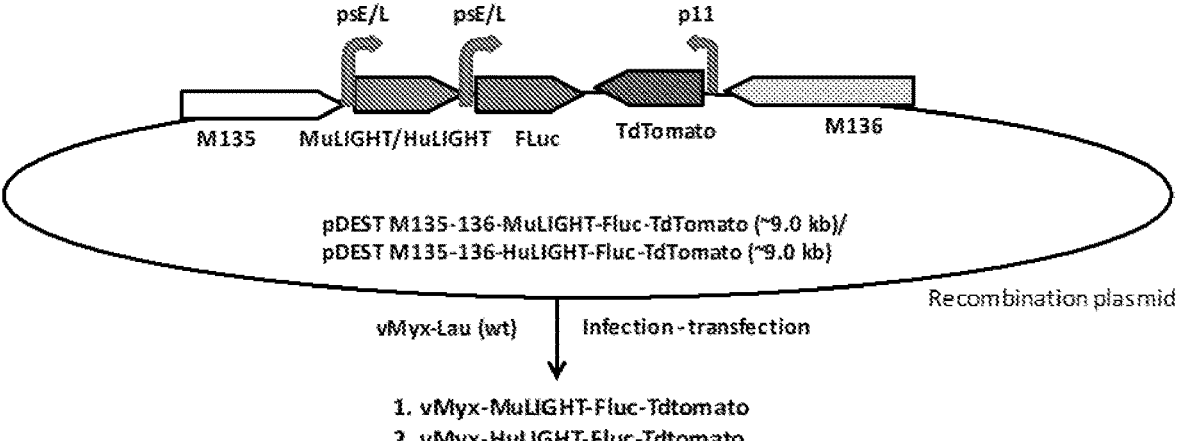
FIG. 3 is a plasmid map showing the generation of Human and Murine LIGHT expressing wild-type (wt) myxoma viruses. Note that this virus has a wild-type MYXV backbone, because the LIGHT transgene is inserted at an intergenic locus between the viral M135R and M136R genes, and thus there is no gene knockout or disruption of M135R or M136R.
Figure 4:
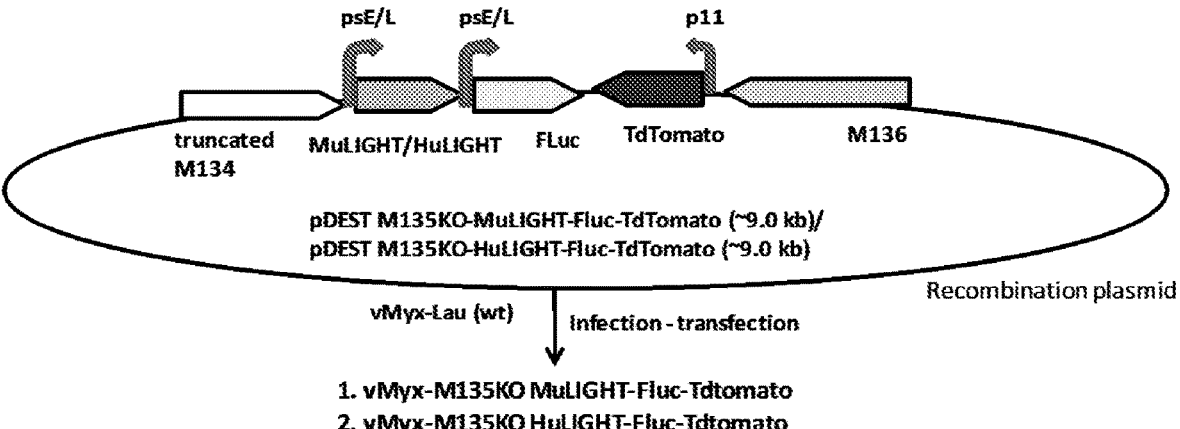
FIG. 4 is a plasmid map showing the generation of Human and Murine LIGHT expressing M135KO myxoma viruses. Note this virus has a knockout of the viral M135R gene.
Figure 5A:
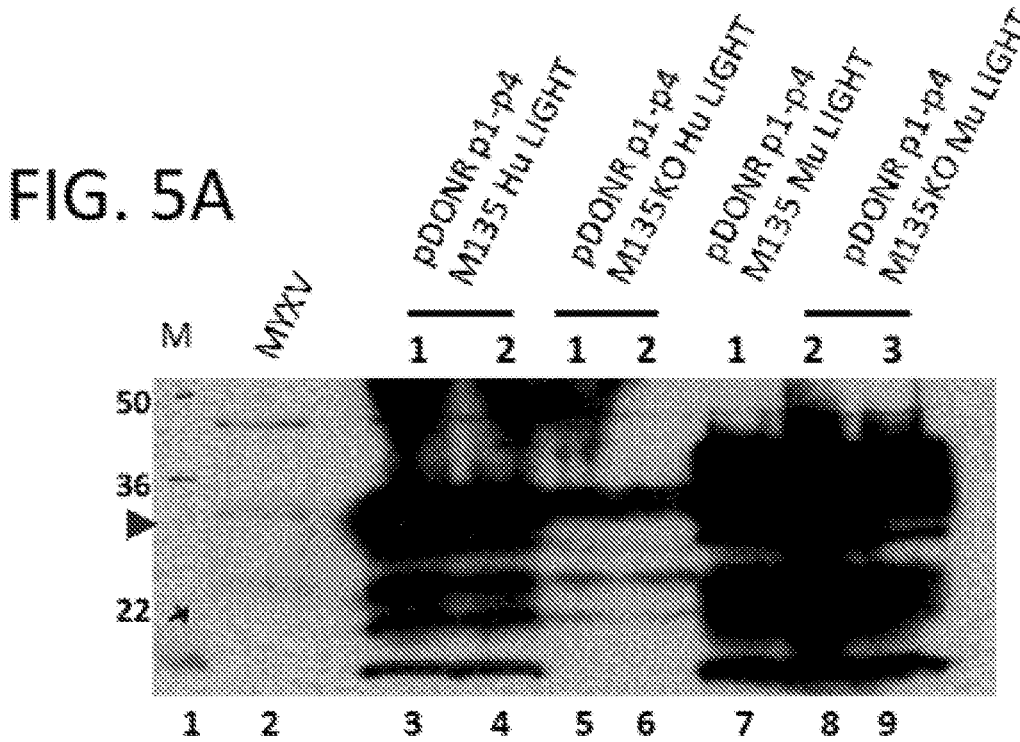
FIG. 5A shows a Western blot analysis of the expression of human and murine LIGHTs under poxvirus sE/L promoter from recombinant plasmids.
Figure 5B:
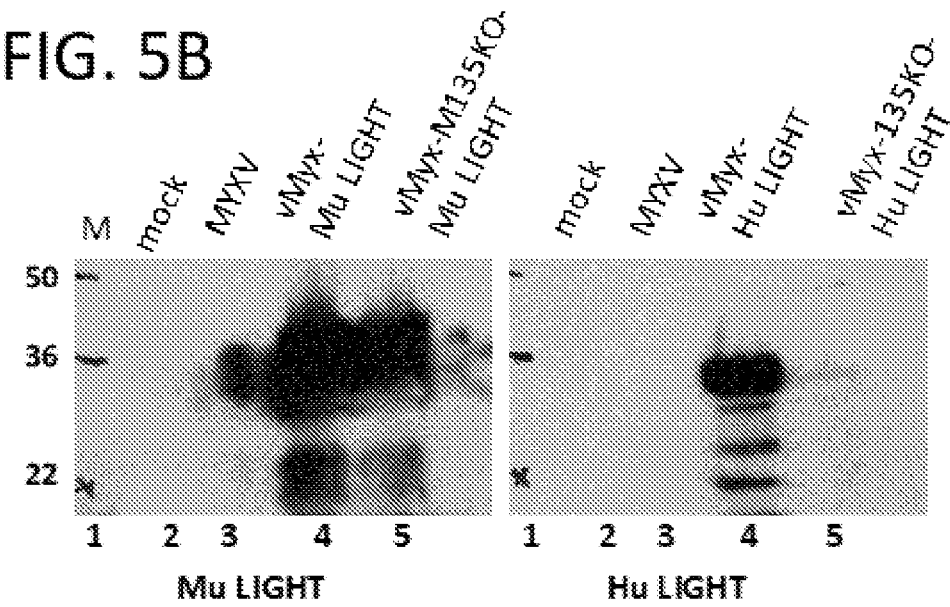
FIG. 5B shows a Western blot analysis of the expression of human and murine LIGHTs from the recombinant MYXVs.
Figure 6A:
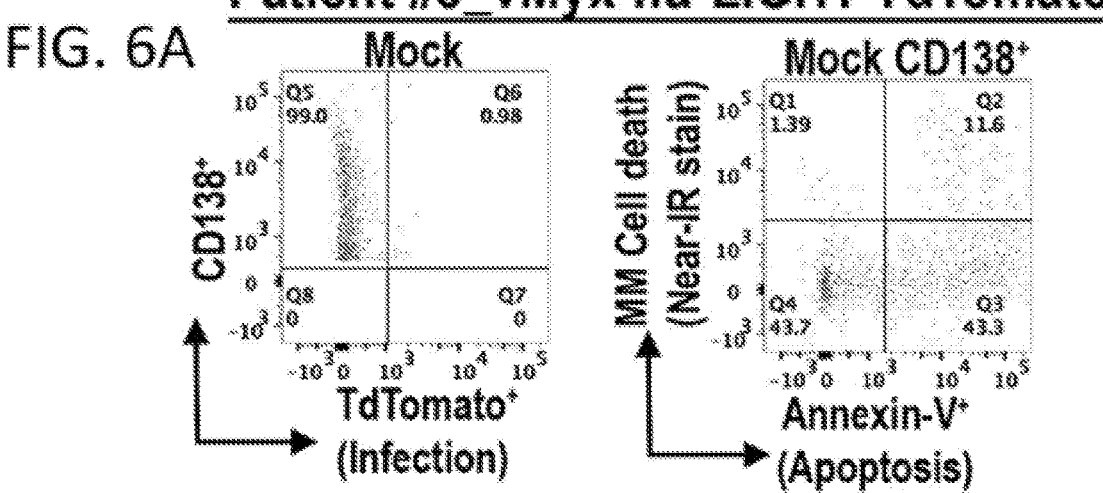
FIGS. 6A-6C show MYXV-FLuc-huLIGHT-TdTomato productively infects and induces direct multiple myeloma (MM) cell killing in a primary human sample from patient #3 contaminated with MM.
Figure 6B:
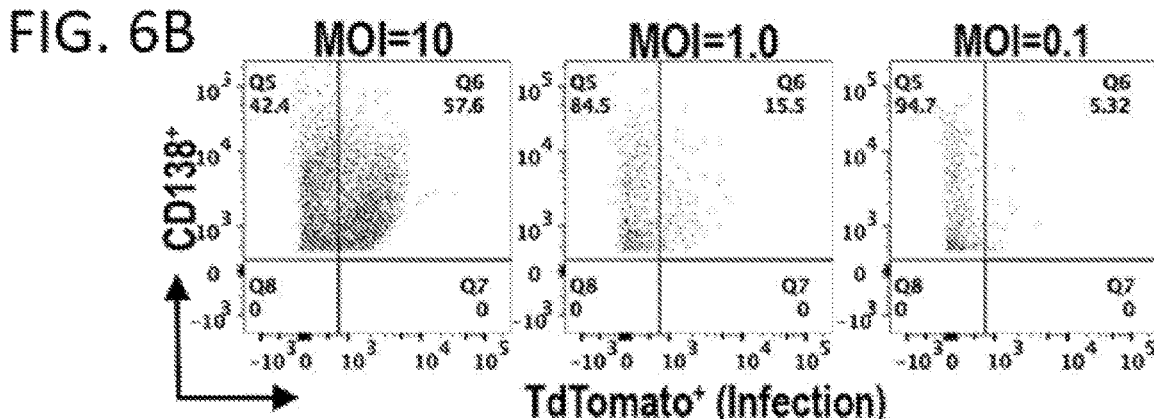
Figure 6C:
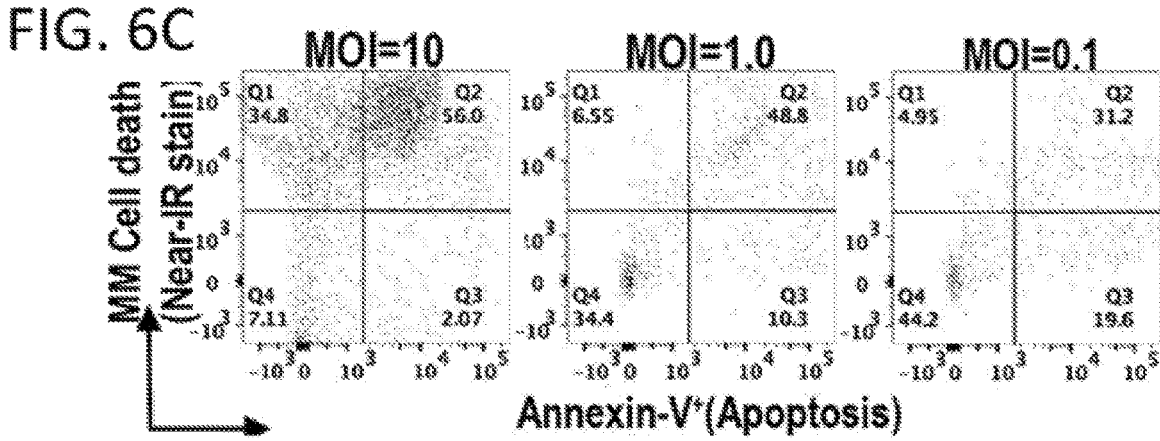
Figure 7A:
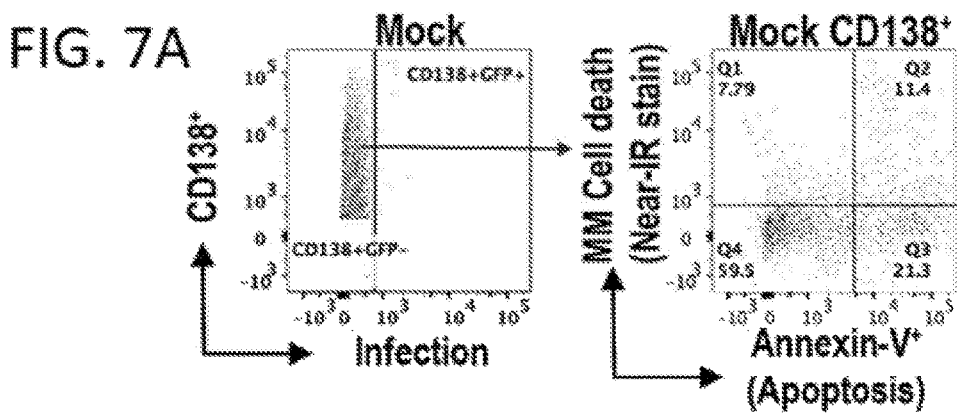
FIGS. 7A and 7B show killing of uninfected MM cells (i.e. TdTomato−) from primary human sample from patient #3 contaminated with multiple myeloma (MM) cells that was exposed to MYXV-FLuc-huLIGHT-TdTomato.
Figure 7B:
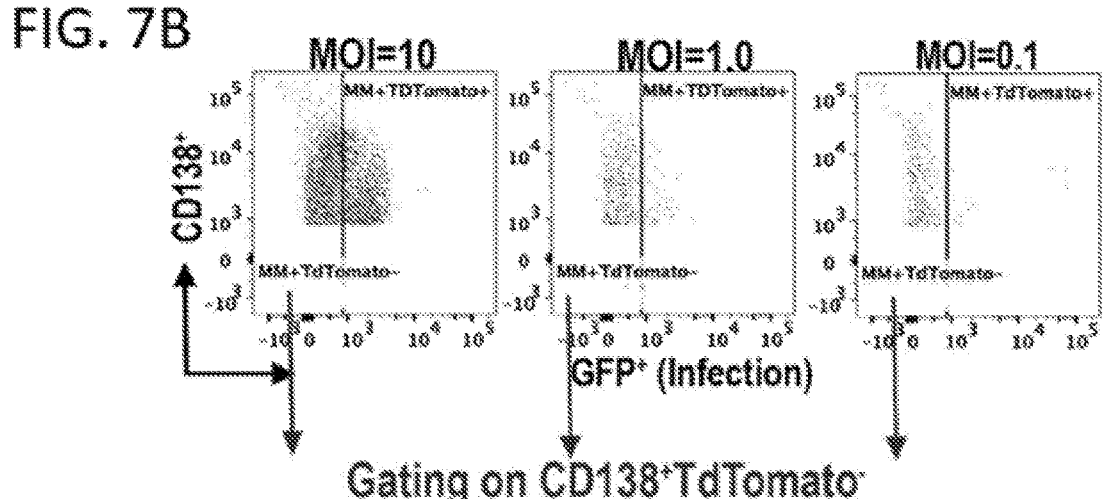
Figure 7B:
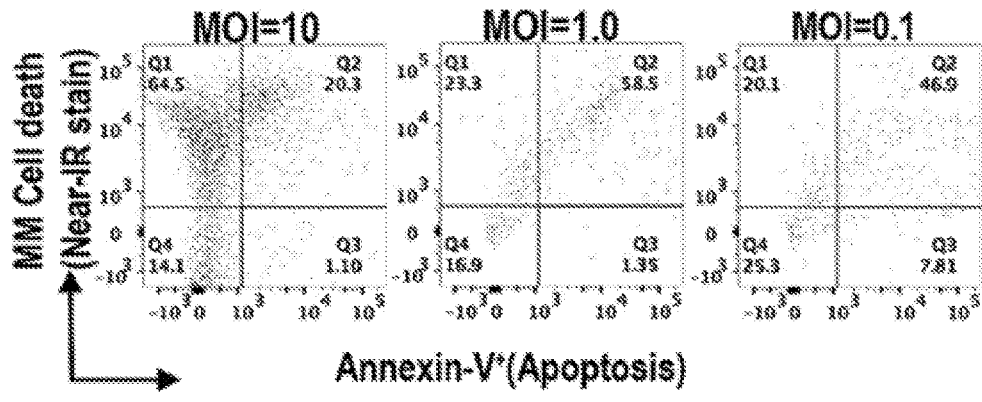
Figure 8A:
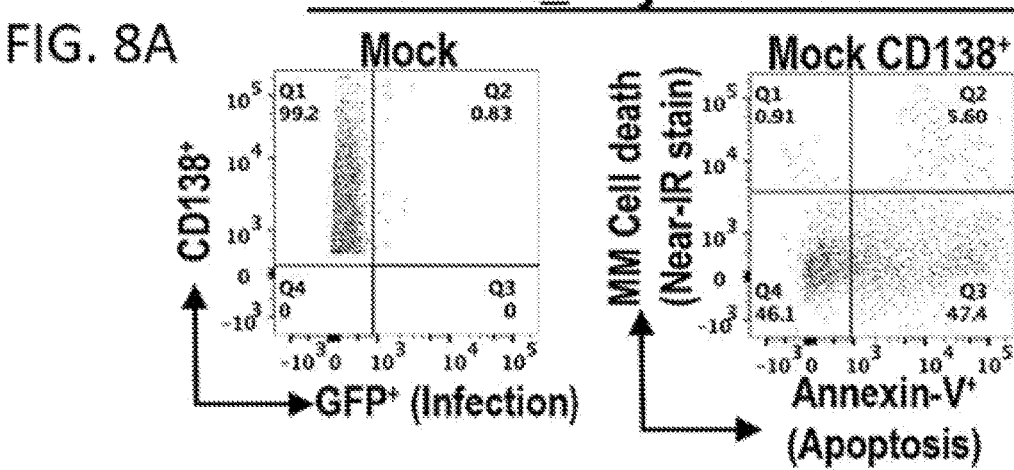
FIGS. 8A-8C show MYXV-huBiKE-GFP productively infects and induces killing of a primary human sample from patient #3 contaminated with multiple myeloma (MM) cells.
Figure 8B:
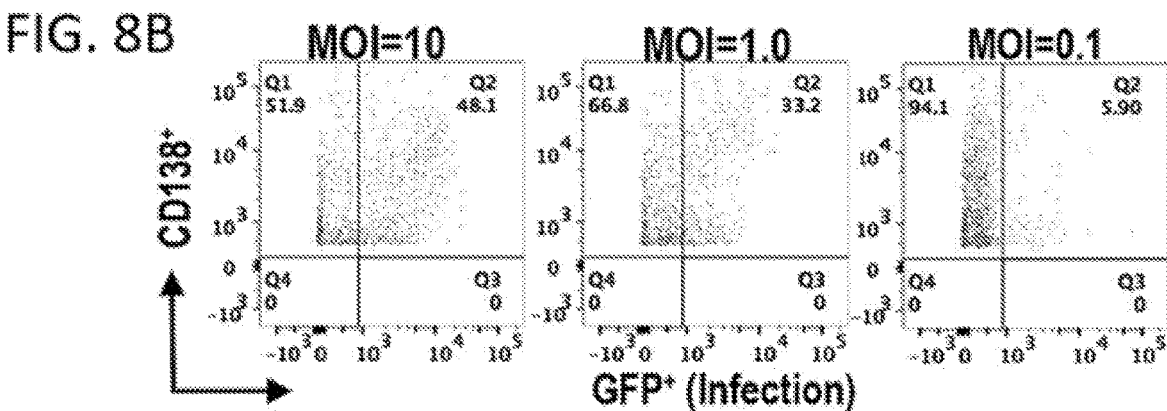
Figure 8C:
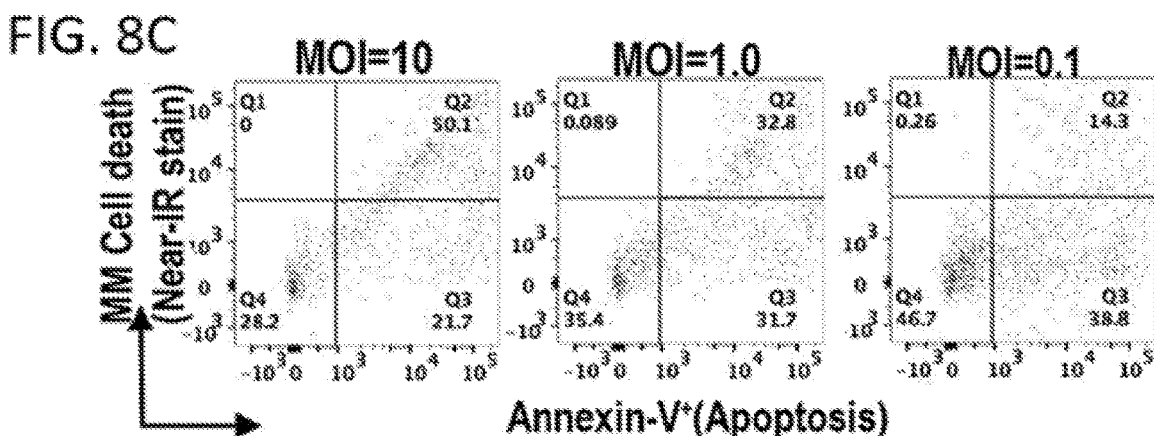
Figure 9A:
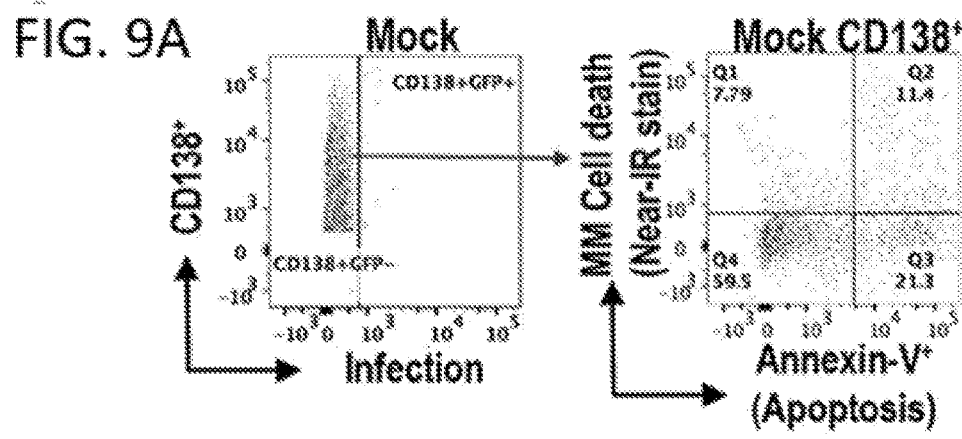
FIGS. 9A and 9B show killing of uninfected multiple myeloma (MM) cells (i.e., GFP−) from a primary human sample from patient #3 after treatment with MYXV-huBiKE-GFP.
Figure 9B:
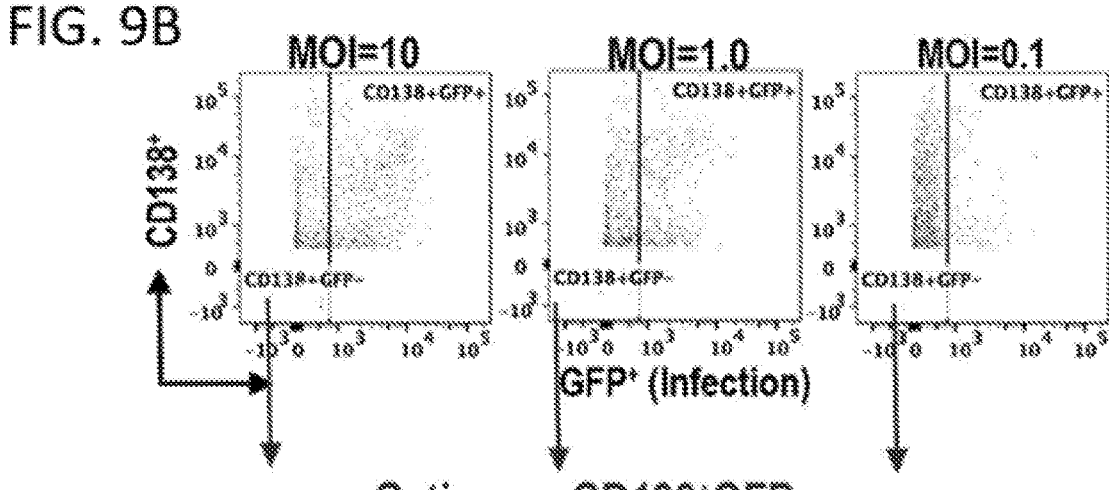
Figure 9B:
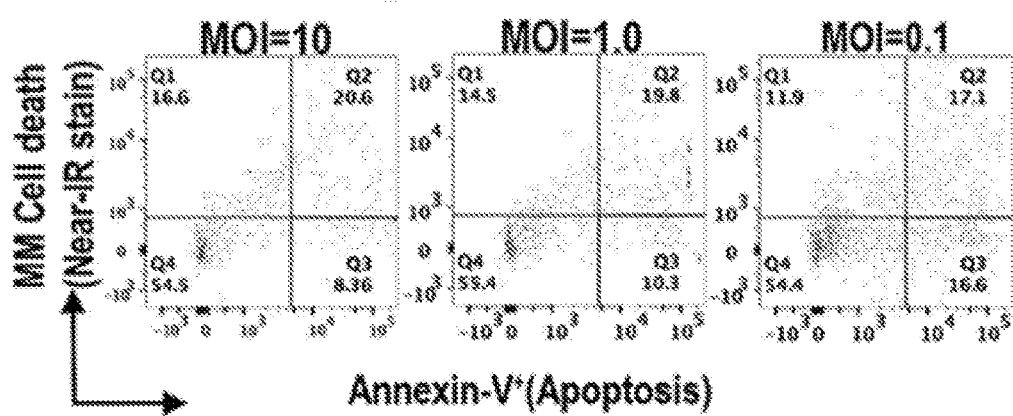

The construction of the recombination plasmids was done by Gateway technology (Multisite Gateway Pro) which allows construction of a single plasmid from multiple DNA fragments by recombination in bacteria. Four entry clones were generated containing different elements to make the final recombination cassette. They are: a) element 1, myxoma virus M135 region; b) element 2, human or mouse LIGHT/TNFSF14 cDNA with poxvirus Syn E/L promoter sequence; c) element 3, reporter gene TdTomato under poxvirus late p11 promoter; d) element 4, firefly luciferase under poxvirus Syn E/L promoter, together with the myxoma virus M136 gene sequence. For making the M135KO virus backbone, element 1 was replaced with a partial sequence from the M134 ORF and 50nt from the M135 ORF. For constructing the final recombination plasmid cassette, all these four elements were recombined with a Gateway destination vector by LR recombination reaction using the standard protocol. The final recombination plasmids were: a) pDEST M135-136-FLuc-muLIGHT-TdTomato, b) pDEST M135-136-huLIGHT-FLuc-TdTomato, c)

pDEST M135KO-Fluc-muLIGHT-TdTomato, and d) pDEST M135KO-FLuc-huLIGHT-TdTomato (FIGS. 3 and 4). At this stage before making the recombinant viruses, the expression of murine or human LIGHT proteins (approximately 26 kDa) under poxvirus promoter was confirmed by Western blot analysis after infection and transfection of the plasmids in the RK13 cells (FIG. 5A). The final recombination plasmids encoding the transgene and selection markers together with the flanking sequences were transfected into RK13 cells that were infected with wild type MYXV Lausanne. Recombinant viruses were isolated from wild-type virus and serially purified based on the expression of selection marker. The transgene expression was again confirmed by Western blot analysis and functional assays (FIG. 5B). The 4 viruses were: a) MYXV-FLuc-huLIGHT-TdTomato, b) MYXV-FLuc-mLIGHT-TdTomato, c) MYXV-M135KO-FLuc-huLIGHT-TdTomato, and d) MYXV-M135KO-FLuc-muLIGHT-tdTomato.

Example 2

In Vitro Studies Using Human Primary Patient Samples Contaminated with Multiple Myeloma (MM) Cells In order to evaluate the susceptibility of primary patient samples contaminated with multiple myeloma (MM) cells from 3 drug-refractory patients to MYXV infection, primary un-manipulated peripheral blood (PB) aspirates from patients 2, 3, and 4 with different levels of MM cells (CD138+) (summarized in Table 5) were subjected to purification using Ficoll-paque plus gradient to isolate mono-nuclear cells and eliminate the majority of red blood cells (RBCs). These primary cells in suspension were then mock-treated (i.e., no virus added), or incubated with MYXV-BiKE-GFP, MYXV-huLIGHT-FLuc-TdTomato or MYXV-mDecorin-GFP constructs as shown in FIGS. 6-13 and Table 6, at different multiplicity of infection (MOI) units including MOI=10, 1, and 0.1 at 37° C. for 1 hour to allow virus adsorption. After this, mock-treated, or MYXV-treated cells were incubated overnight (~24 hours) at 37° C. to allow virus infection. For patient #3, the percentages of virus infection (i.e., using MYXV-FLuc-huLIGHT-TdTomato, or MYXV-huBiKE) at MOI=10, 1.0 and 0.1, as well as percentages of viability, apoptosis, and cell death of MM cells were determined using flow cytometry (FIGS. 6A-C and FIGS. 8A-C). In addition to this, the percentages of viability, apoptosis, and cell death of MM cells in patient samples that were exposed to the virus but were un-infected was evaluated using flow cytometry (FIGS. 7A-B and 9A-B). This allows the measurement of MM cell death in cells that were not directly infected by the virus (i.e. do not express any virus-specific fluorescent protein) but were killed in an "off-target" fashion, e.g., by MYXV-activated leukocytes from the same patient samples.

Figure 10A:
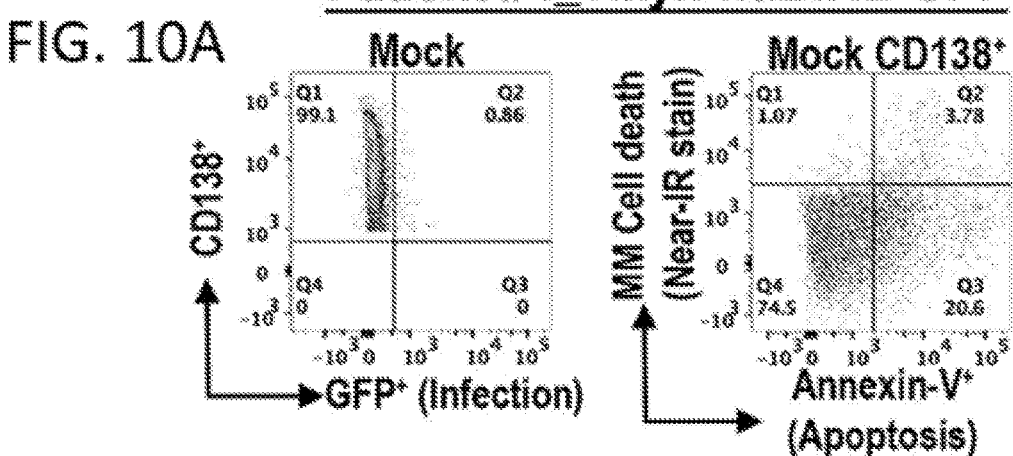
FIGS. 10A-10D show MYXV-huBiKE-GFP productively infects and induces killing of multiple myeloma (MM) cells from a primary human sample from patient #4.
Figure 10B:
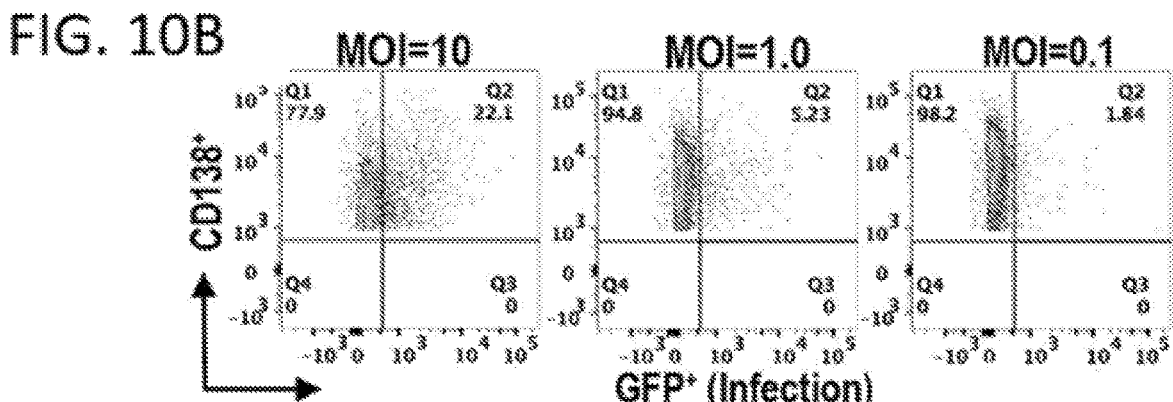
Figure 10C:
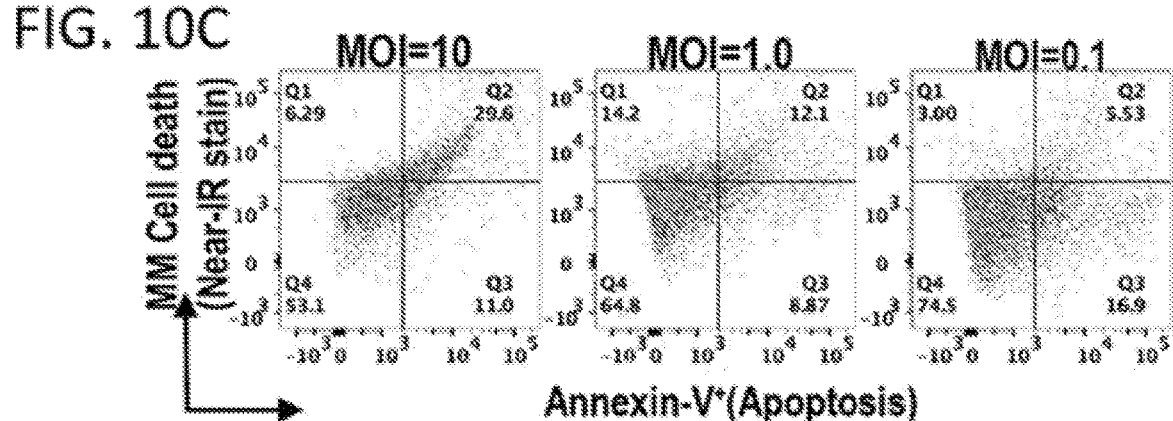
Figure 10D:
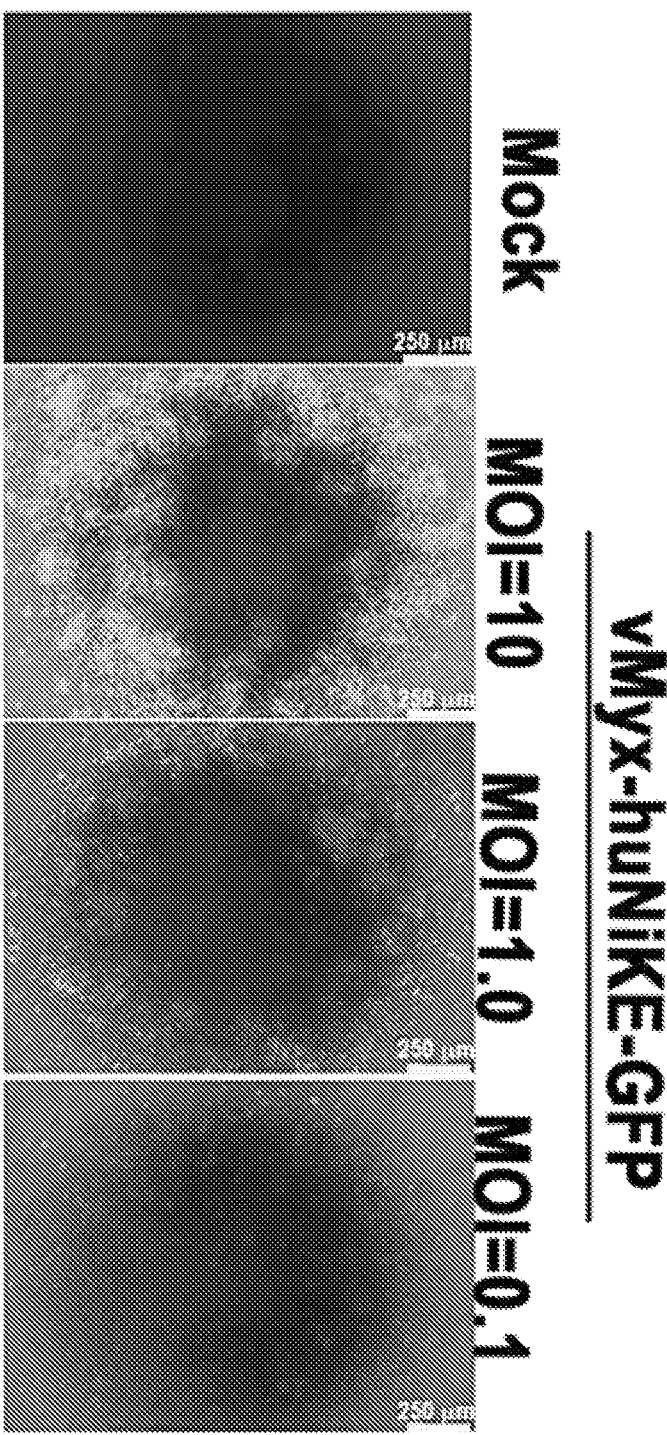
Figure 11A:
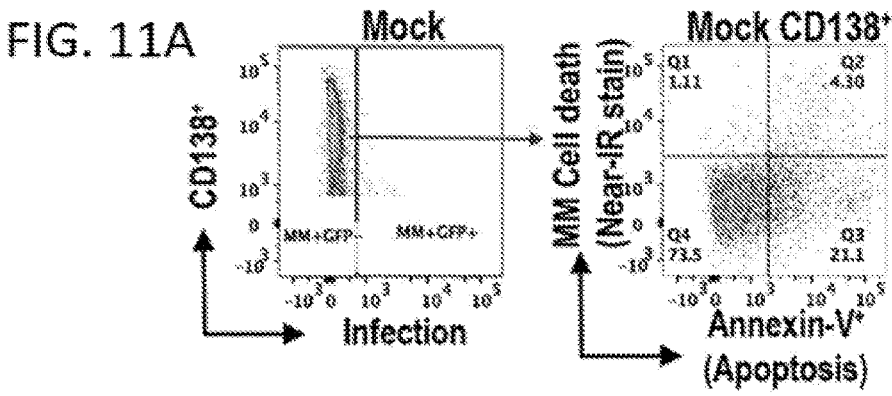
FIGS. 11A and 11B show killing of uninfected multiple myeloma (MM) cells (i.e., GFP⁻) from primary human sample from patient #4 after treatment with MYXV-huBiKE-GFP.
Figure 11B:
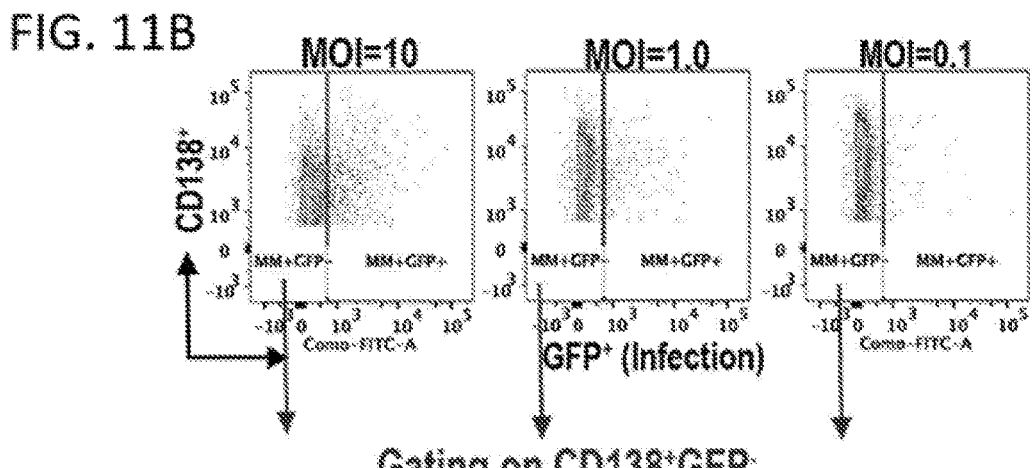
Figure 11B:
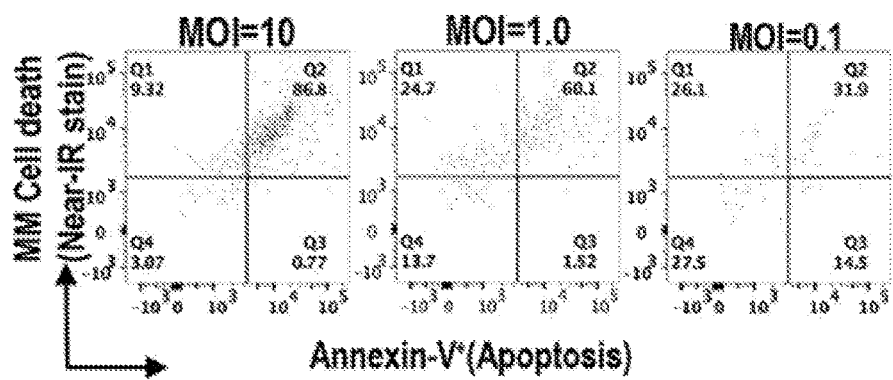
Figure 12A:
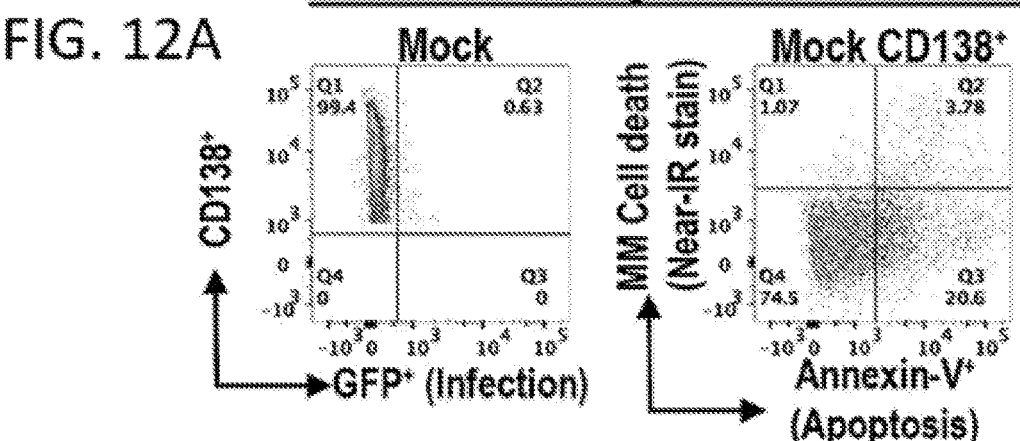
FIGS. 12A-12D shows MYXV-mDecorin-GFP productively infects and induces multiple myeloma (MM) cell killing in a primary human sample from patient #4.
Figure 12B:
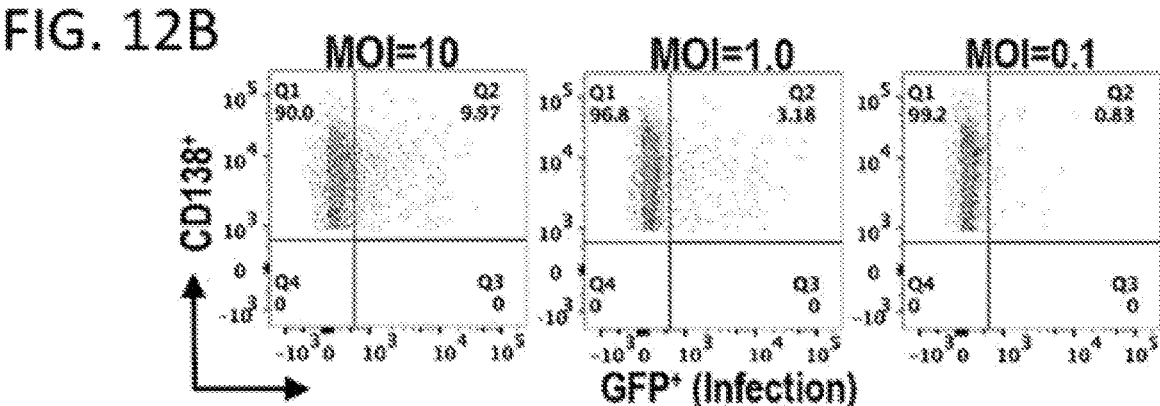
Figure 12C:
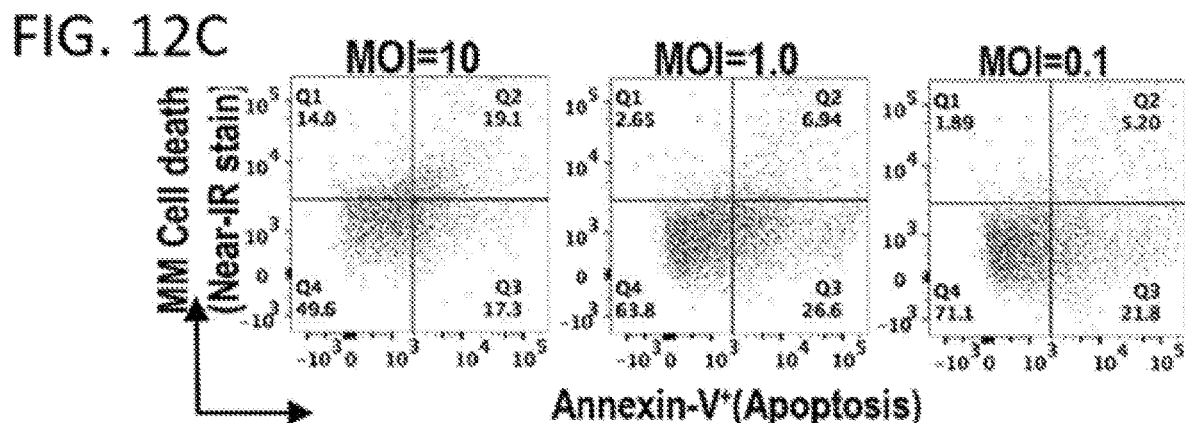
Figure 12D:
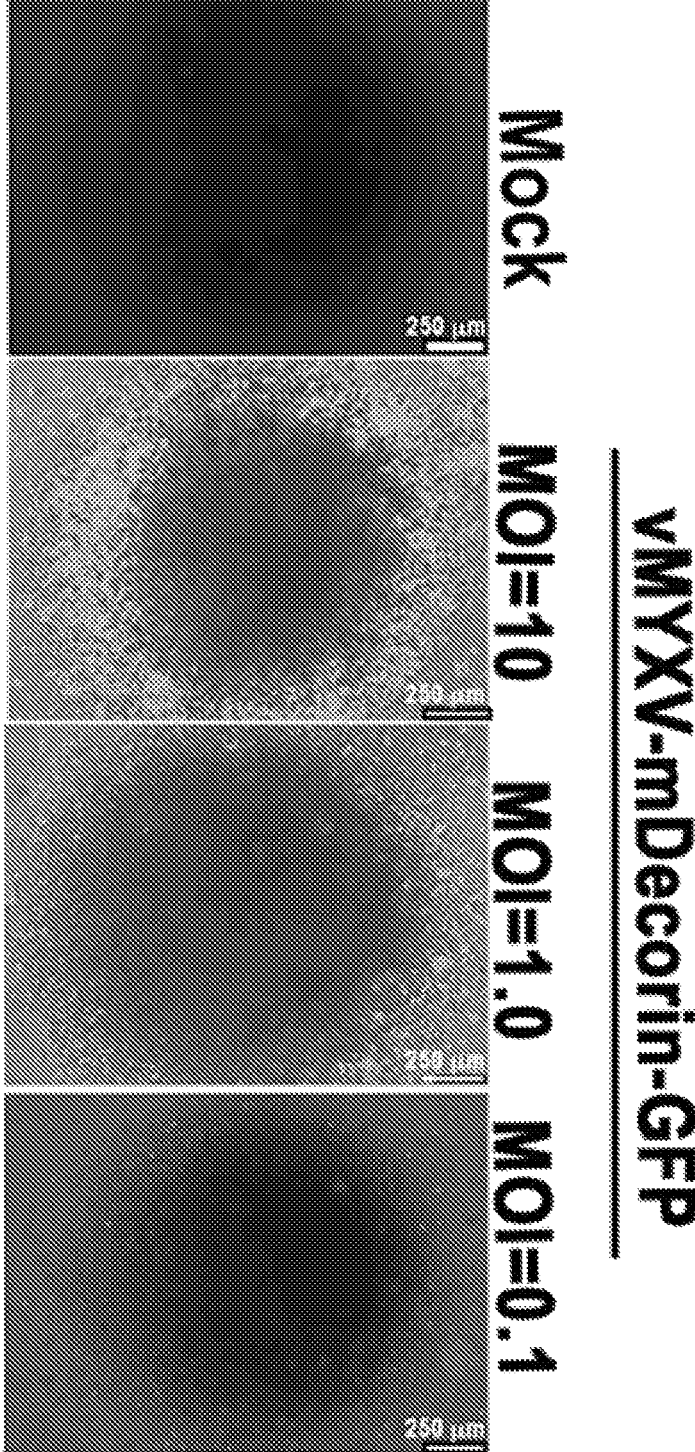

The levels of infection using the MYXV-BiKE-GFP and MYXV-mDecorin-GFP in cells from patient #4 were first evaluated using fluorescence microscopy (FIG. 10D and FIG. 12D, respectively). The percentages of infected, viable, and apoptotic MM cells were determined using flow cytometry (FIG. 10A-C and FIG. 12A-C). Furthermore, the percentages of viability, apoptosis, and cell death of those myeloma cells that were exposed to the virus but were un-infected was evaluated using flow cytometry (FIGS. 11A-B and 12A-B).

CD138 is used as a marker of multiple myeloma (MM) cells. GFP or TdTomato is used as a marker of MYXV-infected cells. Annexin-V is used as a marker of apoptotic cells. Near-IR stain is used as a marker of dead cells.

Tables 2 & 3 summarize the data from patients #3 and #4. Because the amount of CD138+ MM cells in patient 2 was below 1%, the percentages of MM cell infection and cell death could not be determined for the virus constructs that were tested in that patient. The apoptosis and MM cell killing data shown in Table 6 was generated by gating on CD138+ (MM) cells, and data indicate that all of the virus constructs tested can efficiently infect and kill MM cells from within primary human peripheral blood samples derived from drug-refractory patients. Strikingly, for patient #3 the MYXV constructs expressing huLIGHT or BiKE could induce the increased killing of MM cells at all the different MOI's tested (FIGS. 6, 8, and Table 6). For example, 90.8% of cells infected with MYXV expressing huLIGHT at an MOI of 10 were killed, 50.1% of cells infected with MYXV expressing huBiKE at an MOI of 10 were killed, and 6.51-12.99% of mock-treated cells were killed. For patient #4, MYXV expressing BiKE and mDecorin also killed infected MM cells following virus infection (FIGS. 10, 12 and Table 6). For example, 35.9% of cells infected with MYXV expressing BiKE at an MOI of 10 were killed, 33.1% of cells infected with MYXV expressing mDecorin at an MOI of 10 were killed, and 4.85% of mock-treated cells were killed.

Data shown in Table 7 was generated by gating on killing of uninfected MM cells (i.e., CD138+GFP− or CD138+TdTomato−). This "off-target" killing of un-infected MM cells was higher for these virus constructs at all MOIs compared to mock-treated cells (FIGS. 7 and 9 for patient #3 and Table 7 and FIGS. 11 and 12 for patient #4 and Table 7). For example, 96.12% and 32.3% of uninfected cells from patient 4 were killed in experiments where the MYXV constructs had been added to the culture at an MOI of 10, compared to 5.41% of mock-treated cells.

TABLE 5

Percentages of Hu primary MM cells (CD138+)

| Patient # | Patient ID | % MM cells |
|---|---|---|
| 2 | PB208485 | <1.0 |
| 3 | PB208482 | 2.3 |
| 4 | PB208560 | 15.0 |

TABLE 6

Percentages of infection, apoptosis and cell death of hu-primary MM cells (CD138+).

| Patient # 3 ID PB208482 + MYXV | % Infection of MM (CD138+GFP+ or CD138+TdTomato+) at MOI = 10, 1.0, 0.1 | Annexin V− Near-IR+ at MOI = 10, 1.0, 0.1 | Annexin V+ Near-IR+ at MOI = 10, 1.0, 0.1 | Total Near-IR+ at MOI = 10, 1.0, 0.1 |
|---|---|---|---|---|
| MYXV-huBiKE-GFP | 48.10, 33.20, 5.90 | 0.00, 0.089, 0.26 | 50.10, 32.80, 14.3 | 50.10, 32.90, 14.56 |

TABLE 6-continued

Percentages of infection, apoptosis and cell death of hu-primary MM cells (CD138+).

| MYXV-FLuc- | 57.60, | 34.80, | 56.0, | 90.80, |
|---|---|---|---|---|
| huLIGHT- | 15.50, | 6.55, | 48.80, | 55.35, |
| TdTomato | 5.32 | 4.95 | 31.20 | 36.15 |
| Patient # 3 ID PB208482 | % Infection | Annexin V– Near-IR+ | Annexin V+ Near-IR+ | Total Near-IR+ |
| Mock control of Hu BIKE | 0.83 | 0.91 | 5.60 | 6.51 |
| Mock control of huLIGHT | 0.98 | 1.39 | 11.60 | 12.99 |

| Patient # 4 ID PB208560 + MYXV | % Infection of MM (CD138+GFP+ or CD138+TdTomato+) at MOI = 10, 1.0, 0.1 | Annexin V– Near-IR+ MOI = 10, 1.0, 0.1 | Annexin V+ Near-IR+ at MOI = 10, 1.0, 0.1 | Total Near-IR+ MOI = 10, 1.0, 0.1 |
|---|---|---|---|---|
| MYXV-huBiKE-GFP | 22.10, 5.23, 1.84 | 6.29, 14.20, 3.00 | 29.6,0 12.10, 5.53 | 35.90, 26.30, 8.53 |
| MYXV-mDecorin-GFP | 9.97, 3.20, 0.83 | 14.00, 2.65, 1.89 | 19.10, 6.94, 5.20 | 33.10, 9.59, 7.09 |
| Patient # 4 ID PB208560 | % Infection | Annexin V– Near-IR+ | Annexin V+ Near-IR+ | Total Near-IR+ |
| Mock control for huBiKE | 0.86 | 1.07 | 3.78 | 4.85 |
| Mock control for mDecorin | 0.63 | 1.07 | 3.78 | 4.85 |

TABLE 7

Percentages of viability infection, apoptosis and cell death of un-infected hu-primary MM cells (CD138+) as assessed by gating on MM cells that are GFP− or TdTomato−

| Patient # 3 ID PB208482 + MYXV | Annexin V– Near-IR+ MOI = 10, 1.0, 0.1 | Annexin V+ Near-IR+ at MOI = 10, 1.0, 0.1 | Total Near-IR+ at MOI = 10, 1.0, 0.1 |
|---|---|---|---|
| MYXV-huBiKE-GFP | 16.60, 14.50, 11.90 | 20.60, 19.70, 17.10 | 37.20, 34.30, 29.00 |
| MYXV-FLuc-huLIGHT-TdTomato | 64.50, 23.30, 20.10 | 20.30, 58.50, 46.90 | 84.80, 81.80, 67.00 |
| Patient # 3 ID PB208482 Mock | Annexin V– Near-IR+ 7.79 | Annexin V+ Near-IR+ 11.4 | Total Near-IR+ 19.200 |

| Patient # 4 ID PB208560 + MYXV | Annexin V– Near-IR+ MOI = 10, 1.0, 0.1 | Annexin V+ Near-IR+ at MOI = 10, 1.0,0.1 | Total Near-IR+ at MOI = 10, 1.0, 0.1 |
|---|---|---|---|
| MYXV-huBiKE-GFP | 9.32, 24.70, 26.10 | 86.8, 60.1, 31.9 | 96.12, 84.80, 58.00 |
| MYXV-mDecorin-GFP | 15.00, 3.01, 2.06 | 17.30, 7.41, 5.90 | 32.30, 10.42, 7.96 |
| Patient # 4 ID PB208560 Mock | Annexin V– Near-IR+ 1.11 | Annexin V+ Near-IR+ 4.30 | Total Near-IR+ 5.41 |

Example 3: Oncolytic Virotherapy with Myxoma Virus (MYXV) Against Multiple ID-, Myeloma (MM): Identification of MYXV Constructs Suitable for Eliminating Contaminating Cancer Cells from Primary Human Samples Experiments are conducted to identify MYXV constructs and experimental conditions suitable for eliminating contaminating refractory cancer cells from primary human cell samples. Bone marrow or peripheral blood samples are obtained from a subject with a hematological cancer (e.g., a myeloma, a leukemia, or a lymphoma). Mononuclear cells are isolated (e.g., via Ficoll-Paque). Samples of mononuclear cells comprising cancer cells are treated with MYXV constructs of the disclosure (e.g., comprising different transgenes and/or deletions) under various conditions (e.g., MOI, incubation time), and the ability of the MYXV constructs to kill cancer cells is determined as disclosed herein (e.g., via flow cytometry, fluorescence microscopy, and/or cytotoxicity assay).

The identified construct and/or experimental conditions can be used for treating the subject. For example, A MYXV construct identified as suitable can be directly administered to the subject (e.g., via injection or intravenous infusion), or can be administered via MYXV-adsorbed leukocytes.

Example 4: Oncolytic Virotherapy with a Myxoma Virus (MYXV)

A subject is identified as having a hematological cancer (e.g., a myeloma, leukemia, or lymphoma). The hematological cancer can optionally be a hematological cancer that comprises minimal residual disease (MRD) and/or drug-resistant MRD.

Optionally, studies are conducted to identify a MYXV construct of the disclosure that eliminates cancer cells from a sample taken from the subject (e.g., a peripheral blood or bone marrow sample).

A MYXV is administered to the subject (e.g., administered via injection or infusion). The MYXV infects cancer cells in the subject, leading to cancer cell killing and an anti-cancer immune response.

Example 5: Oncolytic Virotherapy with Myxoma Virus (MYXV) Via Autologous Transplant of MYXV-Adsorbed Leukocytes A MYXV is administered to a subject with a hematological cancer via autologous transplant of MYXV-adsorbed leukocytes.

Bone marrow or peripheral blood samples are obtained from a subject with a hematological cancer (e.g., a myeloma, leukemia, or lymphoma), and mononuclear cells are isolated (e.g., via Ficoll-Paque). Cancer cells can be separated from non-cancer cells (e.g., via FACS or MACS). A MYXV of the disclosure is adsorbed to leukocytes (for example, adsorbed for about an hour at an MOI of about 0.1 to 10). The MYXV-adsorbed leukocytes are administered back to the subject via intravenous infusion. The MYXV infects cancer cells in the subject, leading to cancer cell killing and an anti-cancer immune response.

Example 6: Oncolytic Virotherapy with Myxoma Virus (MYXV) Via Allogenic Transplant of MYXV-Adsorbed Leukocytes A MYXV is administered to a subject with a hematological cancer (e.g., a myeloma, leukemia, or lymphoma) via allogenic transplant of MYXV-adsorbed leukocytes. Bone marrow or peripheral blood samples are obtained from a donor (e.g., an HLA-matched, HLA-mismatched, haploidentical, or sibling donor, or a combination thereof). Mononuclear cells are isolated (e.g., via Ficoll-Paque). Optionally, cells are purified or enriched for specific leukocyte subsets (e.g., via FACS or MACS). A MYXV of the disclosure is adsorbed to leukocytes (for example, adsorbed for about an hour at an MOI of about 0.1 to 10). The MYXV-adsorbed leukocytes are administered back to the subject via intravenous infusion. The MYXV infects cancer cells in the subject, leading to cancer cell killing and an anti-cancer immune response.

Example 7: Ex Vivo MYXV Virotherapy in Conjunction with Auto-Transplants in the Vk*MYC Immunocompetent Mouse Model of Minimal Residual Disease (MRD) to Target and Eliminate Drug-Resistant Disseminated MM In Vivo Two C57BL/6-derived VK*MYC cell lines were used for the in vivo experiments: VK12598, which is bortezomib-resistant (BOR-resistant), and the multi-drug resistant line VK12653. First, the susceptibility of these two VK*MYC cell lines to MYXV binding and infection was evaluated.

MYXV binding to VK12598 and VK12653, in vitro studies: For binding experiments, MYXV-M093L-Venus virus (comprising a fusion of the fluorescent protein Venus at the amino terminus of M093L) was used at a multiplicity of infection (MOI) of 10. In brief, either VK12598, or VK12653 were freshly isolated from BM (or from freshly-thawed BM), and incubated with MYXV-M093L-Venus at 4° C. for 1 hour to allow virus binding. Unbound virus was removed by washing the virus-adsorbed cells twice. Levels of virion binding were quantified using flow cytometry. For analyses of virus infection, cells were incubated with reporter MYXV-GFP(E/L)/TdTomato(L) at MOI=10 for 1 hour at 37° C. to allow virus adsorption. Cells were incubated overnight at 37° C. to allow virus infection. MYXV efficiently bound to both cell lines (FIGS. 14A and 15A). In addition to this, MYXV productively infects both cell lines (FIGS. 14B-C and 15B).

In vivo studies using the VK12598 cell line: In the first in vivo experiment, C57BL/6 mice were pre-seeded with VK12598 cells (e.g., $1 \times 10^6$ cells per mouse). Four weeks post-MM cell implantation, mice were subjected to bleeding and the M-Spike was measured. Mice were separated according to the levels of M-Spike (e.g., 0, low=0.1, medium=0.2, high=0.6) (FIG. 16A, Top panel). Mice were then treated as follows: No C57BL/6 BM transplant (Cohort I), C57BL/6 BM cells alone (Cohort II), MYXV-M135KO-GFP alone (Cohort III), C57BL/6 BM ex vivo treated with MYXV-M135KO-GFP (Cohort IV) (FIG. 16A, bottom panel). FIG. 16B shows the percentage of MM (CD138$^+$ B220$^-$) in a representative mouse from Cohort I with low M-spike (0.1) and the percentage of MM (CD138$^+$B220$^-$) in a representative mouse from Cohort II with high M-spike (0.6). FIG. 16C shows the M-spike of the only survivor from Cohort IV, which exhibited total regression of MM, with no M-spike band detected on day 8, day 29, and day 37 post-transplant. These data indicate that a transplant of ex vivo MYXV-treated bone marrow can induce MM regression. Together, these data also indicate that the cohort treatment in this first experiment started too late in the disease progression, and instead virotherapy should be started much earlier in this model (e.g. less than 1 week post-MM implantation rather than 4 weeks post-MM implantation). Although MM regression can occur even at this late intervention time, starting virotherapy earlier (e.g., in mouse cohorts that are not so close to death or end-point) may allow improved evaluation of the virus technology.

In additional trial, MYXV is tested in combination with other therapeutics (such as the SMAC mimetic LC161). VK12598 cancer cells are implanted, M-Spike quantified at 1-4 weeks, and the mice are treated with cyclophosphamide to induce a transient complete response (CR), which can last 1 month. At either one or two weeks post cyclophosphamide, the mice are transplanted with BM+MYXV or PBMC+MYXV (e.g., MYXV expressing an immunomodulatory transgene as disclosed herein) in order to test if the virotherapy can extend or complete the partial regression initiated by the cyclophosphamide. In this setting, the capacity of MYXV to eliminate MM minimal residual disease (MRD) as defined by disease that functionally resists this chemotherapy is investigated. The capacity of MYXV to eliminate the multidrug-resistant VK12653 cells line, either as a monotherapy or in combination therapy is also investigated.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

---

We claim:

1. A myxoma virus (MXYV) comprising one or more immunomodulatory transgenes, wherein the one or more immunomodulatory transgenes encode a BiKE (Bi-specific Natural Killer and Neutrophil engager), wherein the BiKE comprises a first single chain variable fragment (scFv) that binds to CD16 and a second scFv that binds to a cancer-specific cell surface marker, wherein the cancer-specific cell surface marker is CD138, wherein the BiKE comprises SEQ ID NO:6.

2. The MYXV of claim 1, wherein the immunomodulatory transgene is inserted in the MYXV genome within or adjacent to a gene that modulates MYXV replication in a cancer cell, a gene that is associated with an ability of the MYXV to cause disease in a host animal, a gene that is associated with host cell tropism, a gene that is associated with an ability of the MYXV to evade an innate immune response, a gene that modulates immune signaling in an infected cell, or a gene that modulates a cell death pathway in an infected cell.

3. The MYXV of claim 1, wherein the one or more immunomodulatory transgenes further comprise a LIGHT (Lymphotoxins-like, exhibits Inducible expression, and competes with HSV Glycoprotein D for Herpesvirus entry mediator (HVEM), a receptor expressed by T lymphocytes).

4. The MYXV of claim 3, wherein the LIGHT comprises SEQ ID NO: 13.

5. The MYXV of claim 1, wherein the one or more immunomodulatory transgenes further comprise a decorin.

6. The MYXV of claim 5, wherein the decorin comprises SEQ ID NO: 7.

7. The MYXV of claim 1, wherein the immunomodulatory transgene is inserted between M135 and M136 open reading frames of the MYXV genome.

8. The MYXV of claim 1, wherein the MYXV comprises a gene deletion or disruption in its genome.

9. The MYXV of claim 8, wherein the gene deletion or disruption is present in one or more genes selected from the group consisting of M001R, M002R, M003.1R, M003.2R, M004.1R, M004R, M005R, M006R, M007R, M008.1R, M008R, M009L, M013, M036L, M063L, M11L, M128L, M131R, M135R, M136R, M141R, M148R, M151R, M152R, M153R, M154L, M156R, M-T2, M-T4, M-T5, M-T7, and SOD.

10. The MYXV of claim 1, wherein the MYXV is a genetically modified Laussane strain MYXV.

11. The MYXV of claim 1, wherein the MYXV is capable of infecting and killing cancer cells from a subject with drug-refractory cancer.

12. The MYXV of claim 1, wherein the MYXV is capable of directly killing cancer cells infected by the MYXV and eliciting off-target killing of uninfected cancer cells.

\* \* \* \* \*

```
                          SEQUENCE LISTING

<160> NUMBER OF SEQ ID NOS: 43

<210> SEQ ID NO 1
<211> LENGTH: 87
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggggacaact tttctataca aagttgccaa aattgaaatt ttattttttt tttttggaat      60
ataaataatg aaggcaactc tcatctt                                         87

<210> SEQ ID NO 2
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggggacaact ttattataca aagttgttta agaatcgaga ccgaggagag ggttagggat      60
aggcttaccc ttgtagtttc caagttgaa                                       89

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcagcaagga cacatcctct aa                                              22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taaggatcct cattggactg c                                               21

<210> SEQ ID NO 5
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaagagcc agacccaggt gttcatcttc ctgctgctgt gcgtgagcgg cgcccacggc     60
gacatccaga tgacccagag caccagcagc ctgagcgcca gcctgggcga cagggtgacc    120
```

```
atcagctgca gcgccagcca gggcatcaac aactacctga actggtacca gcagaagccc      180
gacggcaccg tggagctgct gatctactac accagcaccc tgcagagcgg cgtgcccagc      240
aggttcagcg gcagcggcag cggcaccgac tacagcctga ccatcagcaa cctggagccc      300
gaggacatcg gcacctacta ctgccagcag tacagcaagc tgcccaggac cttcggcggc      360
ggcaccaagc tggagatcaa gggtggcggt ggctccggcg gtggtgggtc gggtggcggc      420
ggatctagcc aggtgcagct gcagcagagc ggcagcgagc tgatgatgcc cggcgccagc      480
gtgaagatca gctgcaaggc caccggctac accttcagca actactggat cgagtgggtg      540
aagcagaggc ccgccacggg cctggagtgg atcggcgaga tcctgcccgg caccggcagg      600
accatctaca cgagaagtt caagggcaag gccaccttca ccgccgacat cagcagcaac      660
accgtgcaga tgcagctgag cagcctgacc agcgaggaca cgccgtgta ctactgcgcc      720 aggagggact actacggcaa cttctactac gccatggact actggggcca gggcaccagc      780
gtgaccgtga gcagcggtgg cggtggctcc ggcggtggtg ggtcgcaggt tactctgaaa      840
gagtctggcc ctgggatatt gcagccctcc cagaccctca gtctgacttg ttctttctct      900
gggttttcac tgaggacttc tggtatgggg gtaggctgga ttcgtcagcc ttcagggaag      960
ggtctagagt ggctggcaca catttggtgg gatgatgaca agcgctataa tccagccctg     1020
aagagccgac tgacaatctc caaggatacc tccagcaacc aggtattcct caaaatcgcc     1080
agtgtggaca ctgcagatac tgccacatac tactgtgctc aaataaaccc cgcctggttt     1140
gcttactggg gccaagggac tctggtcact gtctctgccg gtggcggtgg ctccggcggt     1200
ggtgggtcgg gtggcggcgg atctgacact gtgctgaccc aatctccagc ttctttggct     1260
gtgtctctag gcagagggc caccatctcc tgcaaggcca gccaaagtgt tgattttgat     1320
ggtgatagtt ttatgaactg gtaccaacag aaaccaggac agccacccaa actcctcatc     1380
tatactacat ccaatctaga atctgggatc ccagccaggt ttagtgccag tgggtctggg     1440
acagacttca ccctcaacat ccatcctgtg gaggaggagg atactgcaac ctattactgt     1500
cagcaaagta atgaggatcc gtacacgttc ggaggggga ccaagctgga aataaaaggt     1560
aagcctatcc ctaaccctct cctcggtctc gattctacgt aa                        1602
```

<210> SEQ ID NO 6
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Lys Ser Gln Thr Gln Val Phe Ile Phe Leu Leu Leu Cys Val Ser
1               5                   10                  15

Gly Ala His Gly Asp Ile Gln Met Thr Gln Ser Thr Ser Ser Leu Ser
            20                  25                  30

Ala Ser Leu Gly Asp Arg Val Thr Ile Ser Cys Ser Ala Ser Gln Gly
        35                  40                  45

Ile Asn Asn Tyr Leu Asn Trp Tyr Gln Gln Lys Pro Asp Gly Thr Val
    50                  55                  60

Glu Leu Leu Ile Tyr Tyr Thr Ser Thr Leu Gln Ser Gly Val Pro Ser
65                  70                  75                  80

Arg Phe Ser Gly Ser Gly Ser Gly Thr Asp Tyr Ser Leu Thr Ile Ser
                85                  90                  95
```

-continued

```
Asn Leu Glu Pro Glu Asp Ile Gly Thr Tyr Tyr Cys Gln Gln Tyr Ser
            100                 105                 110

Lys Leu Pro Arg Thr Phe Gly Gly Gly Thr Lys Leu Glu Ile Lys Gly
            115                 120                 125

Gly Gly Gly Ser Gly Gly Gly Gly Ser Gly Gly Gly Gly Ser Ser Gln
            130                 135                 140

Val Gln Leu Gln Gln Ser Gly Ser Glu Leu Met Met Pro Gly Ala Ser
145                 150                 155                 160

Val Lys Ile Ser Cys Lys Ala Thr Gly Tyr Thr Phe Ser Asn Tyr Trp
                165                 170                 175

Ile Glu Trp Val Lys Gln Arg Pro Gly His Gly Leu Glu Trp Ile Gly
            180                 185                 190

Glu Ile Leu Pro Gly Thr Gly Arg Thr Ile Tyr Asn Glu Lys Phe Lys
            195                 200                 205

Gly Lys Ala Thr Phe Thr Ala Asp Ile Ser Ser Asn Thr Val Gln Met
            210                 215                 220

Gln Leu Ser Ser Leu Thr Ser Glu Asp Ser Ala Val Tyr Tyr Cys Ala
225                 230                 235                 240

Arg Arg Asp Tyr Tyr Gly Asn Phe Tyr Tyr Ala Met Asp Tyr Trp Gly
                245                 250                 255

Gln Gly Thr Ser Val Thr Val Ser Ser Gly Gly Gly Gly Ser Gly Gly
            260                 265                 270

Gly Gly Ser Gln Val Thr Leu Lys Glu Ser Gly Pro Gly Ile Leu Gln
            275                 280                 285

Pro Ser Gln Thr Leu Ser Leu Thr Cys Ser Phe Ser Gly Phe Ser Leu
            290                 295                 300

Arg Thr Ser Gly Met Gly Val Gly Trp Ile Arg Gln Pro Ser Gly Lys
305                 310                 315                 320

Gly Leu Glu Trp Leu Ala His Ile Trp Trp Asp Asp Asp Lys Arg Tyr
                325                 330                 335

Asn Pro Ala Leu Lys Ser Arg Leu Thr Ile Ser Lys Asp Thr Ser Ser
            340                 345                 350

Asn Gln Val Phe Leu Lys Ile Ala Ser Val Asp Thr Ala Asp Thr Ala
            355                 360                 365

Thr Tyr Tyr Cys Ala Gln Ile Asn Pro Ala Trp Phe Ala Tyr Trp Gly
    370                 375                 380

Gln Gly Thr Leu Val Thr Val Ser Ala Gly Gly Gly Gly Ser Gly Gly
385                 390                 395                 400

Gly Gly Ser Gly Gly Gly Gly Ser Asp Thr Val Leu Thr Gln Ser Pro
                405                 410                 415

Ala Ser Leu Ala Val Ser Leu Gly Gln Arg Ala Thr Ile Ser Cys Lys
            420                 425                 430

Ala Ser Gln Ser Val Asp Phe Asp Gly Asp Ser Phe Met Asn Trp Tyr
            435                 440                 445

Gln Gln Lys Pro Gly Gln Pro Pro Lys Leu Leu Ile Tyr Thr Thr Ser
            450                 455                 460

Asn Leu Glu Ser Gly Ile Pro Ala Arg Phe Ser Ala Ser Gly Ser Gly
465                 470                 475                 480

Thr Asp Phe Thr Leu Asn Ile His Pro Val Glu Glu Glu Asp Thr Ala
                485                 490                 495

Thr Tyr Tyr Cys Gln Gln Ser Asn Glu Asp Pro Tyr Thr Phe Gly Gly
            500                 505                 510
```

```
Gly Thr Lys Leu Glu Ile Lys Gly Lys Pro Ile Pro Asn Pro Leu Leu
        515                 520                 525

Gly Leu Asp Ser Thr
    530

<210> SEQ ID NO 7
<211> LENGTH: 359
<212> TYPE: PRT
<213> ORGANISM: Homo sapiens

<400> SEQUENCE: 7

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Leu Asp Lys Val Pro Lys Asp Leu Pro
65              70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
            115                 120                 125

Val Lys Leu Glu Arg Leu Tyr Leu Ser Lys Asn Gln Leu Lys Glu Leu
    130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
            195                 200                 205

Asp Thr Asn Ile Thr Ser Ile Pro Gln Gly Leu Pro Pro Ser Leu Thr
    210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
    275                 280                 285

Ala Glu His Lys Tyr Ile Gln Val Val Tyr Leu His Asn Asn Asn Ile
    290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
            325                 330                 335

Trp Glu Ile Gln Pro Ser Thr Phe Arg Cys Val Tyr Val Arg Ser Ala
            340                 345                 350
```

-continued

```
Ile Gln Leu Gly Asn Tyr Lys
        355

<210> SEQ ID NO 8
<211> LENGTH: 250
<212> TYPE: PRT
<213> ORGANISM: Homo sapiens

<400> SEQUENCE: 8

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Glu Leu Gly Thr Asn Pro Leu Lys Ser Ser
65                  70                  75                  80

Gly Ile Glu Asn Gly Ala Phe Gln Gly Met Lys Lys Leu Ser Tyr Ile
                85                  90                  95

Arg Ile Ala Asp Thr Asn Ile Thr Ser Ile Pro Gln Gly Leu Pro Pro
            100                 105                 110

Ser Leu Thr Glu Leu His Leu Asp Gly Asn Lys Ile Ser Arg Val Asp
        115                 120                 125

Ala Ala Ser Leu Lys Gly Leu Asn Asn Leu Ala Lys Leu Gly Leu Ser
    130                 135                 140

Phe Asn Ser Ile Ser Ala Val Asp Asn Gly Ser Leu Ala Asn Thr Pro
145                 150                 155                 160

His Leu Arg Glu Leu His Leu Asp Asn Asn Lys Leu Thr Arg Val Pro
            165                 170                 175

Gly Gly Leu Ala Glu His Lys Tyr Ile Gln Val Val Tyr Leu His Asn
            180                 185                 190

Asn Asn Ile Ser Val Val Gly Ser Ser Asp Phe Cys Pro Pro Gly His
        195                 200                 205

Asn Thr Lys Lys Ala Ser Tyr Ser Gly Val Ser Leu Phe Ser Asn Pro
    210                 215                 220

Val Gln Tyr Trp Glu Ile Gln Pro Ser Thr Phe Arg Cys Val Tyr Val
225                 230                 235                 240

Arg Ser Ala Ile Gln Leu Gly Asn Tyr Lys
                245                 250

<210> SEQ ID NO 9
<211> LENGTH: 212
<212> TYPE: PRT
<213> ORGANISM: Homo sapiens

<400> SEQUENCE: 9

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60
```

-continued

```
Val Gln Cys Ser Asp Leu Gly Leu Pro Pro Ser Leu Thr Glu Leu His
65                  70                  75                  80

Leu Asp Gly Asn Lys Ile Ser Arg Val Asp Ala Ala Ser Leu Lys Gly
                85                  90                  95

Leu Asn Asn Leu Ala Lys Leu Gly Leu Ser Phe Asn Ser Ile Ser Ala
            100                 105                 110

Val Asp Asn Gly Ser Leu Ala Asn Thr Pro His Leu Arg Glu Leu His
        115                 120                 125

Leu Asp Asn Asn Lys Leu Thr Arg Val Pro Gly Gly Leu Ala Glu His
    130                 135                 140

Lys Tyr Ile Gln Val Val Tyr Leu His Asn Asn Asn Ile Ser Val Val
145                 150                 155                 160

Gly Ser Ser Asp Phe Cys Pro Pro Gly His Asn Thr Lys Lys Ala Ser
                165                 170                 175

Tyr Ser Gly Val Ser Leu Phe Ser Asn Pro Val Gln Tyr Trp Glu Ile
            180                 185                 190

Gln Pro Ser Thr Phe Arg Cys Val Tyr Val Arg Ser Ala Ile Gln Leu
        195                 200                 205

Gly Asn Tyr Lys
    210
```

```
<210> SEQ ID NO 10
<211> LENGTH: 172
<212> TYPE: PRT
<213> ORGANISM: Homo sapiens

<400> SEQUENCE: 10
```

```
Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Val Val Tyr Leu
            100                 105                 110

His Asn Asn Asn Ile Ser Val Val Gly Ser Ser Asp Phe Cys Pro Pro
        115                 120                 125

Gly His Asn Thr Lys Lys Ala Ser Tyr Ser Gly Val Ser Leu Phe Ser
    130                 135                 140

Asn Pro Val Gln Tyr Trp Glu Ile Gln Pro Ser Thr Phe Arg Cys Val
145                 150                 155                 160

Tyr Val Arg Ser Ala Ile Gln Leu Gly Asn Tyr Lys
                165                 170
```

```
<210> SEQ ID NO 11
<211> LENGTH: 75
<212> TYPE: PRT
<213> ORGANISM: Homo sapiens

<400> SEQUENCE: 11
```

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Cys Leu Pro Ser
65                  70                  75

<210> SEQ ID NO 12
<211> LENGTH: 354
<212> TYPE: PRT
<213> ORGANISM: Mus sp.

<400> SEQUENCE: 12

Met Lys Ala Thr Leu Ile Phe Phe Leu Leu Ala Gln Val Ser Trp Ala
1               5                   10                  15

Gly Pro Phe Glu Gln Arg Gly Leu Phe Asp Phe Met Leu Glu Asp Glu
            20                  25                  30

Ala Ser Gly Ile Ile Pro Tyr Asp Pro Asp Asn Pro Leu Ile Ser Met
        35                  40                  45

Cys Pro Tyr Arg Cys Gln Cys His Leu Arg Val Val Gln Cys Ser Asp
    50                  55                  60

Leu Gly Leu Asp Lys Val Pro Trp Asp Phe Pro Pro Asp Thr Thr Leu
65                  70                  75                  80

Leu Asp Leu Gln Asn Asn Lys Ile Thr Glu Ile Lys Glu Gly Ala Phe
                85                  90                  95

Lys Asn Leu Lys Asp Leu His Thr Leu Ile Leu Val Asn Asn Lys Ile
            100                 105                 110

Ser Lys Ile Ser Pro Glu Ala Phe Lys Pro Leu Val Lys Leu Glu Arg
            115                 120                 125

Leu Tyr Leu Ser Lys Asn Gln Leu Lys Glu Leu Pro Glu Lys Met Pro
    130                 135                 140

Arg Thr Leu Gln Glu Leu Arg Val His Glu Asn Glu Ile Thr Lys Leu
145                 150                 155                 160

Arg Lys Ser Asp Phe Asn Gly Leu Asn Asn Val Leu Val Ile Glu Leu
                165                 170                 175

Gly Gly Asn Pro Leu Lys Asn Ser Gly Ile Glu Asn Gly Ala Phe Gln
            180                 185                 190

Gly Leu Lys Ser Leu Ser Tyr Ile Arg Ile Ser Asp Thr Asn Ile Thr
            195                 200                 205

Ala Ile Pro Gln Gly Leu Pro Thr Ser Leu Thr Glu Val His Leu Asp
    210                 215                 220

Gly Asn Lys Ile Thr Lys Val Asp Ala Pro Ser Leu Lys Gly Leu Ile
225                 230                 235                 240

Asn Leu Ser Lys Leu Gly Leu Ser Phe Asn Ser Ile Thr Val Met Glu
                245                 250                 255

Asn Gly Ser Leu Ala Asn Val Pro His Leu Arg Glu Leu His Leu Asp
            260                 265                 270

Asn Asn Lys Leu Leu Arg Val Pro Ala Gly Leu Ala Gln His Lys Tyr
            275                 280                 285

Ile Gln Val Val Tyr Leu His Asn Asn Asn Ile Ser Ala Val Gly Gln

-continued

```
          290                 295                 300

Asn Asp Phe Cys Arg Ala Gly His Pro Ser Arg Lys Ala Ser Tyr Ser
305                 310                 315                 320

Ala Val Ser Leu Tyr Gly Asn Pro Val Arg Tyr Trp Glu Ile Phe Pro
                325                 330                 335

Asn Thr Phe Arg Cys Val Tyr Val Arg Ser Ala Ile Gln Leu Gly Asn
                340                 345                 350

Tyr Lys
```

```
<210> SEQ ID NO 13
<211> LENGTH: 240
<212> TYPE: PRT
<213> ORGANISM: Homo sapiens

<400> SEQUENCE: 13

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
                20                  25                  30

Cys Ser Val Ala Arg Val Gly Leu Gly Leu Leu Leu Leu Met Gly
            35                  40                  45

Ala Gly Leu Ala Val Gln Gly Trp Phe Leu Leu Gln Leu His Trp Arg
        50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
                100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
        130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
                180                 185                 190

Ser Ser Arg Val Trp Trp Asp Ser Ser Phe Leu Gly Gly Val Val His
            195                 200                 205

Leu Glu Ala Gly Glu Lys Val Val Val Arg Val Leu Asp Glu Arg Leu
        210                 215                 220

Val Arg Leu Arg Asp Gly Thr Arg Ser Tyr Phe Gly Ala Phe Met Val
225                 230                 235                 240
```

```
<210> SEQ ID NO 14
<211> LENGTH: 204
<212> TYPE: PRT
<213> ORGANISM: Homo sapiens

<400> SEQUENCE: 14

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
                20                  25                  30
```

```
Cys Ser Val Ala Arg Asp Gly Pro Ala Gly Ser Trp Glu Gln Leu Ile
        35              40              45

Gln Glu Arg Arg Ser His Glu Val Asn Pro Ala Ala His Leu Thr Gly
    50              55              60

Ala Asn Ser Ser Leu Thr Gly Ser Gly Gly Pro Leu Leu Trp Glu Thr
65              70              75              80

Gln Leu Gly Leu Ala Phe Leu Arg Gly Leu Ser Tyr His Asp Gly Ala
            85              90              95

Leu Val Val Thr Lys Ala Gly Tyr Tyr Tyr Ile Tyr Ser Lys Val Gln
            100             105             110

Leu Gly Gly Val Gly Cys Pro Leu Gly Leu Ala Ser Thr Ile Thr His
            115             120             125

Gly Leu Tyr Lys Arg Thr Pro Arg Tyr Pro Glu Glu Leu Glu Leu Leu
        130             135             140

Val Ser Gln Gln Ser Pro Cys Gly Arg Ala Thr Ser Ser Ser Arg Val
145             150             155             160

Trp Trp Asp Ser Ser Phe Leu Gly Gly Val Val His Leu Glu Ala Gly
            165             170             175

Glu Lys Val Val Val Arg Val Leu Asp Glu Arg Leu Val Arg Leu Arg
            180             185             190

Asp Gly Thr Arg Ser Tyr Phe Gly Ala Phe Met Val
        195             200

<210> SEQ ID NO 15
<211> LENGTH: 239
<212> TYPE: PRT
<213> ORGANISM: Mus sp.

<400> SEQUENCE: 15

Met Glu Ser Val Val Gln Pro Ser Val Phe Val Val Asp Gly Gln Thr
1               5               10              15

Asp Ile Pro Phe Arg Arg Leu Glu Gln Asn His Arg Arg Arg Arg Cys
            20              25              30

Gly Thr Val Gln Val Ser Leu Ala Leu Val Leu Leu Leu Gly Ala Gly
            35              40              45

Leu Ala Thr Gln Gly Trp Phe Leu Leu Arg Leu His Gln Arg Leu Gly
    50              55              60

Asp Ile Val Ala His Leu Pro Asp Gly Gly Lys Gly Ser Trp Glu Lys
65              70              75              80

Leu Ile Gln Asp Gln Arg Ser His Gln Ala Asn Pro Ala Ala His Leu
            85              90              95

Thr Gly Ala Asn Ala Ser Leu Ile Gly Ile Gly Gly Pro Leu Leu Trp
            100             105             110

Glu Thr Arg Leu Gly Leu Ala Phe Leu Arg Gly Leu Thr Tyr His Asp
        115             120             125

Gly Ala Leu Val Thr Met Glu Pro Gly Tyr Tyr Tyr Val Tyr Ser Lys
        130             135             140

Val Gln Leu Ser Gly Val Gly Cys Pro Gln Gly Leu Ala Asn Gly Leu
145             150             155             160

Pro Ile Thr His Gly Leu Tyr Lys Arg Thr Ser Arg Tyr Pro Lys Glu
            165             170             175

Leu Glu Leu Leu Val Ser Arg Arg Ser Pro Cys Gly Arg Ala Asn Ser
            180             185             190

Ser Arg Val Trp Trp Asp Ser Ser Phe Leu Gly Gly Val Val His Leu
```

-continued

```
             195                 200                 205

Glu Ala Gly Glu Glu Val Val Val Arg Val Pro Gly Asn Arg Leu Val
    210                 215                 220

Arg Pro Arg Asp Gly Thr Arg Ser Tyr Phe Gly Ala Phe Met Val
225                 230                 235

<210> SEQ ID NO 16
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Gln Val Gln Leu Gln Gln Ser Gly Ser Glu Leu Met Met Pro Gly
1               5                   10                  15

Ala Ser Val Lys Ile Ser Cys Lys Ala Thr Gly Tyr Thr Phe Ser Asn
            20                  25                  30

Tyr Trp Ile Glu Trp Val Lys Gln Arg Pro Gly His Gly Leu Glu Trp
        35                  40                  45

Ile Gly Glu Ile Leu Pro Gly Thr Gly Arg Thr Ile Tyr Asn Glu Lys
    50                  55                  60

Phe Lys Gly Lys Ala Thr Phe Thr Ala Asp Ile Ser Ser Asn Thr Val
65                  70                  75                  80

Gln Met Gln Leu Ser Ser Leu Thr Ser Glu Asp Ser Ala Val Tyr Tyr
                85                  90                  95

Cys Ala Arg Arg Asp Tyr Tyr Gly Asn Phe Tyr Tyr Ala Met Asp Tyr
            100                 105                 110

Trp Gly Gln Gly Thr Ser Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys
            100                 105

<210> SEQ ID NO 18
<211> LENGTH: 118
<212> TYPE: PRT
```

-continued

```
<213> ORGANISM: Artificial Sequence
<220> FEATURE:
<223> OTHER INFORMATION: Description of Artificial Sequence: Synthetic
      polypeptide

<400> SEQUENCE: 18

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Arg Tyr Asn Pro Ala
        50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ala
        115

<210> SEQ ID NO 19
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Tyr Trp Ile Glu
1               5

<210> SEQ ID NO 21
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Ile Leu Pro Gly Thr Gly Arg Thr Ile Tyr Asn Glu Lys Phe Lys
1               5                   10                  15

Gly

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Asp Tyr Tyr Gly Asn Phe Tyr Tyr Ala Met Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ala Ser Gln Gly Ile Asn Asn Tyr Leu Asn
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Thr Ser Thr Leu Gln Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Gln Tyr Ser Lys Leu Pro Arg Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 26

Thr Ser Gly Met Gly Val Gly
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Ile Trp Trp Asp Asp Asp Lys Arg Tyr Asn Pro Ala Leu Lys Ser
1               5                   10                  15

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Asn Pro Ala Trp Phe Ala Tyr
1               5

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Ala Ser Gln Ser Val Asp Phe Asp Gly Asp Ser Phe Met Asn
1               5                   10                  15

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Thr Ser Asn Leu Glu Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Ser Asn Glu Asp Pro Tyr Thr
1               5

<210> SEQ ID NO 32
<211> LENGTH: 5
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Gly Ser
1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Ser
1

<210> SEQ ID NO 34
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly
1

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Glu Ser Gly Ser Val Ser Ser Glu Gln Leu Ala Gln Phe Arg Ser
1               5                   10                  15

Leu Asp

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Gly Lys Ser Ser Gly Ser Gly Ser Glu Ser Lys Ser Thr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Gly Ser Ala Gly Ser Ala Ala Gly Ser Gly Glu Phe
1               5                   10

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Ala Ala Ala Lys
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Ala Ala Ala Arg
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Ala Pro Ala Pro
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Glu Ala Ala Ala Lys Glu Ala Ala Ala Lys Ala
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 10
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 43

Gly Gly Gly Gly Ser Gly Gly Gly Gly Ser
1               5                   10
```